US010515831B2

(12) United States Patent
Deo

(10) Patent No.: US 10,515,831 B2
(45) Date of Patent: Dec. 24, 2019

(54) MEDICAL INSTRUMENT FOR IN VIVO HEAT SOURCE

(71) Applicant: Anand Deo, Mendota Heights, MN (US)

(72) Inventor: Anand Deo, Mendota Heights, MN (US)

(*) Notice: Subject to any disclaimer, the term of this patent is extended or adjusted under 35 U.S.C. 154(b) by 0 days.

(21) Appl. No.: 16/027,139

(22) Filed: Jul. 3, 2018

(65) Prior Publication Data
US 2018/0323090 A1 Nov. 8, 2018

Related U.S. Application Data

(63) Continuation-in-part of application No. PCT/US2016/069490, filed on Dec. 30, 2016, which
(Continued)

(51) Int. Cl.
H01L 21/67 (2006.01)
H01L 21/324 (2006.01)
(Continued)

(52) U.S. Cl.
CPC ......... H01L 21/67103 (2013.01); A61F 7/12 (2013.01); H01L 21/324 (2013.01);
(Continued)

(58) Field of Classification Search
None
See application file for complete search history.

(56) References Cited

U.S. PATENT DOCUMENTS 3,780,255 A 12/1973 Boom
4,338,575 A 7/1982 Hartemann
(Continued)

FOREIGN PATENT DOCUMENTS

CA 2993930 2/2017
CN 106267534 A 1/2017
(Continued)

OTHER PUBLICATIONS

"U.S. Appl. No. 15/165,096, Notice of Allowance dated Aug. 31, 2016", 9 pgs.
(Continued)

Primary Examiner — Kaitlyn E Smith
(74) Attorney, Agent, or Firm — Schwegman Lundberg & Woessner, P.A.

(57) ABSTRACT

A biocompatible medical device can be at least partially implantable into a living human or animal subject to provide active treatment of biofilm that can occur use within the subject. The medical device can include a catheter, including an interior conduit capable of permitting fluid flow. A heating device can be located on a portion of the catheter to be located within the subject, the heating device including at least a pair of electrodes having a variable spacing therebetween, the variable spacing specified to allow heat to be generated using a time-varying electromagnetic input signal providing a variable frequency to control a variable location along the electrodes at which heat is generated, such as can provide a virtual matrix of local heat sources.

25 Claims, 37 Drawing Sheets

Related U.S. Application Data is a continuation of application No. 15/165,096, filed on May 26, 2016, now Pat. No. 9,536,758.

(60) Provisional application No. 62/530,035, filed on Jul. 7, 2017.

(51) Int. Cl.
*A61F 7/12* (2006.01)
*H05B 1/02* (2006.01)
*H05B 6/50* (2006.01)

(52) U.S. Cl.
CPC ....... *H01L 21/67248* (2013.01); *H05B 1/023* (2013.01); *H05B 6/50* (2013.01)

(56) References Cited

U.S. PATENT DOCUMENTS

| | | | |
|---|---|---|---|
| 4,945,912 A | 8/1990 | Langberg | |
| 5,037,395 A | 8/1991 | Spencer | |
| 5,057,105 A | 10/1991 | Malone et al. | |
| 5,191,883 A * | 3/1993 | Lennox | A61B 18/08 606/27 |
| 5,257,635 A | 11/1993 | Langberg | |
| 5,260,020 A | 11/1993 | Wilk et al. | |
| 5,290,490 A | 3/1994 | Nied et al. | |
| 5,498,261 A | 3/1996 | Strul | |
| 5,891,182 A * | 4/1999 | Fleming | A61N 1/326 128/903 |
| 6,387,052 B1 | 5/2002 | Quinn et al. | |
| 6,443,547 B1 | 9/2002 | Takahashi et al. | |
| 6,511,851 B1 | 1/2003 | Payne et al. | |
| 6,537,927 B1 | 3/2003 | Son | |
| 6,901,683 B2 | 6/2005 | Lyle et al. | |
| 7,133,180 B2 | 11/2006 | Ilchenko et al. | |
| 7,160,297 B2 | 1/2007 | Nesbitt | |
| 7,274,262 B2 | 9/2007 | Ham et al. | |
| 7,317,216 B2 | 1/2008 | Holm-Kennedy | |
| 7,393,501 B2 | 7/2008 | Zumeris et al. | |
| 7,429,719 B1 | 9/2008 | Spetz | |
| 7,844,345 B2 * | 11/2010 | Boling | A61N 1/0529 607/116 |
| 8,933,416 B2 | 1/2015 | Arcand et al. | |
| 9,008,793 B1 * | 4/2015 | Cosman, Sr. | A61B 18/1206 606/31 |
| 9,362,604 B2 | 6/2016 | Denis et al. | |
| 9,536,758 B1 | 1/2017 | Deo | |
| 2002/0065052 A1 | 5/2002 | Pande et al. | |
| 2002/0120296 A1 * | 8/2002 | Mech | A61K 9/0009 607/2 |
| 2003/0164371 A1 | 9/2003 | Bergstrom et al. | |
| 2003/0205571 A1 | 11/2003 | Flugstad et al. | |
| 2005/0068116 A1 | 3/2005 | Ham et al. | |
| 2005/0083785 A1 | 4/2005 | Shiokawa et al. | |
| 2006/0071237 A1 | 4/2006 | Deboy et al. | |
| 2007/0161263 A1 | 7/2007 | Meisner | |
| 2007/0260239 A1 | 11/2007 | Podhajsky et al. | |
| 2009/0054881 A1 * | 2/2009 | Krespi | A61B 17/22012 606/9 |
| 2009/0071952 A1 | 3/2009 | Kuwabara | |
| 2009/0131854 A1 | 5/2009 | DiCarlo et al. | |
| 2009/0162954 A1 | 6/2009 | Griffin, Jr. et al. | |
| 2010/0030210 A1 * | 2/2010 | Paulus | A61B 18/1206 606/38 |
| 2010/0036375 A1 * | 2/2010 | Regadas | A61B 17/32056 606/39 |
| 2010/0191232 A1 * | 7/2010 | Boveda | A61B 18/14 606/33 |
| 2010/0217259 A1 * | 8/2010 | Strauss | A61B 18/1233 606/38 |
| 2010/0249692 A1 | 9/2010 | Dacey, Jr. et al. | |
| 2010/0286691 A1 * | 11/2010 | Kerr | A61B 18/1206 606/51 |
| 2011/0137390 A1 * | 6/2011 | Hill | A61N 1/3931 607/116 |
| 2011/0152790 A1 | 6/2011 | Dacey, Jr. et al. | |
| 2011/0226759 A1 | 9/2011 | Wander et al. | |
| 2012/0029500 A1 * | 2/2012 | Jenson | A61B 18/1492 606/33 |
| 2012/0330393 A1 * | 12/2012 | Janik | A61N 1/0551 607/148 |
| 2013/0282084 A1 * | 10/2013 | Mathur | A61N 5/00 607/101 |
| 2014/0088674 A1 * | 3/2014 | Bradley | A61N 1/0553 607/117 |
| 2014/0257272 A1 * | 9/2014 | Clark, III | A61B 18/14 606/37 |
| 2015/0119877 A1 * | 4/2015 | Jameson | A61B 18/1492 606/41 |
| 2017/0258628 A1 * | 9/2017 | Awasthi | A61F 7/007 |
| 2018/0042667 A1 | 2/2018 | Pappone et al. | |
| 2019/0109024 A1 | 4/2019 | Deo | |

FOREIGN PATENT DOCUMENTS

| | | |
|---|---|---|
| EP | 3113281 A1 | 1/2017 |
| GB | 1529941 | 10/1978 |
| WO | WO-2012153529 A1 | 11/2012 |
| WO | WO-2016181397 A1 | 11/2016 |
| WO | WO-2017204860 A1 | 11/2017 |
| WO | WO-2019010238 A1 | 1/2019 |

OTHER PUBLICATIONS

"International Application Serial No. PCT/US2016/069490, International Preliminary Report on Patentability dated Jul. 10, 2018", 1 pg.

"International Application Serial No. PCT/US2016/069490, International Search Report dated Mar. 8, 2017", 2 pgs.

"International Application Serial No. PCT/US2016/069490, Written Opinion dated Mar. 8, 2017", 7 pgs.

Beringer, Robert, "The Measurement of Wavelength—Chapter 5 from Technique of Microwave Measurements", vol. 11 of MIT Radiation Laboratory Series. McGraw-Hill, New York, (1947), 58 pgs.

Gopinath, A., et al., "Capacitance Parameters of Discontinuities in Microstriplines", IEEE Trans. on Microwave Theory and Techniques, vol. MTT-26, No. 10, (Oct. 1978), 831-836.

Mahan, Gerald, et al., "Thermoelectric Materials: New Approaches to an Old Problem", Physics Today, (Mar. 1997), 42-47.

O'Toole, Ann, et al., "Thermal Mitigation of Pseudomonas Aeruginosa Biofilms", Biofouling 31.8 (2015): 665-675. PMC., (2015), 20 pgs.

Richardson, Ian P., et al., "Hemodialysis Catheter Heat Transfer for Biofilm Prevention and Treatment", ASAIO J. 2016; 62(1): 92-99. doi:10.1097/MAT.0000000000000300, (2016), 17 pgs.

"International Application Serial No. PCT/US2018/040812, International Search Report dated Sep. 19, 2018", 2 pgs.

"International Application Serial No. PCT/US2018/040812, Written Opinion dated Sep. 19, 2018", 6 pgs.

"U.S. Appl. No. 16/200,120, Examiner Interview Summary dated Apr. 11, 2019", 3 pgs.

"U.S. Appl. No. 16/200,120, Notice of Allowance dated May 22, 2019", 5 pgs.

"U.S. Appl. No. 16/200,120, Response filed Mar. 25, 2019 to Non-Final Office Action dated Jan. 24, 2019", 16 pgs.

"U.S. Appl. No. 16/200,120, Supplemental Response filed Apr. 8, 2019 to Non-Final Office Action dated Jan. 24, 2019", 10 pgs.

"European Application Serial No. 16903365.1, Extended European Search Report dated May 17, 2019", 8 pgs.

"U.S. Appl. No. 16/502,989, Preliminary Amendment filed Jul. 11, 2019", 4 pgs.

"International Application Serial No. PCT US2019 040588, International Search Report dated Oct. 8, 2019", 2 pgs.

(56) References Cited

OTHER PUBLICATIONS

"International Application Serial No. PCT US2019 040588, Written Opinion dated Oct. 8, 2019", 5 pgs.

* cited by examiner

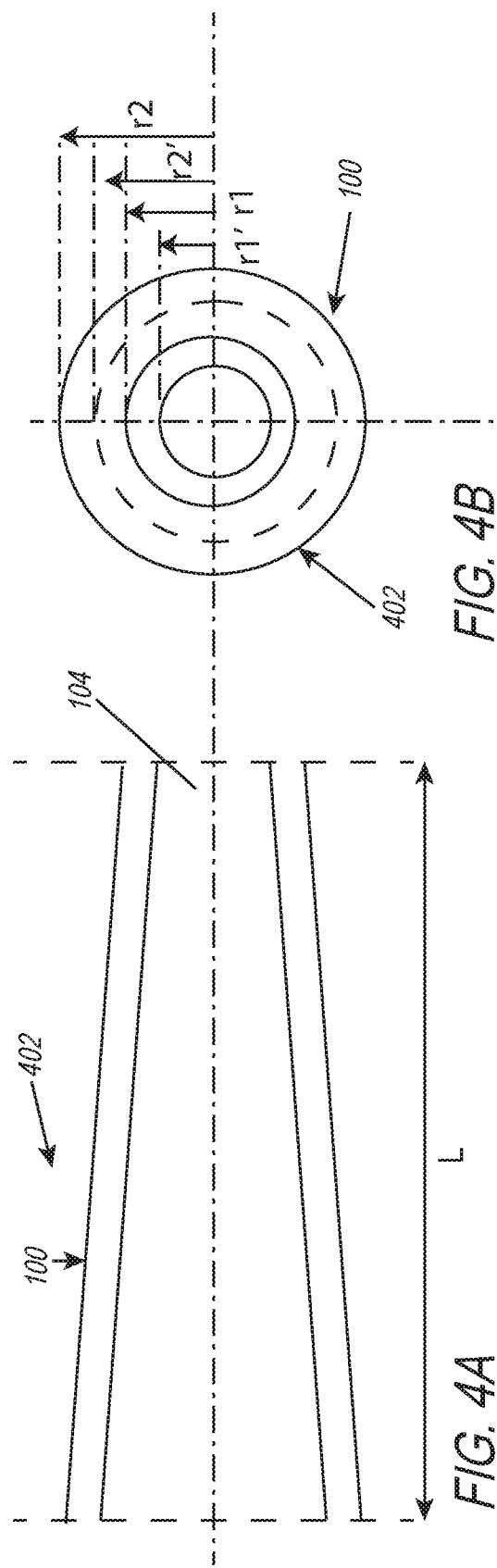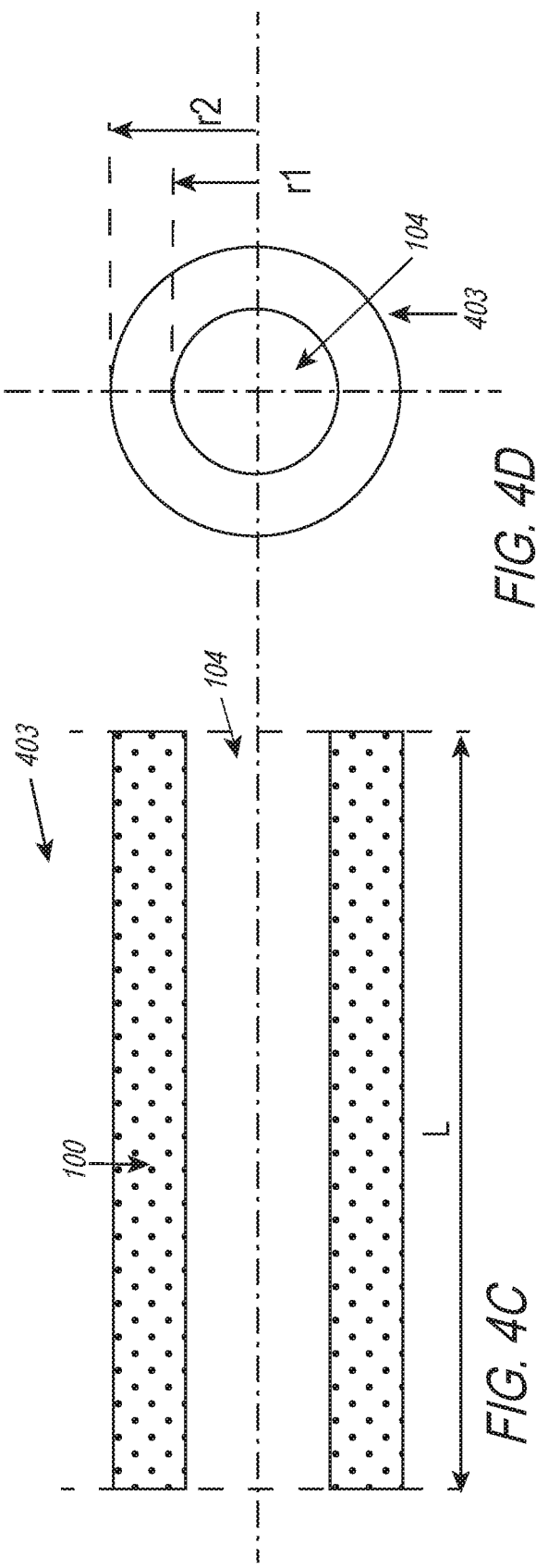
FIG. 4A
FIG. 4B
FIG. 4C
FIG. 4D

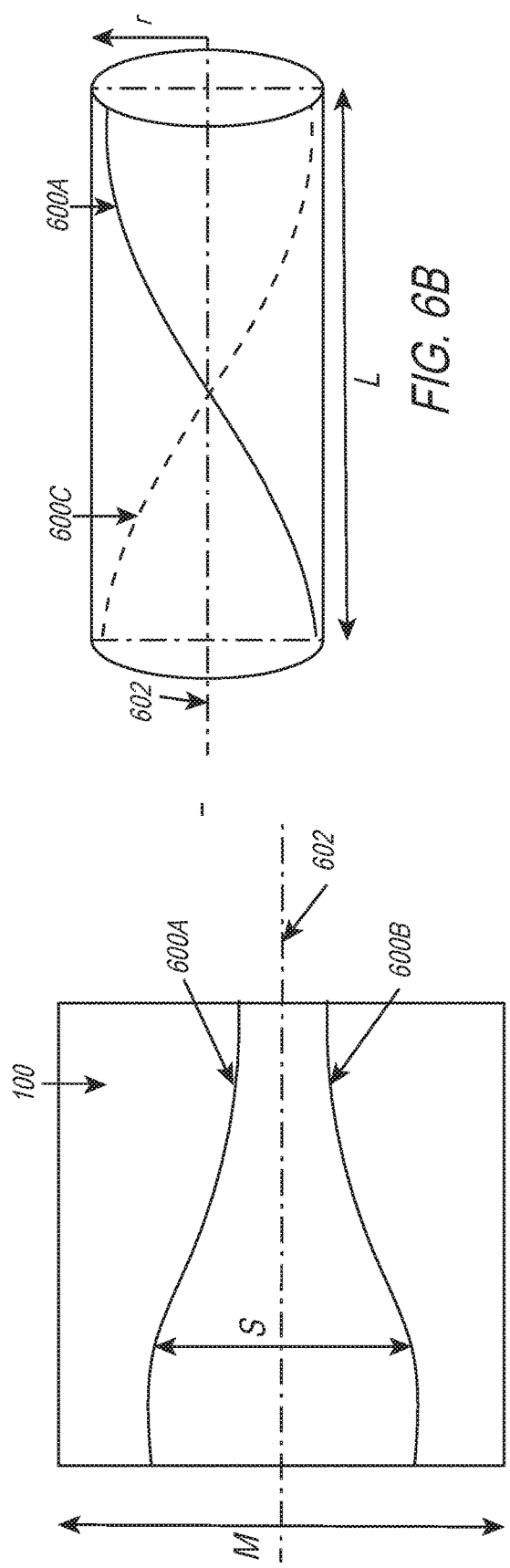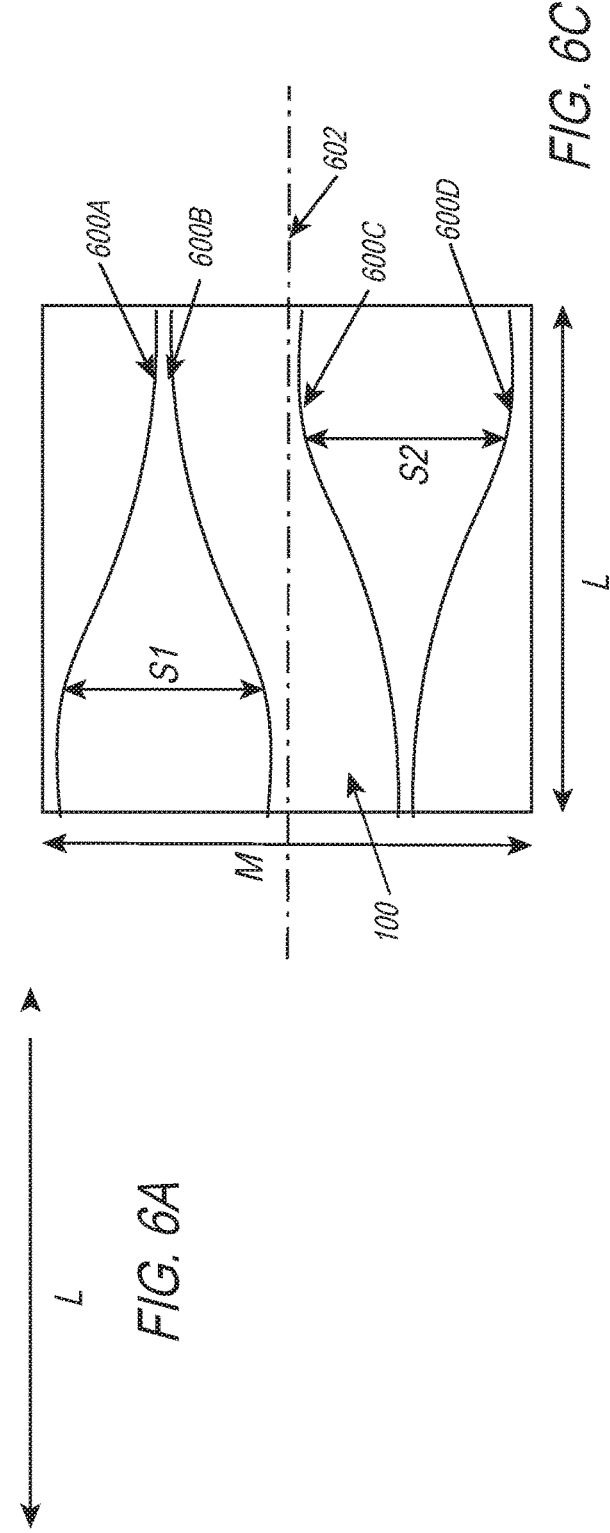

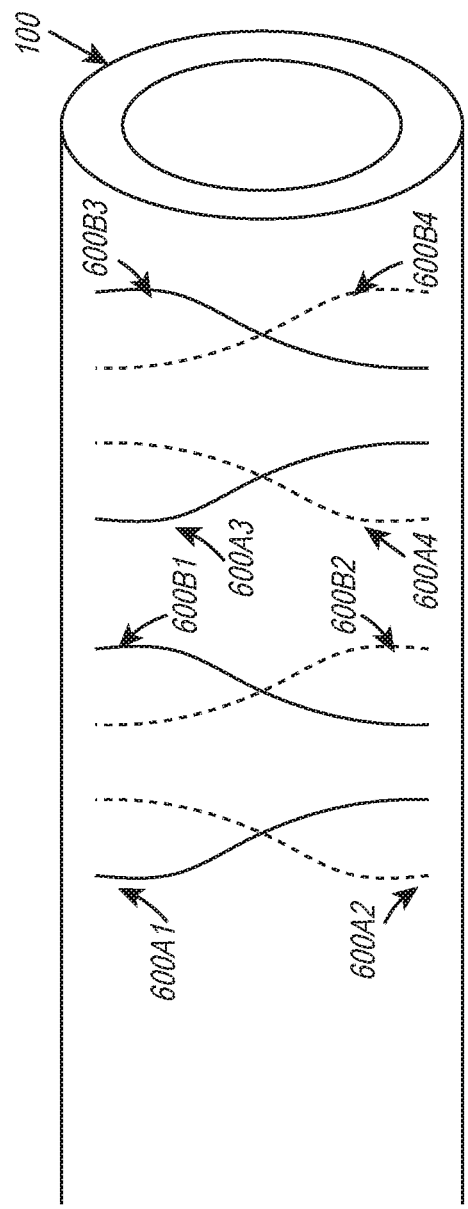

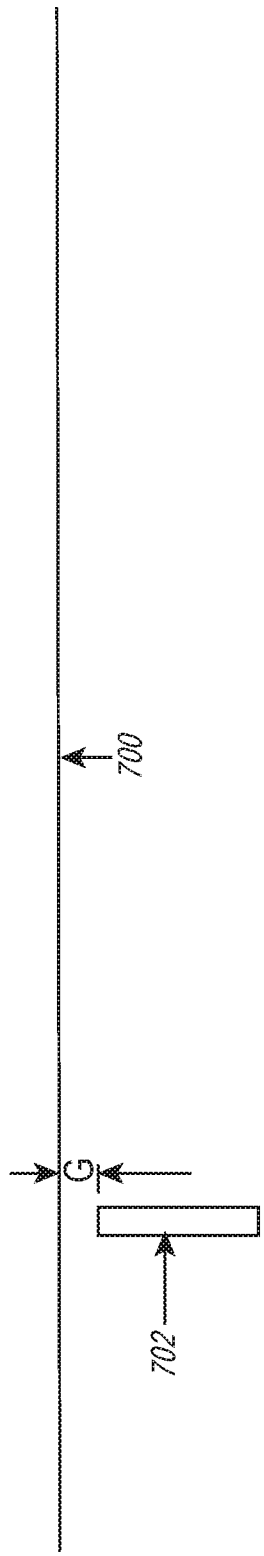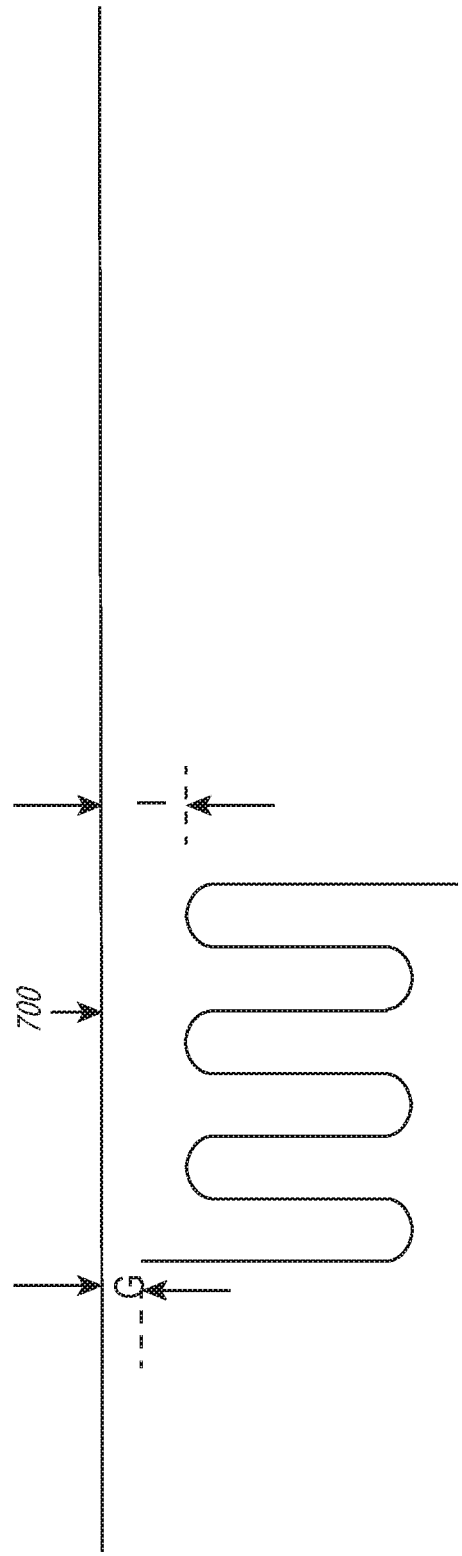

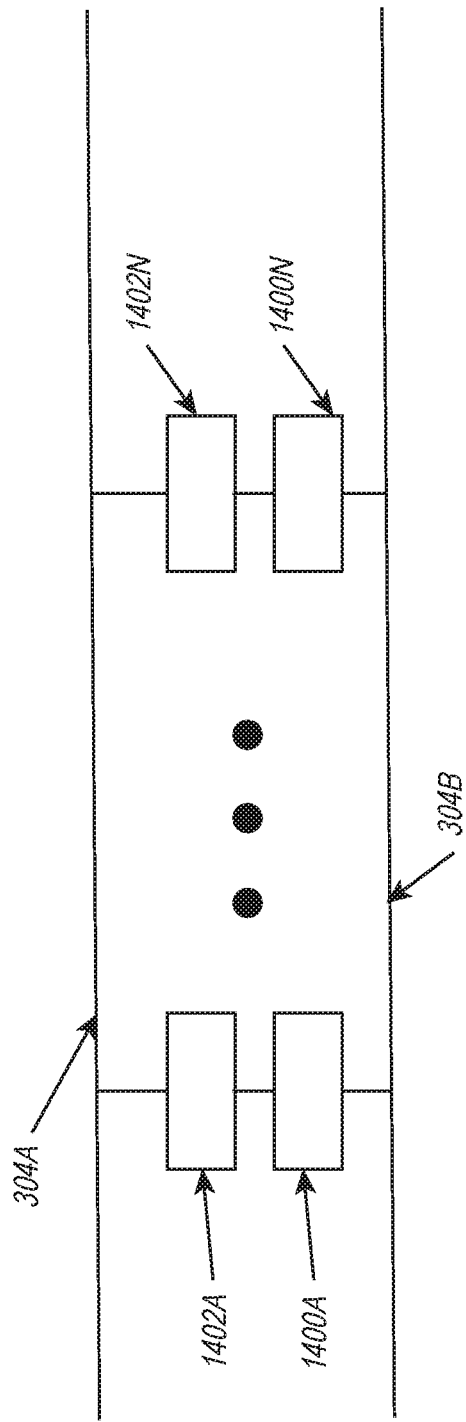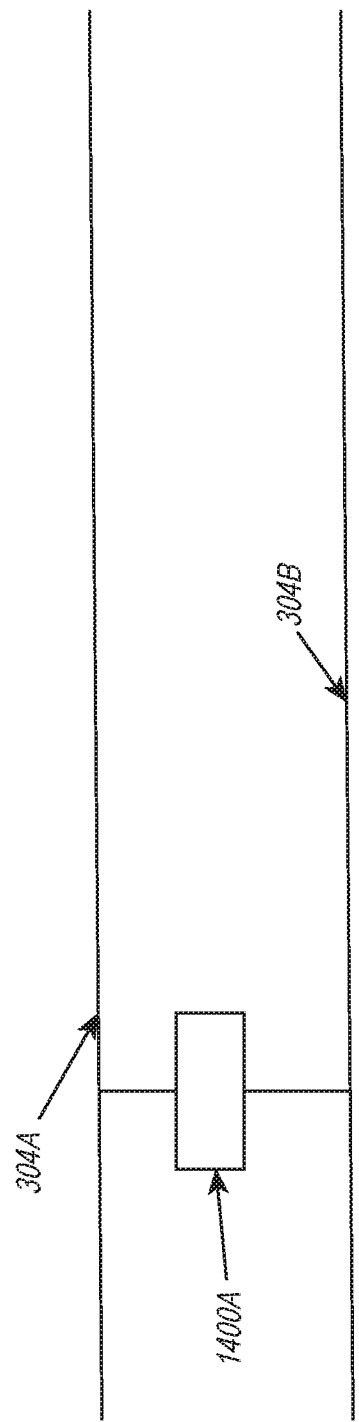

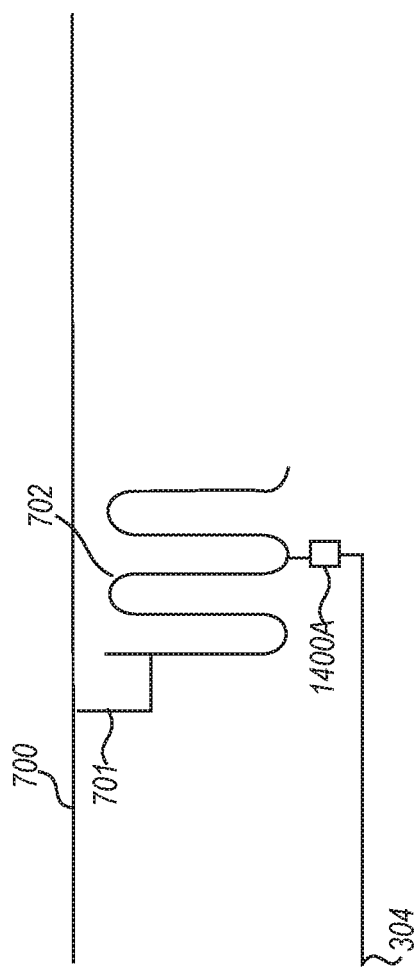

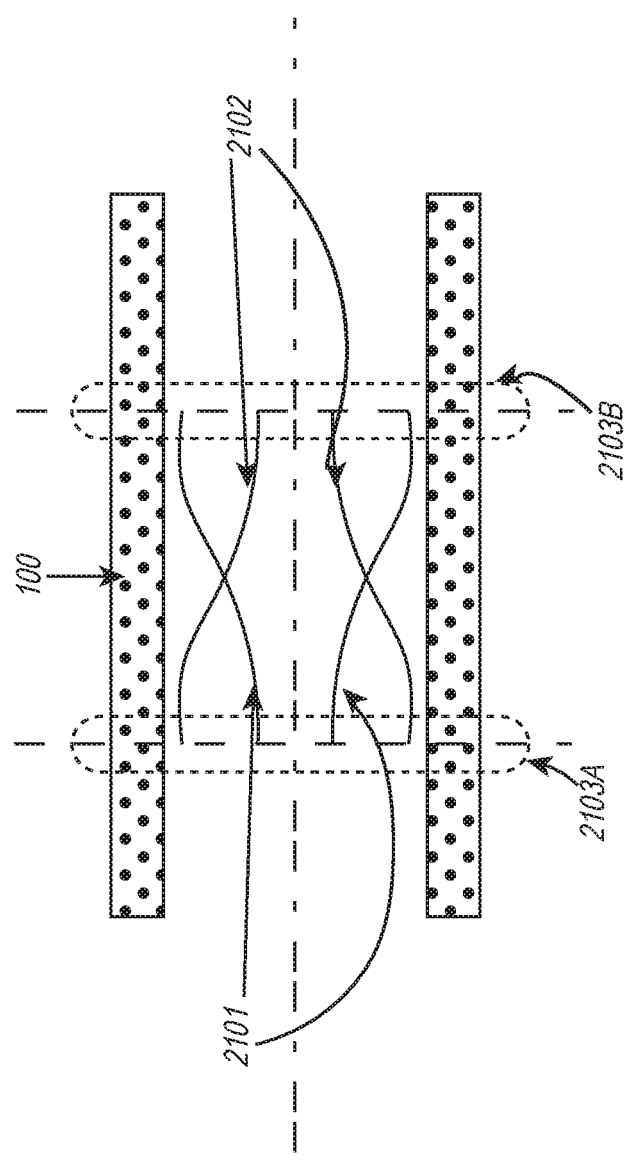

| 2.0 Ghz ⑥<br>T6 | 2.2 Ghz ⑦<br>T7 | 2.4 Ghz ⑧<br>T8 | 2 Ghz ⑨<br>T9 | 2.8 Ghz ⑩<br>T10 |
|---|---|---|---|---|
| 1 Ghz ①<br>T1 | 1.19 Ghz ②<br>T2 | 1.2 Ghz ③<br>T3 | 1.3 Ghz ④<br>T4 | 1.6 Ghz ⑤<br>T5 |

*FIG. 22C*

MEDICAL INSTRUMENT FOR IN VIVO HEAT SOURCE

CLAIM OF PRIORITY

This patent application claims the benefit of priority of U.S. Provisional Patent Application Ser. No. 62/530,035, filed Jul. 7, 2017, entitled CATHETER TO INHIBIT BIOFILM OR INFECTION, and is a continuation-in-part under 37 C.F.R 111(a) of PCT Patent Application No. PCT/US2016/069490, filed Dec. 30, 2016, entitled TIME VARYING FREQUENCY POWERED HEAT SOURCE, which claims the priority of U.S. patent application Ser. No. 15/165,096 (now U.S. Pat. No. 9,536,758, issued on Jan. 3, 2017) entitled TIME VARYING FREQUENCY POWERED SEMICONDUCTOR SUBSTRATE HEAT SOURCE, each of which is hereby incorporated herein by reference in its entirety, and the benefit of priority of each of which is claimed herein.

TECHNICAL FIELD

This document pertains generally, but not by way of limitation, to medical devices, such as for example catheters, for insertion or implantation into a human or animal subject.

BACKGROUND

Infection control in a living body (e.g., in vivo) without requiring the use of an antibiotic is a critical need. This is because bacteria are getting resistant to antibiotics and animals are getting allergic to them due to overuse.

A pre-sterilized medical device can include at least a portion that can be chronically inserted or implanted into a living subject, such as a human or animal patient or subject, and such inserted or implanted portion can eventually form a bio-film on its surface. This, in turn, can lead to infection, which is an undesirable complication of the medical procedure that can compromise the procedure, the health of the patient, and can add to the monetary cost of care—which can extend well beyond the cost of the medical procedure itself. Such added costs may not be reimbursed by an insurance provider.

SUMMARY

The present inventor has recognized, among other things, that over an extended period of time a long-dwelling medical device, such as a central line or other catheter or shunt, can accumulate a bio-film on a surface of the device, such as on a surface that is exposed to biological fluid that is present or flowing through or about the device (e.g., urine, blood, cerebrospinal fluid, or the like). Such a bio-film can be a source of infection, particularly during extended chronic use of the medical device.

The present inventor has recognized that heat can be effective at neutralizing bio-film, but that there is a challenge in creating and effectively using heat in-vivo without triggering adverse biological or metabolic effects from such in-vivo administration of thermal energy. This challenge can be addressed by controlling the amount of thermal energy injected in vivo into the biological or metabolic system at a given time and, in an example, modulating the application of thermal energy to be within the tolerance of, or in response to, one or more biological or metabolic processes (e.g., such as can include, but are not limited to, the body's natural physiological thermal regulation or stabilization, thrombosis, or even tissue necrosis).

The present inventor has also recognized that an appropriate electrical charge can optionally be provided in vivo to attract bacteria toward an appropriate heat treatment location on the medical device, such as to permit heat treatment to neutralize the attracted bacteria or associated bio-film. Bacteria, especially pathogenic bacteria, can have a negative electrical charge. Thus, an appropriate positive electrical charge can be applied and provided on the medical device, e.g., at or near a localized heat source on the medical device, such as to attract the bacteria toward the localized heat source for heat neutralization to help reduce, avoid, or treat a bacterial infection. The positive electrical charge can be applied in vivo by an electrostatic material layer that has been precharged to an appropriate positive voltage, e.g., 15 mV or greater, to attract the negatively charged bacteria. Alternatively or additionally, the positive electrical charge can preferably be applied in vivo by providing a positive DC or slowly varying AC offset voltage superimposed onto the electromagnetic input signal being applied to the variable spacing electrodes, planar transmission line resonators, or other devices being used to actuate heat generation. If a slowly varying AC offset voltage is used, its frequency should be slow enough to permit the an attractive electrostatic force to draw close the negatively charged pathogen in vivo during the positive phase of the applied AC offset voltage to allow heat sterilization during or after the positive phase of the applied AC offset voltage and before any negative phase of the applied AC offset voltage. In an example, the sweep activation of the localized heat sources, such as described herein, can be interleaved with the positive voltage pathogen-attracting signal being applied, such as to the electrical traces 302A-B. Thus, the present techniques can permit in vivo heat sterilization or pasteurization of either device-born or free-flowing infectious bacteria, or both.

This document describes devices and methods that can permit safe and reliable in-vivo active thermal sterilization of a catheter, shunt, or other medical device that is inserted into or completely implanted within the living subject. It can help reduce or even eliminate the formation of bio-film, can help neutralize existing bio-film, or both, by itself, or by combining the thermal sterilization with an adjunct treatment, such as mechanical vibration or cutting. It can allow localized active thermal sterilization such that damage to nearby tissue by the thermal energy used to modify the bio-film can be avoided or can be held to within a desired biological tolerance. As explained herein, providing fast-acting and focused heat can help address biofilm while staying within the subject's biological tolerance for heat without side-effects. This can help reduce or minimize total time of heating and, therefore, reduce or minimize dissipation of heat into the subject's body (unless such heat dissipation is desired, such as for providing an in vivo heat therapy).

An improved and more efficient in vivo sterilization process is possible when a device can be configured and operated with temperature sensing and regulation, such as to take advantage of the subject's body's natural (e.g., normal or impaired) thermal stabilization for safe in-vivo device sterilization operation. The present approach can help permit in-vivo heat-sterilization or other heat treatment by a medical device, such as by using a selected heating location "point" (or region) on a surface or volume of the medical device, which can optionally be selected to be located in association with a desired target tissue location or organ (e.g., such as for a heat therapy delivery application). The surface or volume can be broken down into or assigned or configured with a specified matrix of individually controllable local heat sources at such specified locations or points or regions of the surface or volume. This matrix approach to in vivo heat delivery sources can help enable higher local temperatures, such as sterilization-grade local temperatures, for specified durations, while avoiding damage to nearby tissue.

In an example, applying heat at the individually controllable local heat source locations can be controlled, such as by adjusting the frequency of an electromagnetic input signal that can be provided to a matrix of heat sources that can by dynamically formed in an adjacent active substrate by one or a combination of electrodes, resonators, strip-lines, or other heat source structures on the medical device that can be arranged to vary the in vivo location of heat generation in the adjacent or nearby active substrate in response to varying the frequency of the applied electromagnetic input signal. A non-optical electromagnetic input signal can be used, such as to allow non-optical electromagnetic signal conduction from an external location to an insertable or implantable in vivo location via electrically conductive traces, without requiring an optical fiber to transmit light or an optical frequency range electromagnetic signal. Using frequency control to adjust the location of heat delivery can help avoid the need to provide individual electrical conductors for selectively accessing individual local heating sources for generating heat. A "virtual" (frequency-controlled) matrix can be provided, rather than providing a physical matrix in which each heat source is addressed separately using a complex switching circuit for the selective accessing of local heat sources. This, in turn, can help enable the miniaturization that can be needed for certain percutaneous or fully implantable medical device applications, such as for a catheter or shunt. Frequency control to adjust heat delivery locations within the matrix can reduce the number of control paths into the heating surface or into the device itself. Frequency control accessing and activation and dynamic formation of localized heat sources in an adjacent or nearby active substrate using a specified frequency can help enable micro-fine heat focusing, such as can use an extremely small size of a heat source. This, in turn, can help enable localized in vivo thermal sterilization or other heat-based interference with or inhibition of a bio-film or in vivo heat therapy, while reducing, minimizing, avoiding, enabling, or controlling thermal effects on nearby tissue or other biological substances of the subject.

Moreover, such frequency controlled accessing and activation and dynamic formation of localized heat sources in an adjacent or nearby active substrate can include multi-level frequency control—such as frequency-controlled selection between different control structures (e.g., electrodes, resonators, strip-lines, or other heat source structures) within the matrix of such heat control structures, or at different locations within such different control structures, or both. For example, in the case of using a matrix of pairs of electrodes with a variable spacing therebetween, the frequency of an applied electrical or electromagnetic signal can be used to activate one or more particular pairs of electrodes within the matrix, or to activate a particular location within the particular pair of electrodes (e.g., corresponding to a specified spacing between the electrodes in the pair, or both, such as to control the location in an adjacent or nearby active substrate at which such a frequency controlled applied electromagnetic input signal dynamically creates a heat source.

For example, the present approach makes it possible to implement and control a smart multi-functional catheter or other medical device. The catheter can include one or more sensors, such as to permit in vivo measurement of one or more physical parameters, such as temperature, fluid flow velocity, or fluid pressure. In an example, the catheter can include one or more microdevices or nanodevices or other devices, such as to perform one or more physical operations, such as mechanically shaking, or cutting off, or reaming bio-film or dead tissue, such as to de-clog an orifice or fluid conduit of the catheter.

The present approach recognizes that selectively activated focused localized heat sources can take on temperatures far higher than a global counterpart, particularly in vivo, in which too much thermal energy can damage biological tissue or fluid of a subject. Localized higher temperatures, and their associated temperature gradients between such localized matrix heat source locations, can also help deliver better treatment of bacteria or bio-film.

Each of these non-limiting examples can stand on its own, or can be combined in various permutations or combinations with one or more of the other examples.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 4A, 4B, 4C, and 4D show illustrative examples of a distal portion of a medical device such as a tubular catheter.

FIG. 6A (flattened planarized view) and FIG. 6B (side view as applied to a circumference of cylindrical catheter) show an illustrative example of a possible cylindrically "coplanar" arrangement of electrodes.

FIG. 6C (flattened planarized view) shows an example of electrodes on opposing cylindrical surfaces of a catheter.

FIG. 6F (side view) illustrates an example in which pairs of electrodes can additionally or alternatively be arranged along the catheter such that an interelectrode spacing S varies circumferentially about a circumference or periphery of the catheter, but in which separate pairs of electrodes can be provided on opposing sides of the catheter.

FIG. 13B shows a top view of an example illustrating how a resonant cavity can be capacitively coupled to a main line.

FIG. 13C shows a top view of an example of a serpentine or meandering resonant cavity trace of a planar resonator line that can be capacitively coupled to a main line by an insulating gap, G, at a desired capacitive coupling location.

FIG. 14A shows an example in which temperature or other sensors can be located and electrically connected in parallel with each other at various locations along a length of a catheter.

FIG. 14B shows an example in which the sensors include a frequency-selective filter, such as can allow frequency-selective addressing of a particular temperature sensor.

FIG. 14C shows an example in which the temperature or other sensors are dedicated to or co-integrated with corresponding local heat sources.

FIGS. 21A, 21B, and 21C (cross-sectional side views) show illustrative examples of mechanical output transducers such as can optionally be included at one or more select locations along the length of the catheter, such as can provide a mechanical force or movement, such as one or more of vibration (e.g., FIG. 21A), lifting (e.g., FIG. 21B), or bending (e.g., FIG. 21C) of a desired portion of the catheter.

DETAILED DESCRIPTION

Figure 1A:
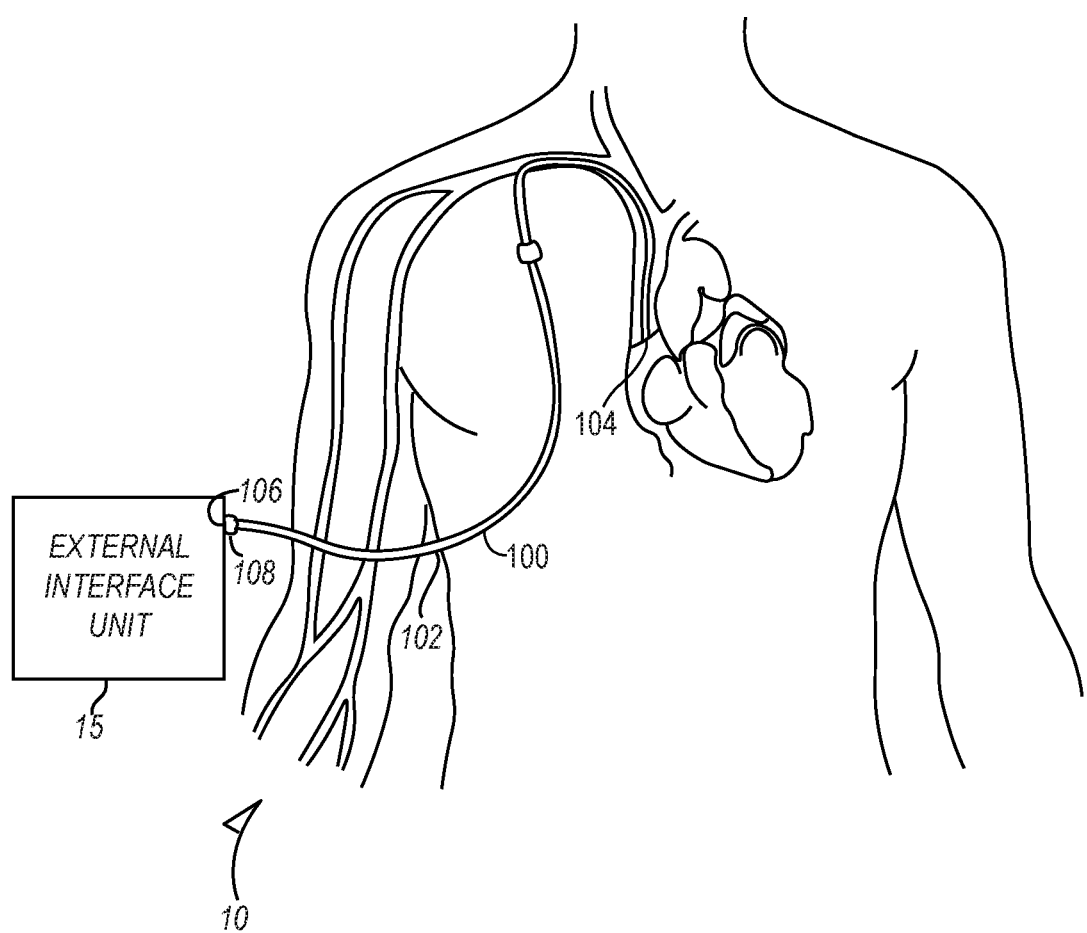
FIG. 1A shows an illustrative example of portions of a medical system that can include an at least partially implantable or insertable medical device, such as, by way of illustrative example, but not by way of limitation, a catheter in a central venous catheter application or use case.

The present approach makes it possible to take a highly localized specific point or location or region (e.g., on a portion of a medical device that can be located in-vivo) to a very high temperature, such as while providing one or more specified temperature gradients in one or more nearby or surrounding locations or regions. By establishing localized heat gradients, one can reduce or minimize the amount of heat needed to attain a desired heated temperature at one or more desired locations. This can reduce the overall amount of aggregate heat generated along an extended in vivo region of the catheter. When heat is selectively locally generated or applied at a precise location, one can increase the local temperature at that precise location to a temperature value that can be far higher than if the same temperature were to be applied more globally across a larger surface area or volume. This selective, localized approach can enable heat sterilization (or other heat treatment, e.g., such as heat-assisted biofilm disruption) of the surface to be locally provided, e.g., point-by-point or region-by-region, at much higher local temperatures without causing damage or undesired effects to nearby blood or tissue. Moreover, this approach can also use relatively low power, because it only needs enough energy to heat a small localized volume or area at any given time during the process.

Establishing a heat gradient between selectively controllable heat source locations can reduce a rate of dissipation of heat from the location of interest while still maintaining a desired objective, such as biofilm neutralization. This, in turn, can allow establishing or maintaining a higher temperature at the location of interest, which can help achieve the desired objective while helping avoid unwanted thermal side effects that may otherwise occur if a larger heating zone were needed to achieve the same temperature over a larger region. Raising a larger heating zone to the same temperature would increase the total thermal energy introduced into the biological system, which in turn may in certain instances or applications increase the probability of triggering an unwanted biological reaction to the heating.

An example of using frequency control to select the location at which thermal energy is generated is described in U.S. Pat. No. 9,536,758 B1 entitled, TIME-VARYING FREQUENCY POWERED SEMICONDUCTOR SUBSTRATE HEAT SOURCE, which is incorporated herein by reference in its entirety, including its description of arrangement and placement of electrodes or other devices, structures, and methods for using frequency control of an input signal to select or vary the location at which thermal energy is generated, such as for rastering, scanning, or otherwise selecting, serializing, or otherwise moving a localized heat generation location, such as can be used such as described herein for sterilizing or otherwise disrupting a bio-film in-vivo.

The present approach can be used to sterilize or otherwise treat a large surface area or volume, such as by creating an addressable matrix of focused local heat sources, such as can include selecting or varying an input signal frequency to control heat delivery location and temperature there or nearby. In an example, an entire catheter can be heat sterilized in vivo by providing heat at individual local heating sources arranged in a matrix that can extend over all or over one or more selected portions of the catheter, such as in a pre-programmed progressive pattern that can cover the entire surface or volume of the catheter to be treated in vivo.

The present approach can vary the input signal frequency to selectively control the precise location of heat generation and delivery. Such frequency control for selectively addressing and activating individual local heat sources within a virtual matrix of available heat sources can reduce the number of control wires needed as compared to a physical matrix approach (which is also within the contemplation of the present subject matter) in which individual heat sources would be addressed and accessed through an independent control path of electrical conductors and switches or the like.

The present approach enables concurrent or independent frequency, thermal, or electrical actuation or control, such as for selective activation in vivo of at least one of: one or more localized heat sources, one or more other mechanical actuators or mechanical transducers (e.g., such as piezoelectric or other vibrators or micromechanical devices), or one or more sensors. For example, the present approach can include one or more sensors (e.g., corresponding to one or more locations or physical quantities to be sensed, detected, or measured). A "smart" catheter or other medical device can be created by placing one or more sensors on the same medical device, such as to gather physical or physiological information, such as one or more of temperature, fluid flow velocity, fluid pressure, or the like. In an illustrative non-limiting example, such fluid velocity or pressure information can be used, for example, to diagnose whether a catheter with a fluid flow lumen or passage therewithin has become, or is becoming, impeded, which can indicate whether the catheter is becoming clogged. The sensed information can also be used to control heat generation or other mechanical or other actuation. For example, if a particular heat source is located on the catheter body within a blood vessel, then sensed blood flow velocity information may be used to titrate the amount of heat generation at that location, such as to avoid damaging blood cells or to utilize the circulatory flow capacity to dissipate heat in calculating how much heat to generate at that location, and to control such heat generation accordingly.

One or more piezoelectric devices can be included, such as for actuation (e.g., such as to provide one or more of vibration, displacement, or other movement) or sensing (e.g., such as of one or more of pressure, bending, flow, or the like), or both actuation and sensing. For example, actuated vibration or movement can provide additional help in interfering with or disrupting bio-film or unclogging the catheter. For example, such actuator devices can be used to vibrate the catheter to lift it off adjacent biofilm or tissue, cut off dead tissue, and more.

For comparison to the present approach of localized in vivo heat sterilization, other approaches may include using a chemical coating, which can be applied to a surface of a medical device to inhibit formation of bio-film. Such coatings are generally passive in their approach to bio-film inhibition. Chemicals have a limited usable life before they become ineffective. Another approach can include using an inductive framework to generate heat to sterilize a catheter, such as by using inductive nanoparticles to which a magnetic field can be applied to generate heat. However, such inductive coupling does not permit localized heat generation, and can require a large amount of power for a catheter that can be located deep within the body tissue of a subject. Nonetheless, one or more of these other approaches may optionally be used, for example, in combination with the present approach of using localized in vivo heat sterilization.

FIG. 1A shows an illustrative example of portions of a medical system 10 that can include an at least partially implantable or insertable medical device, such as, by way of illustrative example, but not by way of limitation, a catheter 100. The system 10 can also include an external interface unit 15. In this example, the catheter 100 can include a fluid delivery catheter 100, which can define a fluid delivery lumen 102, extending from a catheter distal port 104 to a catheter proximal port 106. The proximal port 106 can be connected to a fluid coupler 108 of the external interface unit 15.

In FIG. 1A, an illustrative example of a central venous catheter 100 use case is shown, such as with a subclavian vein insertion of the catheter 100 into a human or other living subject's venous system, with the distal port 104 of the catheter 100 positioned to be located within or near a right atrium of the subject's heart, such as for drug or other fluid delivery to that selected location within the subject. In the example of FIG. 1A, the catheter 100 is shown as exiting the subclavian vein and being tunneled subcutaneously to an exit site, such as can be located in or near a pectoral or other specified region of the subject. From the exit site, the catheter 100 can extend externally toward and attach to the external interface unit 15, such as at its fluid coupler 108. In an example, the external interface unit 15 can include an infusion pump, which can be controlled to expel fluid from a reservoir into the catheter 100, such as for delivery into the subject at its distal port 104. Such a pump is not required. For example, additionally or alternatively, one or more infusion ports can be provided, such as at the external interface unit 15 (see, e.g., FIG. 2B), such as to allow a clinician or other user to use a syringe or other device to inject a fluid, via an infusion port, into a proximal end of the catheter 100 for delivery to the subject via the distal port 104 of the catheter 100. In an example, the catheter can be used for drainage, instead of or in addition to infusion, such as by replacing one or more of the infusion ports by a drainage port.

Figure 1B:
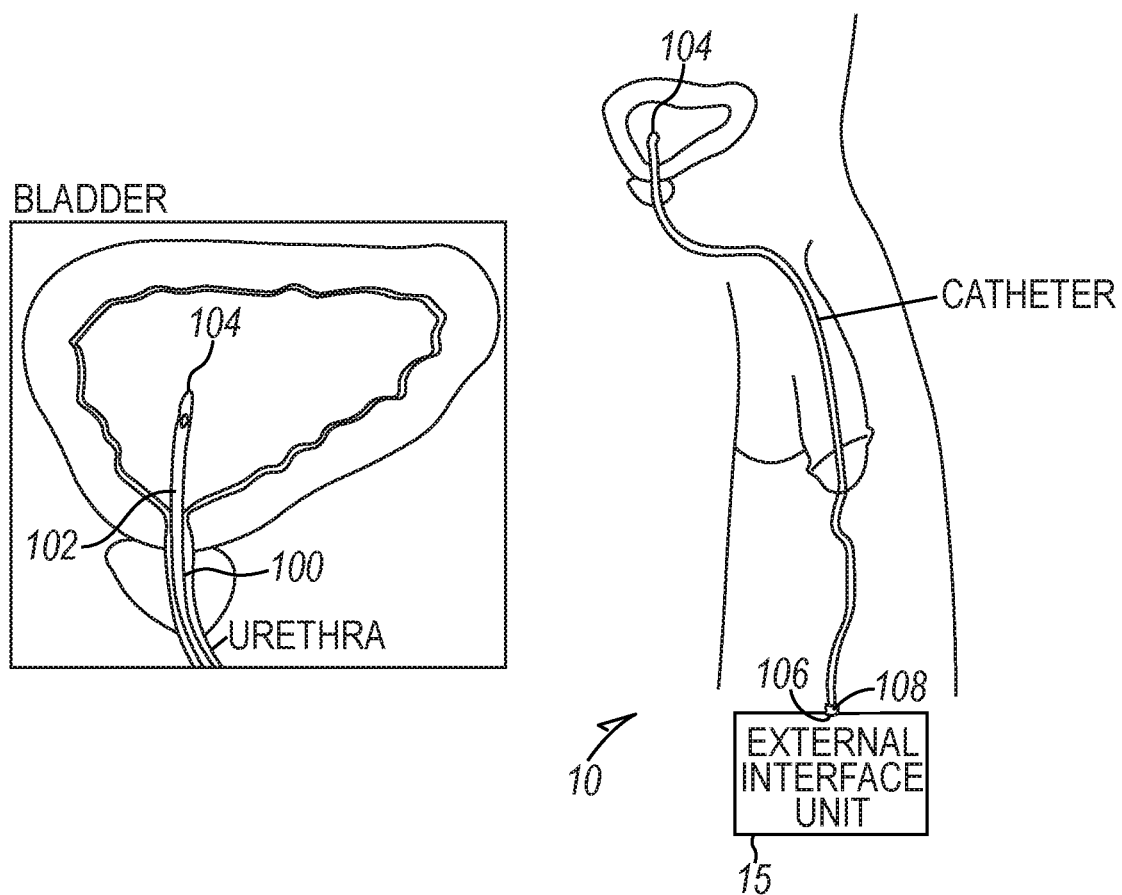
FIG. 1B shows an illustrative example of portions of a medical system that can include an at least partially implantable or insertable medical device, such as, by way of illustrative example, but not by way of limitation, a catheter in a urinary catheter application or use case.

FIG. 1B shows an example of portions of the system 10 in a urinary application. In FIG. 1B, the catheter 100 can include a urinary catheter 100 such as can be inserted via a subject's urethra to locate the distal port 104 within a bladder of the subject. In certain examples, a wall of the catheter 100 can taper inward at or near the distal port 104 of the catheter 100, such as to provide a tapered distal tip of the catheter 100. Urine can flow through an inner lumen of the catheter 100, such as from the distal port 104 to the proximal port 106, such as to provide drainage of urine from the subject to an external location. In chronic use, such as in this urinary application, biofilm can build within the inner lumen of the catheter 100 or around the outer circumferential periphery of the catheter 100, either within the portion of the catheter 100 that is located within the bladder, or within the portion of the catheter 100 that is located within the urethra.

Figure 1C:
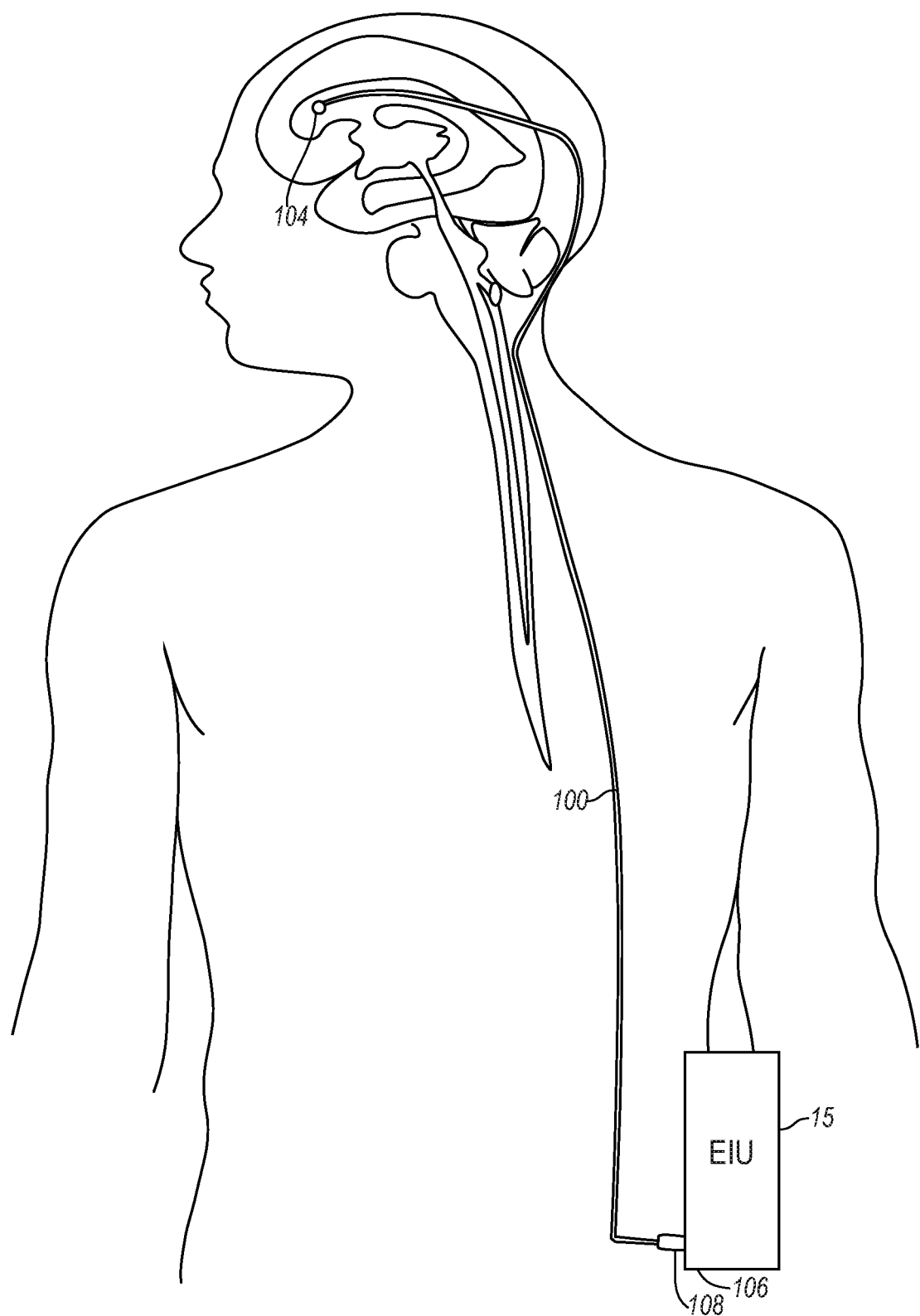
FIG. 1C shows an illustrative example of portions of a medical system that can include an at least partially implantable or insertable medical device, such as, by way of illustrative example, but not by way of limitation, a catheter in a cerebrospinal catheter application or use case.

FIG. 1C shows an example of portions of the system 10 in a cerebrospinal application. In FIG. 1C, the catheter 100 can include a drug delivery catheter 100 such as can be inserted with its distal port 104 located within an intraventricular space within the subject's head, such as to deliver medication sourced by an infusion pump or infusion port that can be associated with the external interface unit 15. In chronic use, such as in this cerebrospinal application, biofilm can build within the inner lumen of the catheter 100 or around an outer circumferential periphery of the catheter 100.

Although FIGS. 1A, 1B, 1C illustrate various examples of medical devices, such as can include catheters, shunts, or other devices, in various examples of use cases, the present techniques can be applicable to other insertable or implantable or other medical devices, other use cases, and in various applications outside of the field of medical devices. The in vivo heat generation of the present approach, such as described herein, can be used for bacteria or biofilm neutralization, or for one or more other in vivo heating applications, such as in vivo heat therapy to tissue or the like.

Figure 2A:
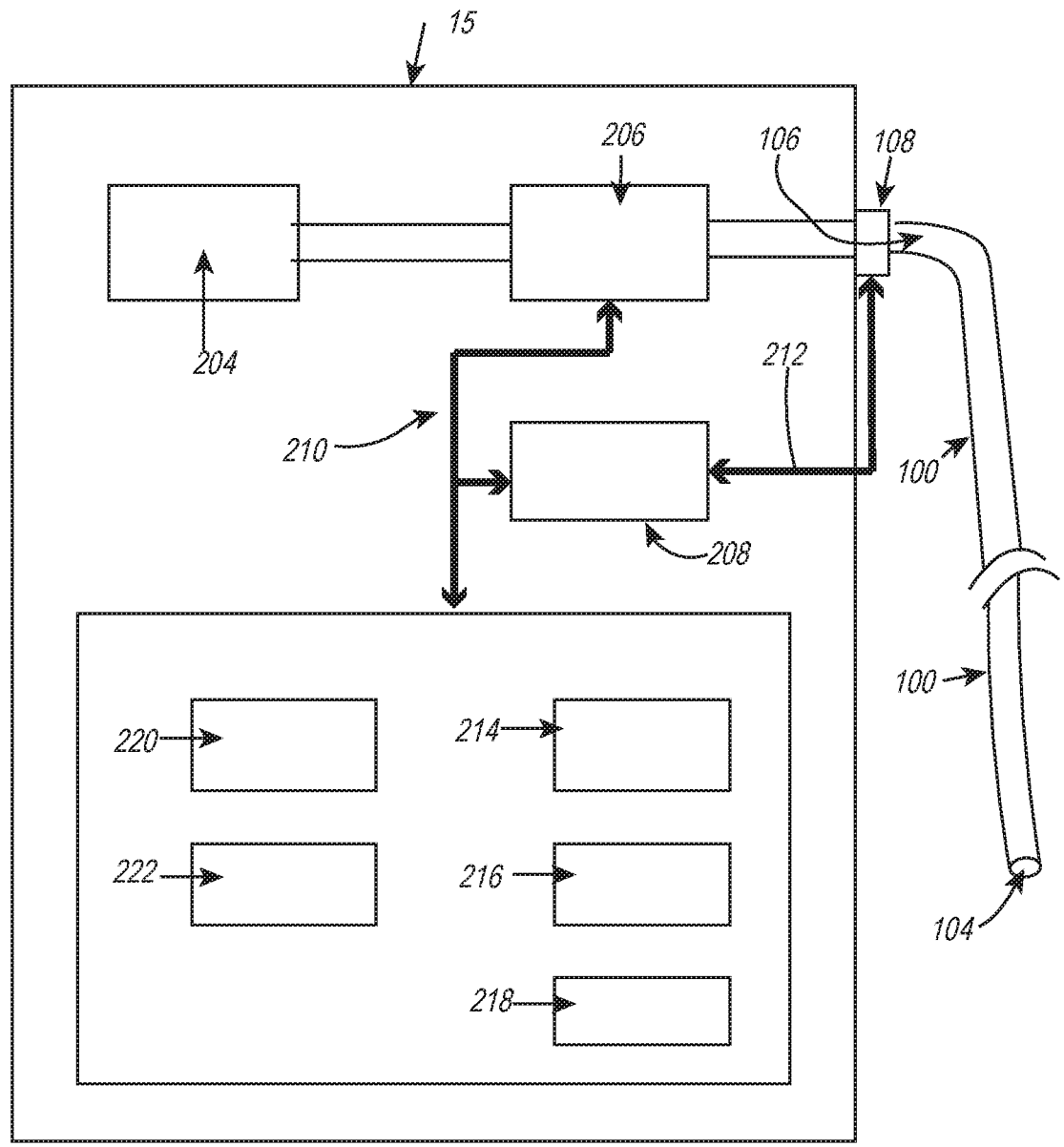
FIG. 2A shows an example of portions of the system, with portions of a particular illustrative example of an external (or partially or fully subcutaneously insertable or implantable) interface unit shown in more detail.

FIG. 2A shows an example of portions of the system 10, with portions of a particular illustrative example of an external (or partially or fully subcutaneously insertable or implantable) interface unit 15 shown in more detail. In FIG. 2A, the proximal port 106 can be coupled via the fluid coupler 108 to a pump output fluid flow path of an infusion pump 206. An input port of the pump 206 can be coupled via a fluid flow path to a reservoir 204, which can be loaded with a drug or other fluid to be infused via the catheter 100 into the subject at the distal port 104 of the catheter 100. Either of the pump 206 or the reservoir 204 can be integrated into a single external interface unit 15, or can be separate components that can be coupled to and controlled by the external interface unit 15. One or more components of the external interface unit 15 can alternatively be integrated with the catheter 100, optionally in such a manner as to permit such one or more components of the external interface unit 15 to be insertable or implantable into the subject, if desired.

Electrical interface circuitry 208 can be included in the external interface unit 15, with a catheter electrical interface bus 212 coupled to an appropriate electrical connector at a proximal end of the catheter 100, such as to establish one or more electrical interconnections with the catheter. The electrical connector can be integrated with the fluid coupler 108, such as shown in the example of FIG. 2. Controller circuitry 202 can be coupled via a control bus 210 to the pump 206 and the electrical interface circuitry 208, such as for control of each, individually or in concert, such as explained further herein. The controller circuitry 202 can include one or more general purpose microcontrollers, or the like, and can include integrated or separate general purpose or dedicated circuitry such as flow controller circuitry 214, sensor interface and control circuitry 216, piezoelectric or other electromechanical control circuitry 218, heating/RF controller circuitry 220, and sweep/addressing controller circuitry 222. Such components within the controller circuitry 202 can be implemented using stored instructions that can be interpretable or executable to convert a general-purpose microcontroller into one or more of the dedicated circuitry components shown. As explained further herein, the controller circuitry can use feedback from one or more temperature sensors to control addressing and activation of one or more local heat sources, such as using the "sweep" control techniques described herein.

Figure 2B:
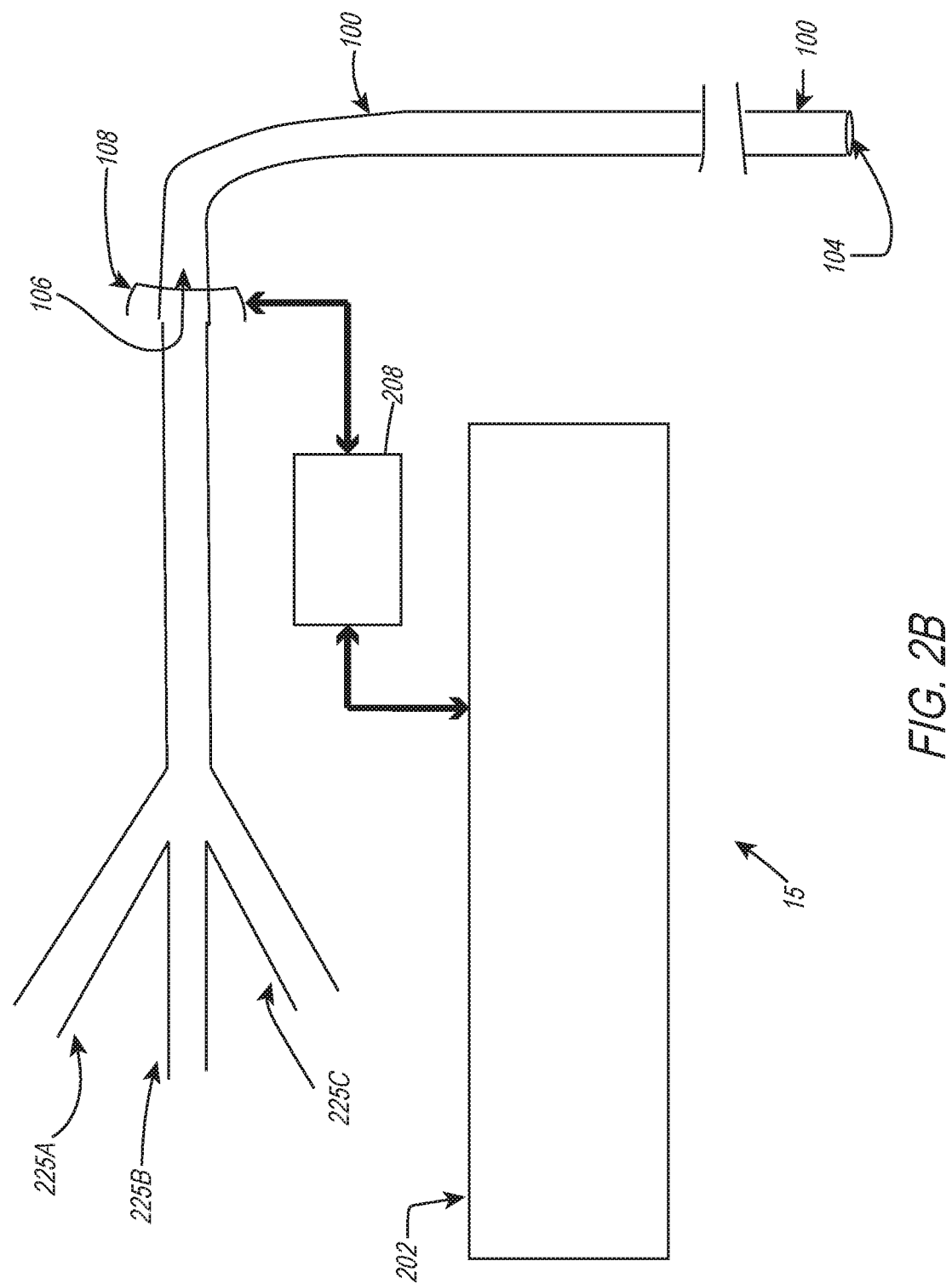
FIG. 2B illustrates an example in which an infusion pump is not required.

FIG. 2B illustrates an example in which an infusion pump is not required; additionally or alternatively, one or more infusion ports 225A, 225B, 225C can be provided, such as at the external interface unit 15, such as to allow a clinician or other user to use a syringe or other device to inject a fluid, via an infusion port 225, into a proximal end port 106 of the catheter 100 for delivery to the subject via the distal port 104 of the catheter 100.

Although the control unit 15 may be external, such as explained with respect to FIGS. 2A-2B, all or portions of the control unit 15 may be subcutaneously implantable. The control unit 15 may optionally be remotely powered by wired or wireless (e.g., RF or inductive) power transfer.

Figure 3A:
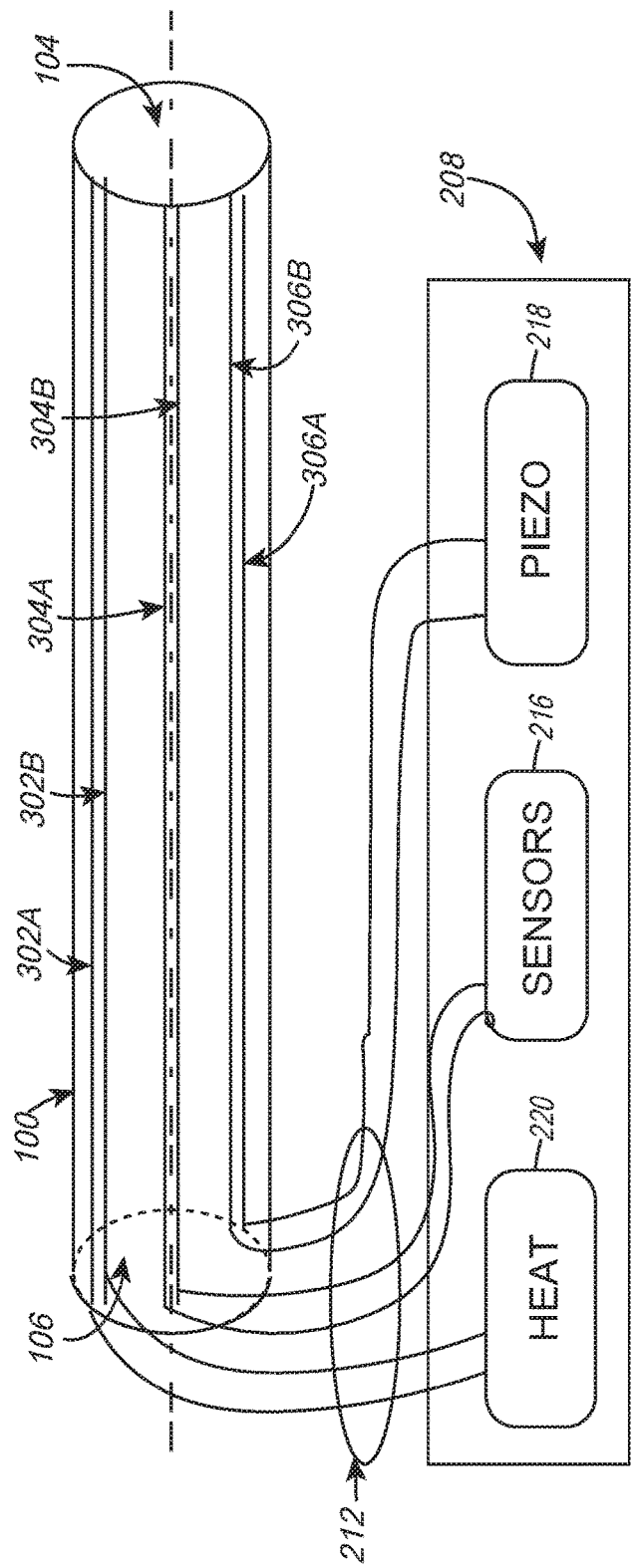
FIG. 3A shows a schematic example of electrical coupling and layout.

FIG. 3A shows a schematic example of electrical coupling and layout, such as from the electrical interface circuitry 208, via the electrical signal bus 212 to electrical connections on a proximal end of the catheter 100. One or more heating/RF control signals from the heating/RF control circuitry 220 can be coupled to corresponding first and second (e.g., $(V_+, V_-)$, $(V_+, V_0)$, $(V_-, V_0)$) heating RF electrical input control lines 302A-B extending longitudinally toward the distal end of the catheter 100, such as terminating at RF electrode traces or one or more other heat sources. First and second (e.g., $(V_+, V_-)$, $(V_+, V_0)$, $(V_-, V_0)$) temperature sensor signal lines 304A-B from one or more temperature sensors located on the catheter 100, such as toward its distal end (e.g., near one or more heat sources), can extend longitudinally back to the sensor interface and control circuitry 216, such as via the electrical interface circuitry 218. Piezo-electromechanical control signals from the piezo-electromechanical control circuitry 218 can be coupled to first and second (e.g., $(V_+, V_-)$, $(V_+, V_0)$, $(V_-, V_0)$) piezo-electromechanical control lines 306A-B extending longitudinally toward the distal end of the catheter 100, terminating at piezoelectric transducers, such as can provide vibration or other electromechanical actuation at a desired location of the catheter 100. Thus, FIG. 3A shows an illustrative example in which six electrical lines can be used to provide RF heating control, temperature sensing, and electromechanical actuation.

Figure 3B:
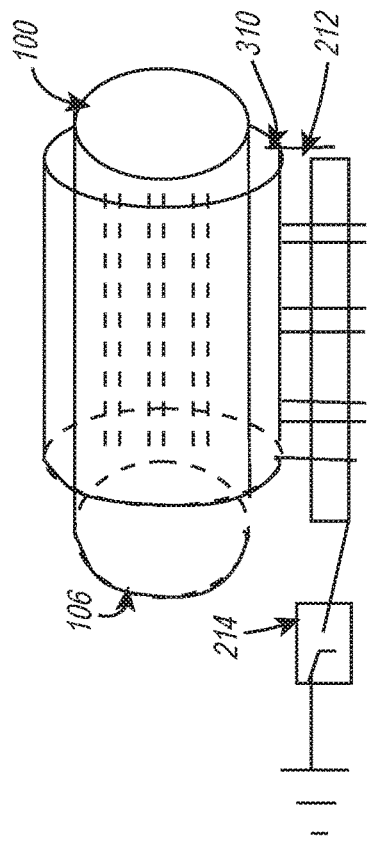
FIG. 3B shows an example of a proximal end connector to the catheter.

FIG. 3B shows an example of an electrical connector 310, such as can be placed over or about a proximal end of the catheter 100, such as can be arranged to permit an aligned electrical connection between the conductors of the bus 212 and the conductors 302A-B, 304A-B, and 306A-B on the catheter 100. In FIG. 3B, such electrical connections can be circumferentially spaced or distributed about the interior of the electrical connector 310 and correspondingly arranged contacting electrical connection locations about the exterior of the catheter 100. Additionally or alternatively, a wireless connection can be provided between the external interface unit 15 and the catheter 100, such as can use inductive coupling for wireless signal communication. A grounding switch 214 can be included, such as can short the conductors of the bus 212 to a ground node in an MRI mode when the subject in which the catheter 100 is at least partially implanted or inserted is to undergo an MRI scan.

FIGS. 4A, 4B, 4C, and 4D show illustrative examples of a distal portion of a medical device such as a tubular catheter 100 having a longitudinally extending passage or lumen such as for allowing passage therethrough of a drug, or of a biological fluid, such as blood, urine, cerebrospinal fluid, or the like, or other fluid or flowable substance, such as having a gel-like consistency, a paste-like consistency, or the like. A distal end of the catheter 100 can reside in vivo, such as within a blood vessel, a bladder, gastrointestinal (GI) tract, an interparenchymal space, or the like, such as can involve the distal end being exposed to biological fluid such as blood, urine, cerebrospinal fluid, or the like.

FIG. 4A (side cross-sectional view) and FIG. 4B (distal end cross-sectional view, looking proximally) show an example of a conical or other tapered distal tip portion 402, such as having a length L, of the catheter 100, such as can be useful, in an illustrative non-limiting example, in a urinary application, such as explained above with respect to FIG. 1B.

FIG. 4C (side cross-sectional view) and FIG. 4D (distal end cross-sectional view, looking proximally) show an example of a cylindrical, e.g., non-tapered distal tip portion 403, such as having a length L, of the catheter 100. FIG. 4B shows examples of various outer radii, r2, r2' and inner radii, r1, r1', which become incrementally smaller in a direction approaching the distal tip. FIG. 4D shows examples of an outer radius, r2, and an inner radius r1 for the cylindrical tip portion 403 of the catheter 100.

Figure 5A:
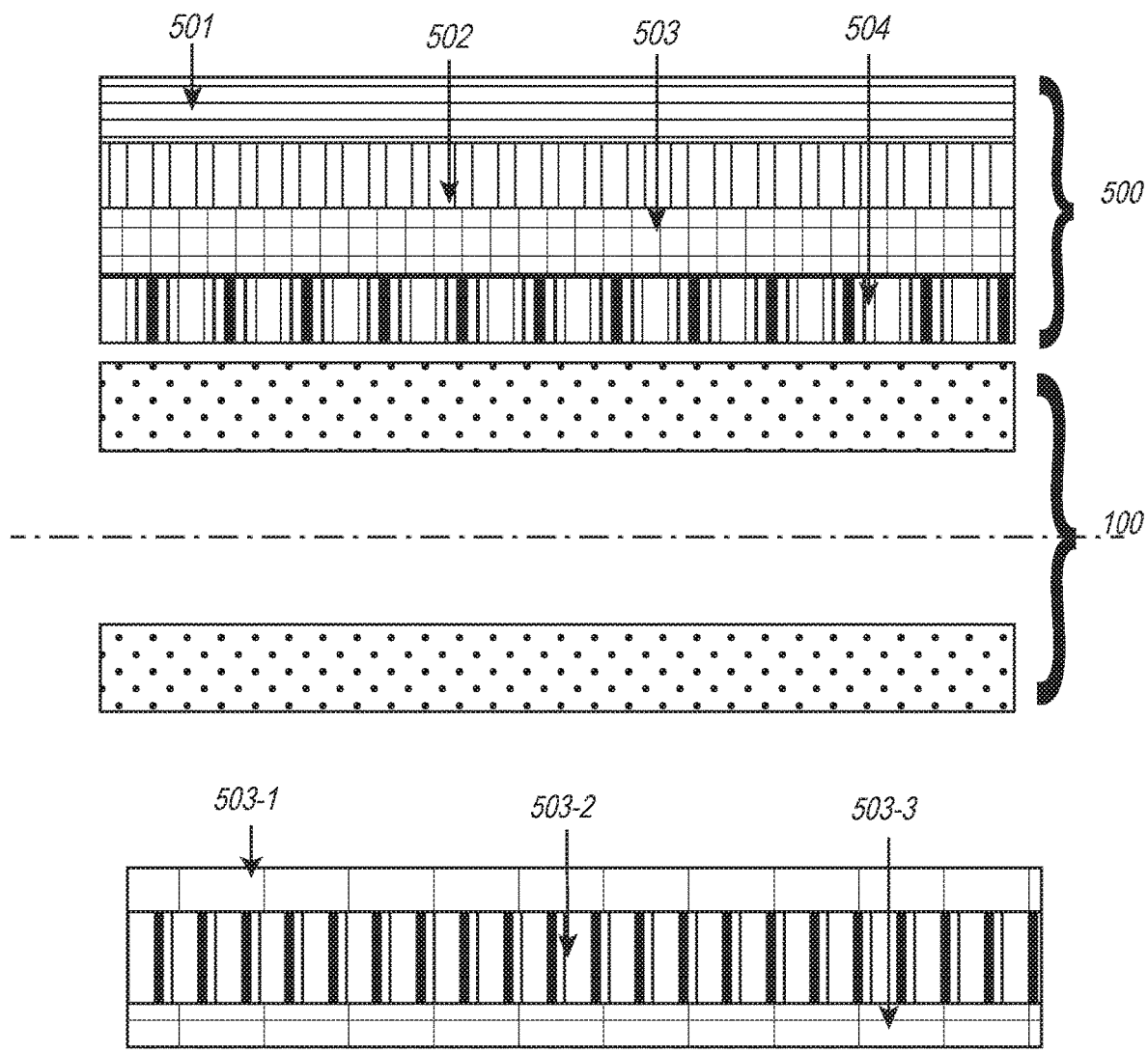
FIGS. 5A, 5B, 5C, 5B, 5E, 5F, 5G, 5H, 5I, 5J, 5K show examples of various layers that can be used to implement various structures, such as can be included in or on a catheter or other medical device.

FIG. 5A (cross-sectional side view; proportions not drawn to scale) shows an illustrative example of a cylindrical tip portion 403 of a catheter 100, such as can provide an outer cylindrical surface upon which an active thermal heating device 500 can be formed. In an example, the thermal heating device 500 can include multiple layers, arranged such as shown in FIG. 5A, or with one or more specialized layers arranged differently to provide design flexibility to suit a particular application or use case; the sequence of layers shown in various figures herein are illustrative examples only, and are not intended to be limiting; such layers can be used in various other sequences or combinations. For example, an adhesion or base layer 504 can be formed upon the outer cylindrical surface of the catheter 100, such as to adhere and fasten the thermal heating device 500 to the outer cylindrical surface of the catheter 100, with which the adhesion or base layer 504 can make direct contact. In an example, a region of the outer surface of the catheter 100 can optionally be skived or otherwise shaped or formed to provide a flat region, such as can help permit easier adhesion of the thermal heating device 500 thereto, however, this is not required.

Above and upon the adhesion layer 504, the thermal heating device 500 can include an electrode or power layer 503. The power layer 503 can include therewithin one or more selectively-patterned electrodes (or planar resonators, strip-lines, or the like, such as described herein), such as for respectively receiving an electrical input signal from the V+, V− heating/RF control lines 302A-B (FIG. 3A) for conversion into thermal energy in an adjacent active substrate layer. The electrical input signal delivered to the electrodes in the power layer 503 can be used to create a physical phenomenon in the active substrate layer to create heat in the active substrate layer. It can be desirable to keep the electrode or power layer 503 immediately adjacent to the active substrate, such as for efficient coupling and heat generation and finer frequency-control. Thus, the electrodes in the electrode or power layer 503 can be formed directly on the adjacent active substrate layer, or separated therefrom by a thin capacitive dielectric layer, if a capacitive coupling to the active substrate is desired.

The one or more patterned electrodes (or planar transmission line resonators ("planar resonators"), strip-lines, or the like, such as described herein) within the electrode or power layer 503 can be arranged into one or more specific geometries or one or more particular arrangements, such as to act as a receiver for RF, AC, or other form of energy, such as from the V+, V− heating/RF control lines 302A-B (FIG. 3A). The frequency of control signals on the V+, V− heating/RF control lines 302A-B can be adjusted or tuned, such as to allow frequency control to select a particular location or region on the electrode geometry or arrangement at which the input signal energy is focused for generating thermal energy in an adjacent layer. The electrode layer 503 can optionally include one or more dielectric layers 503-1, 503-3, such as above and adjacent to a primary electrode layer 503-2, or below and adjacent to the primary electrode layer 503-2. One or more electrodes can be selectively patterned within the primary electrode layer 503-2. One or more of the dielectric layers 503-1, 503-3 can allow capacitive coupling to an adjacent layer.

Above and directly or indirectly upon the electrode or power layer 503, the thermal heating device 500 can include an active substrate layer 502, such as for example a semiconductor or a lossy or dissipative dielectric, which is capable of being acted upon by electrodes patterned in the electrode layer 503. Electrodes patterned in the electrode layer 503 can capacitively couple or otherwise act upon the active substrate layer 502 such as to generate heat in the substrate layer 502, such as based on or in response to an AC electrical signal applied to or between one or more individual electrodes in the electrode or power layer 503.

A number of materials can be suitable for serving as the active substrate in which a heat source can be dynamically created such as by frequency-controlled actuation by providing an electromagnetic input signal to adjacent or nearby electrodes, a planar resonator, strip-line, or a similar structure. As mentioned above, a semiconductor or a lossy dielectric can serve as an active substrate for such heat generation, as can a crystalline (e.g., single crystalline or polycrystalline) lattice structure such as, e.g., a single crystal diamond lattice. An electrically highly conductive metal material or a non-conductive dielectric material generally would not allow conductivity management in such a substrate via an electromagnetic input signal provided to adjacent or nearby electrodes, planar resonator, strip-line or similar structure and, therefore, would not be as suitable candidates for an active substrate as compared to a semiconductor or a lossy dielectric, in which the conductivity can be so managed. However, a polymeric plastic substrate material that does allow such conductivity management of the substrate may be a suitable active substrate material.

One example of a characteristic parameter of an active substrate is "tan delta", or tan ($\delta$), which is a function of: (1) frequency (f) of the electrical input signal applied to the adjacent or nearby electrodes, planar resonator, strip-line, or similar structure; (2) electrical conductivity ($\sigma$) of the substrate material; and (3) permittivity ($\epsilon$) of the substrate material. In an example, candidate substrate materials with tan ($\delta$) in the range of $10^{-2}$ to $10^2$ are acceptable active substrate materials for dynamic heat source creation such as described herein. For example, U.S. Pat. No. 9,536,758, incorporated herein by reference, describes an example using silicon as a semiconductor active substrate, such as with a corresponding tan ($\delta$) of ($1.546*10^{-2}$), as an illustrative, non-limiting example. In general, ($\sigma<\omega\epsilon$) are lossy dielectrics suitable as an active substrate material, ($\sigma<<\omega\epsilon$) are good insulators and are a less suitable choice as an active substrate material, ($\sigma>\omega\epsilon$) are again lossy dielectrics suitable as active substrate materials, and ($\sigma>>\omega\epsilon$) are good conductors and are a less suitable choice as active substrate materials.

An active substrate can be selected based on, for example, a desired operating frequency, an electrical conductivity of the active substrate material, and a permittivity of the active substrate material. For example, for any given candidate substrate material having an electrical conductivity value or range of values, a table of possible tan ($\delta$) values can be created for a given range of input electrical signal frequency values, such as can help in selecting the desired pair of values corresponding to substrate conductivity and electrical input signal frequency.

Above the substrate layer 502, the thermal heating device 500 can include a biocompatible encapsulating sealing or sealant layer 501. Such a biocompatible sealant layer 501 can be hemocompatible, such as can help avoid thrombogenesis when the portion of the catheter 100 including the thermal heating device 200 is placed within a blood vessel. In an example, such a biocompatible sealant layer 501 can also provide an adhesion layer, such as for promoting tissue ingrowth or adhesion to an organ or tissue in vivo.

Figure 5B:
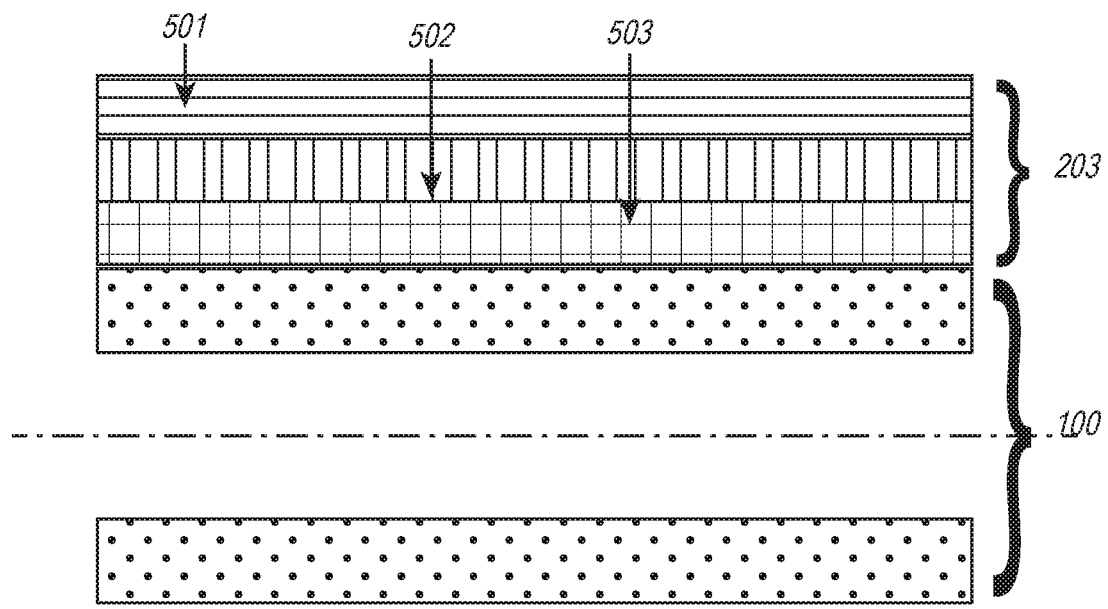

FIG. 5B (cross-sectional side view) shows an illustrative example of a portion of the catheter 100 without requiring the adhesion layer 504. In this example, the electrode layer 503 can be placed directly or indirectly on outer circumferential wall of the catheter 100. For example, thermal (heat) bonding can be used instead of requiring an adhesion layer 504. An active substrate layer 502, which can be used to generate heat, can be formed directly or indirectly upon the electrode layer 503. A biocompatible sealant layer 501 can be formed directly or indirectly upon the active substrate layer 502.

In an example, within the electrode layer 503, the electrodes need not occupy all the area within the electrode layer 503. Instead, such electrodes can provide a selectively-patterned or other distinct arrangement of one or multiple electrodes, such as can be separated from each other, within the electrode layer 503, by an insulator. Within the electrode layer 503, one or more temperature sensors can also be located, such as with a temperature sensor between two electrodes. The sensor can be approximately the same height as the electrodes between which it is placed.

Figure 5C:
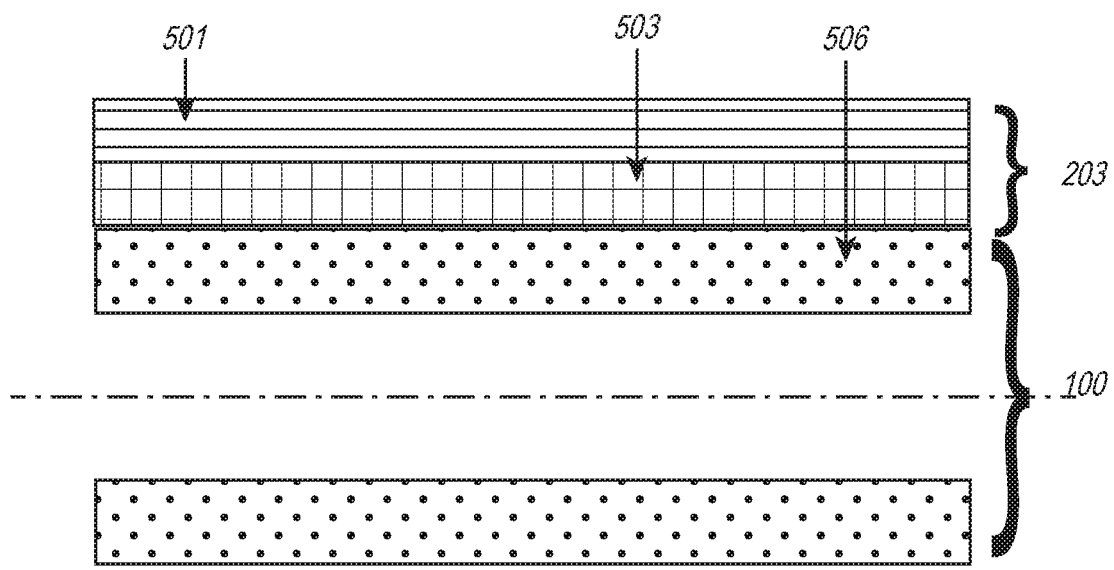

FIG. 5C (cross-sectional side view) shows an illustrative example in which the catheter wall 506 of the catheter 100 can act as an active heating substrate layer, such as in addition or as an alternative to the substrate layer 502. In such an example, the catheter wall 506 can include an electrically and thermally conductive plastic or other material. The electrical conduction characteristics of the catheter wall 506 can be selected for the specific application or intended use of the catheter 100. In an example, the electrode layer 503 can be placed directly or indirectly upon an outer circumferential surface of the catheter wall 506. The sealant layer 501 can be formed directly or indirectly upon the electrode layer 503; the active substrate layer 502 can be omitted, as shown, or can optionally be included, such as between the electrode layer 503 and the sealant layer 501 shown. Such an arrangement does not preclude use of other layers, such as described herein. Instead, FIG. 5C is intended to represent an instance in which the body of the catheter 100 can be used as the active heat-generating substrate.

Figure 5D:
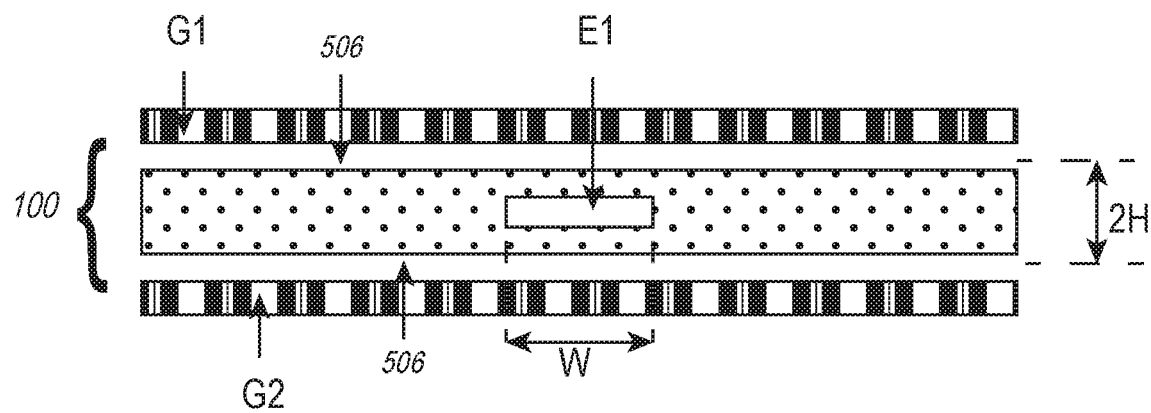
Figure 5E:
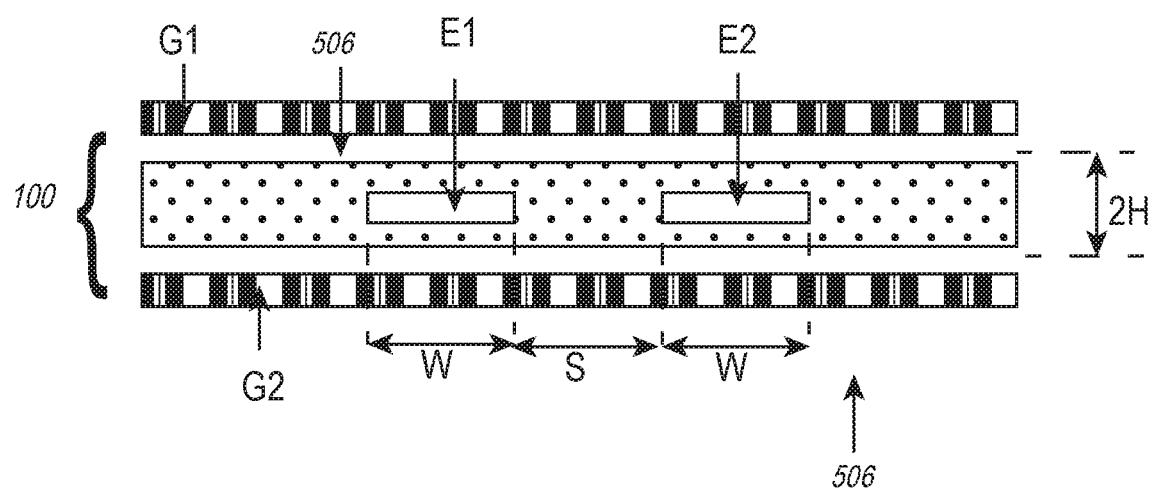

FIG. 5D (cross-sectional side view, one electrode) and FIG. 5E (cross-sectional side view, two electrodes) show strip-line configurations examples in which the active semiconductor or other substrate layer 502 can provide heating under control of one electrically conductive electrode E1 (FIG. 5D) or two electrically conductive electrodes E1, E2 (FIG. 5E), such as in conjunction with the electrically conductive ground planes G1, G2. In an example, the tubular catheter wall 506 itself can form the electrically and thermally conductive active substrate layer 502, such as with electrically conductive ground planes G1, G2 formed directly or indirectly thereupon, such as on exterior and interior surfaces of the catheter 100, separated by the catheter wall thickness (2H) of the catheter 100. In this example the electrodes E1, E2 can be placed equidistant from the ground planes G1, G2 each at a distance H thus the total thickness is 2H. The electrodes E1 and E2 can be located within the substrate layer 502, such as within the tubular catheter wall 506 itself, such as at a distance H from the exterior and interior surfaces of the catheter wall 506 or from each surface of the substrate layer 502. Thus, in this example or in certain other examples, no separate electrode layer 503 is needed—for example, the electrodes E1, E2 can be embedded within the substrate layer 502, which may be separate from or integrated together with the catheter wall 506. The electrodes E1, E2 can have a width, W, and in the case of two electrodes E1, E2, can be spaced a part by a distance S, such as shown in FIG. 5E. Alternatively, a microstrip-line configuration using a single electrically conductive ground plane G1 can be used.

Figure 5F:
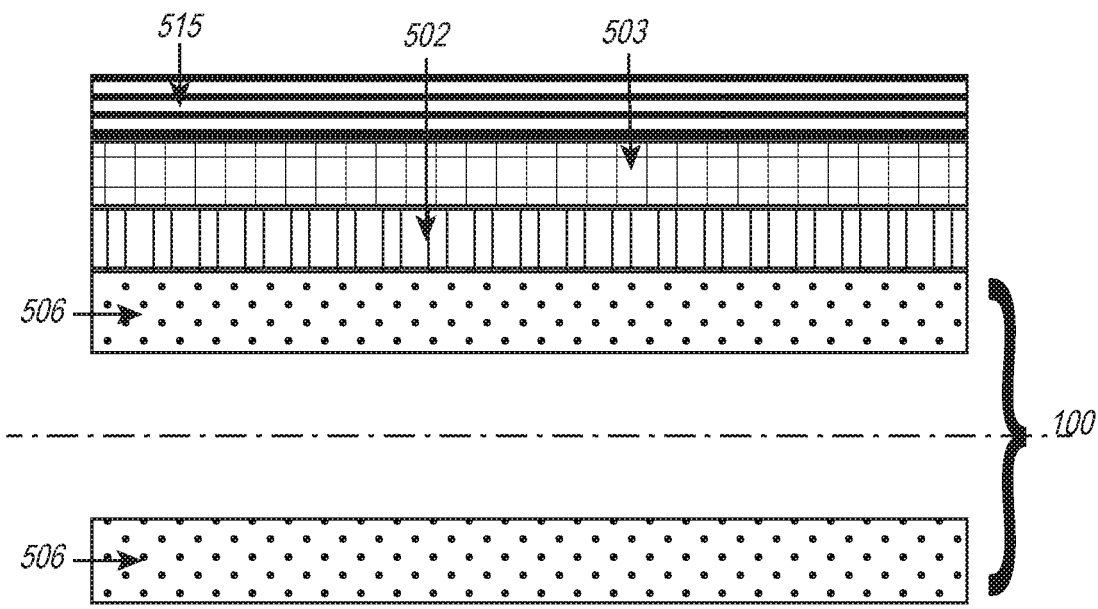
Figure 5G:
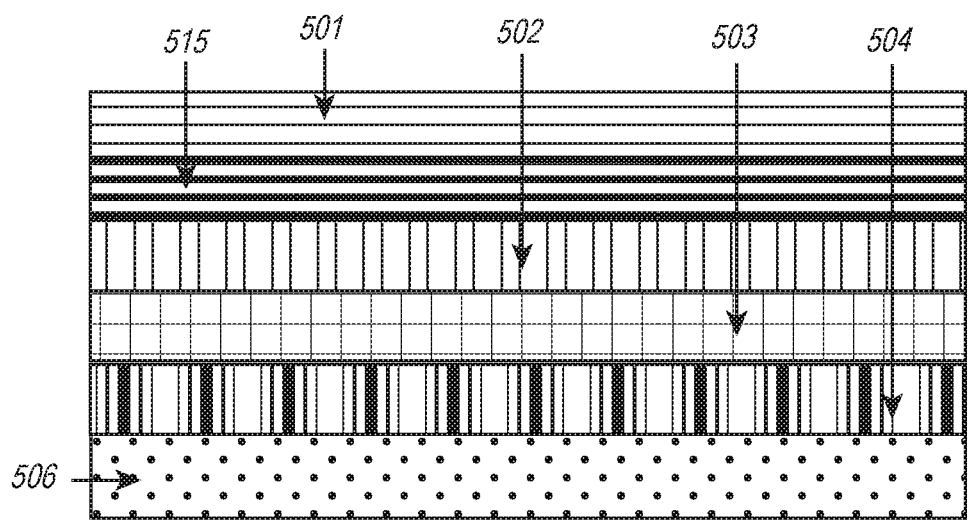

FIG. 5F (cross-sectional side view) shows an illustrative example in which a sensing or sensory layer 515 can be included upon the thermal heating device 500. FIG. 5G (cross-sectional side view) shows an illustrative example in which the sensory layer 515 can be included within the thermal heating device 500, such as within or right below the biocompatible sealant layer 201 of the thermal heating device. The sensory layer 515 can include one or more temperature sensors and related interconnection structures. The sensory layer 515 can be located close to or even in direct contact with the external or internal locations of contact between the body of the catheter 100 and any nearby or surrounding bodily fluid, tissue, or other in-vivo structures of the subject. Such placement or location of the sensory layer 515 can help obtain accurate and near-instantaneous sensed temperature measures, such as can be used for active feedback control of the heating device 500.

In FIG. 5F, the active substrate layer 502 can be located on an outer circumferential periphery of the catheter wall 506 of the catheter 100, such as with the electrode layer 503 located directly or indirectly thereupon. A sealant layer 501 can optionally be included, such as can be located upon the electrode layer 503. However, this is not required. The sensory layer 515 can be located directly or indirectly upon the electrode layer 503, such as optionally upon the sealant layer 501.

FIG. 5G (cross-sectional side view) shows an illustrative example in which the temperature-sensing or other sensory layer 515 can be integrated with or interlaced within the sealant layer 501. In FIG. 5G, an adhesion layer 504 can be located on an outer circumferential periphery of the catheter wall 506 of the catheter 100, such as with an electrode layer 503 located directly or indirectly thereupon. An active semiconductor or other substrate layer 502 can be located directly or indirectly upon the electrode layer 503. The sensory layer 515 can be located directly or indirectly upon the active substrate layer 502, such as encapsulated under a biocompatible sealant layer 501. The approach shown in FIG. 5C can potentially help ease of fabrication, since both sensing and heating functions can include respective layers within the sealant layer 501, such as can allow combined placement of both in a single step, rather than involving two separate or independent fabrication steps.

Figure 5H:
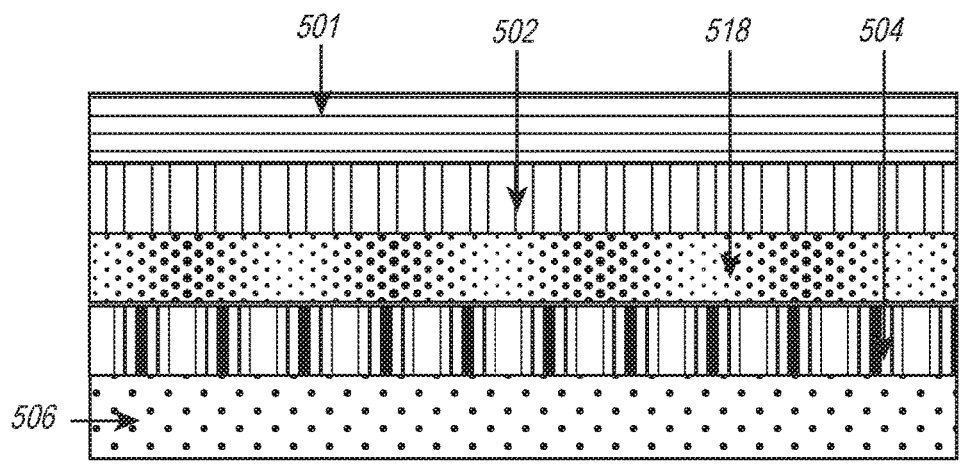

FIG. 5H (cross-sectional side view) shows an illustrative example in which the temperature-sensing or other sensory layer 518 can be integrated with the electrode layer 503. In FIG. 5H, an adhesion layer 504 can be located on an outer circumferential periphery of the catheter wall 506 of the catheter 100, such as with an integrated electrode and sensory layer 518 located directly or indirectly thereupon. An active semiconductor or other substrate layer 502 can be located directly or indirectly upon the integrated electrode and sensory layer 518. An encapsulating biocompatible sealant layer 501 can be located directly or indirectly upon the active substrate layer 502.

Figure 5I:
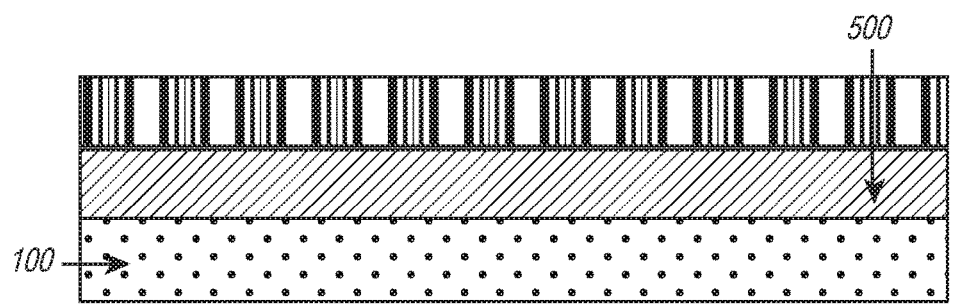
Figure 5J:
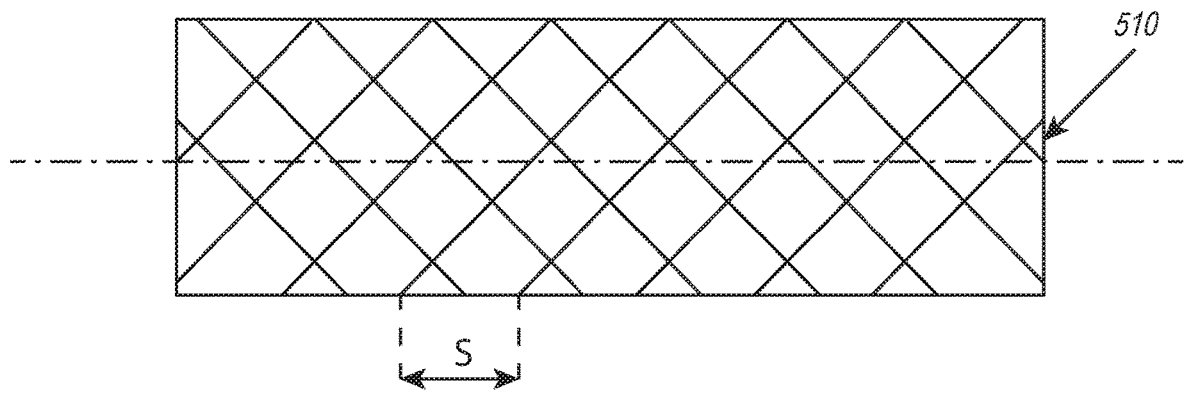

FIG. 5I (cross-sectional side view) and FIG. 5J (top view) shows an illustrative example in which an optional mesh or other radiofrequency (RF) shielding layer 510 can be included, such as to help inhibit or prevent energy of the RF signal used for heating the active semiconductor or other layer from radiating outward beyond the shielding layer 510 into the subject. The mesh shielding 510 can include strands, and the spacing between the strands can be specified to inhibit leakage of RF energy at the frequencies used for heating the desired regions of the catheter 100 to inhibit or neutralize biofilm. The mesh shielding layer 510 can be embedded within the sealant layer 501, or the mesh shielding layer 510 can be a separate layer such as can be overlaid and encapsulated by the sealant layer 501.

Figure 5K:
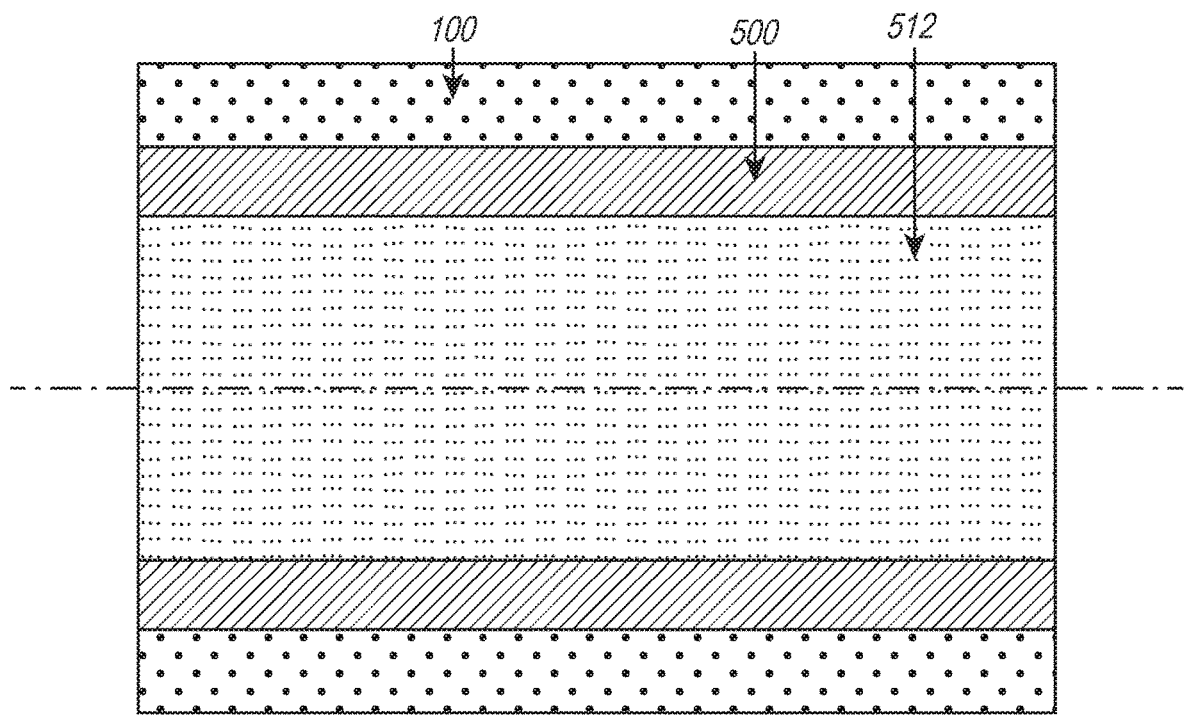

FIG. 5K shows an example in which the various layers associated with the heating device 500 can be additionally or alternatively located against an interior wall of the catheter 100. The closest layer (e.g., the sealant layer 501) to a central longitudinal axis of the catheter can define a wall of at least a portion of a lumen 512 or passage of the catheter 100, such as to provide heat to inhibit, disrupt, or neutralize biofilm within such lumen 512 or passage of the catheter 100. In the case of such lumen 512 carrying a fluid (e.g., saline) to be flushed or otherwise conducted out from the catheter 100 and into the subject, temperature sensing within the lumen 512 (e.g., such as explained herein) can provide temperature information about such fluid to an external user interface, which can allow monitoring or alerting to that flushing can be carried out when such fluid is at an appropriate temperature. The fluid within the lumen 512 can be accounted for and its heat retention can be used such as can help sterilize or otherwise inhibit biofilm within the lumen 512.

Some Examples of Electrode Configurations for Controlling Heating

Various arrangements of electrically conductive electrodes can be used for controlling heating in an adjacent or nearby active substrate. For example, a co-planar arrangement of electrodes can lie within the same plane or surface (e.g., a cylindrical surface can be regarded as cylindrically co-planar), which can be upon, adjacent, or nearby to an active substrate, without requiring an accompanying electrically conductive ground plane. In an example, a strip-line arrangement of electrodes can be configured such that at least one electrode can be located or embedded within an active substrate and sandwiched between two ground planes that can respectively be located above and below the active substrate in which the at least one electrode is located or embedded. Thus, in a stripline arrangement these ground planes can be respectively located above and below the at least one electrode that is located or embedded in the active substrate. A micro-stripline arrangement can be similar to a strip-line arrangement, but the micro-stripline arrangement need only include a single ground plane that can be located one of above or below the plane of the active substrate in which the at least one electrode is located or embedded. Thus, the ground plane in the micro-stripline arrangement can be located one of above or below the at least one electrode that is located or embedded in the active substrate. A coplanar wave guide can include at least one electrode such as can be located in the same plane or surface with accompanying electrically ground strips running alongside the electrode, such as upon or near a conformal plane of the active substrate material, with the electrode located between the ground strips and separated therefrom by air or a dielectric.

FIG. 6A (flattened planarized view) and FIG. 6B (side view as applied to a circumference of cylindrical catheter 100 having an outer radius r) show an illustrative example of a possible cylindrically "coplanar" arrangement of electrodes 600A-B for use in providing selectively localized heating of the catheter 100, such as within a region defining a heating device 500. In the flattened planarized view of FIG. 6A, the circumferential distance M around the outer wall 506 of the catheter 100 is equal to twice the product of its radius r with the constant pi, that is: $M=2 \cdot \pi \cdot r$. The length L can represent the length of the region defining at least a portion of the heating device 500 associated with a portion of the catheter 100. The electrodes 600A-B can be selectively patterned or otherwise formed within an electrode layer 503 and can be separated from each other within the electrode layer 503 by an insulating region, such as explained herein.

In FIG. 6A, the electrodes 600A, 600B can be arranged with respect to a longitudinal axis 602 defined by the catheter 100 such that a separation between the electrodes 600A-B can undergo a continuous monotonic decrease in a longitudinal direction that is one of toward or away from a distal tip of the catheter 100. Stepwise decreases in separation may lead to reflection in the electrical signal being placed upon the electrodes 600A-B. If the change in separation (stepwise or otherwise) between electrodes is gradual enough, that will present a small change in inductance, which, in turn, can help to reduce reflection, if desired.

In this way, a unique minimum separation S exists from a given location along a length of one of the electrodes 600A, 600B to the closest location on the other of the electrodes 600A, 600B. A particular location in the active substrate along one of the electrodes 600A, 600B for depositing heat (e.g., for depositing more heat than at other locations in the active substrate along that one of the electrodes 600A, 600B) can be selected by tuning the frequency of an applied electrical signal delivered via the signal lines 302A-B (FIG. 3) to corresponding electrodes 600A-B, respectively individually coupled thereto, such as explained in detail herein.

For example, the frequency of an applied electrical signal delivered via the signal lines 302A-B to the respective electrodes 600A, 600B can be tuned to use this variable minimum separation S between the electrodes 600A-B to select a location along the longitudinal direction of the catheter 100 at which heat can be generated in the adjacent active substrate layer 202, such as similarly explained in the above-incorporated U.S. Pat. No. 9,536,758. More than one such pair of electrodes 600A-B can be provided on the catheter 100, for example, such as a separate second pair of electrodes 300C, 300D located on or above an opposing outer surface of the catheter 100, such as shown in FIG. 6C (flattened planarized view). Separate electrical control signals can be delivered to the separate pairs of electrodes 600A-B and 600C-D, such as via independent electrically conductive signal lines 302A-B and a further pair of electrically conductive signal lines that can extend along the length of the catheter 100 to make an electrical connection to a location outside of the patient's body, such as for receiving corresponding electrical connections to an electrical signal generator such as can be included within the heating/RF control circuitry 220 (FIG. 2).

Figure 6D:
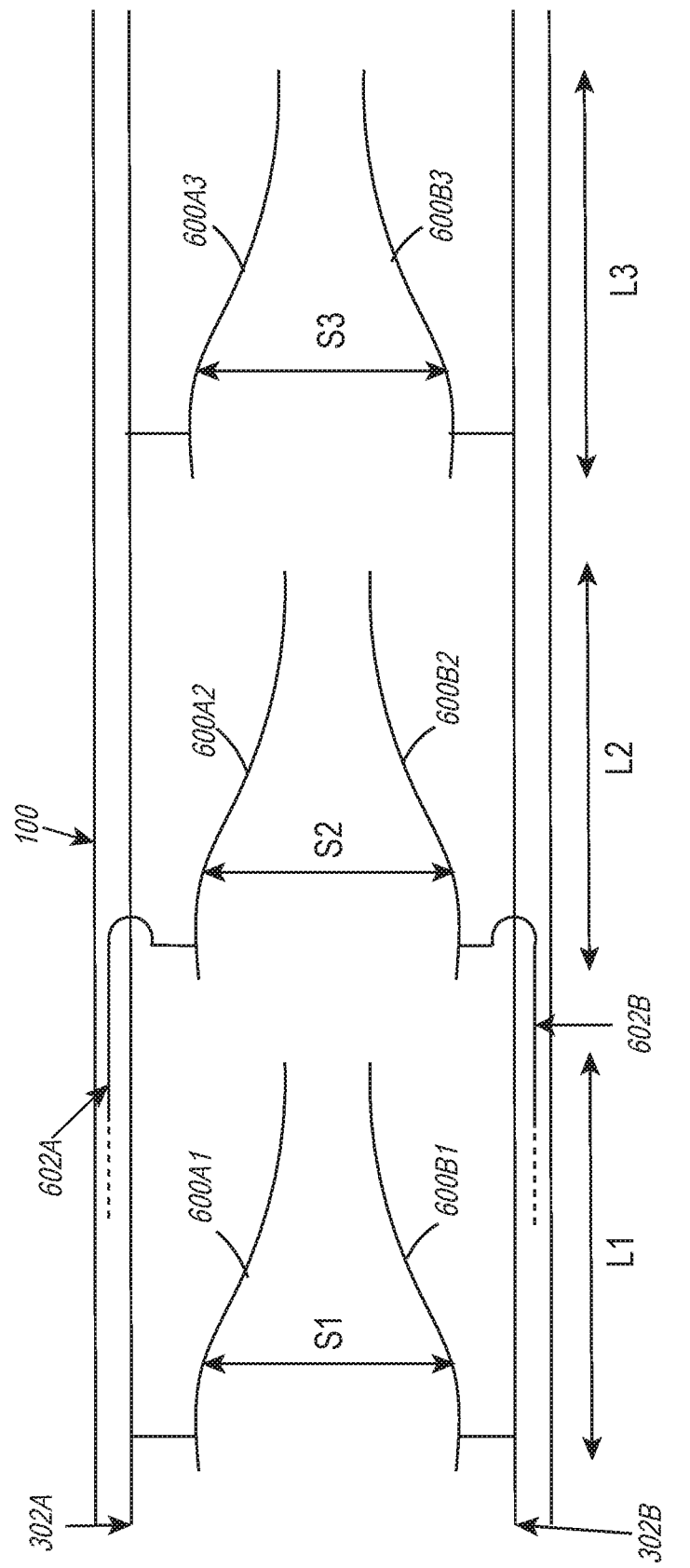
FIG. 6D (flattened planarized view, similar to FIG. 6A) shows an example of a planar resonator in which electrodes, with variable minimum separation therebetween at longitudinally different locations along the length L, can be instantiated repeatedly at desired longitudinal locations along the length L of the catheter.

FIG. 6D (flattened planarized view, similar to FIG. 6A) shows an example of a planar resonator in which electrodes 600A, 600B, with variable minimum separation therebetween at longitudinally different locations along the length L, can be instantiated repeatedly at desired longitudinal locations along the length L of the catheter 100. The electrically conductive signal lines 302A-B can be arranged to selectively connect to one or more desired pairs of electrodes 600A-B, other pairs of electrodes 600A-B can optionally be left unconnected from the electrically conductive signal lines 302A-B, if desired. For example, as shown in FIG. 6D, the electrically conductive signal lines 302A-B can be electrically connected to electrode pairs $600A_1$-$B_1$ and $600A_3$-$B_3$, but are optionally left unconnected to electrode pair $600A_2$-$B_2$. In this example, a frequency selected to generate heat at $S_1$ of electrode pair $600A_1$-$B_1$ will also generate heat at $S_3$ ($S_3$=$S_1$) of electrode pair $600A_3$-$B_3$, but will not generate heat at $S_2$ ($S_2$=$S_1$) of electrode pair $600A_2$-$B_2$, which is left unconnected to the electrically conductive signal lines 302A-B. Instead, electrode pair $600A_2$-$B_2$ can optionally be electrically connected to separate electrically conductive signal lines 602A-B, along with any desired number of other electrode pairs that are desired to be physically addressed separately, rather than requiring all electrode pairs to be addressed by a common frequency controlled electrical signal that is shared by all electrode pairs.

It should be noted that the electrically conductive signal lines 302A-B need not form a closed circuit on the catheter 100, either at its proximal end or at its distal end. Instead, the electrically conductive signal lines 302A-B need only to respectively connect to respective electrodes 600A-B. This means that the catheter 100 can be cut (e.g., by a user) to an appropriate desired length, without affecting the functionality of the electrically conductive signal lines 302A-B and the respective electrodes 600A-B remaining on the catheter 100 without having been cut away (e.g., by the user). This can be important in a use case in which the user desires to cut the catheter 100 to a desired length, such as to adapt the catheter to a particular subject's body anatomy, insertion depth and location, or the like. Cutting the catheter 100 to the desired length need not affect the heating functionality that can be provided such as described herein.

FIGS. 6A, 6B, 6C, 6D illustrate examples in which electrodes 600A-B can be arranged along the catheter 100 such that an interelectrode spacing S varies longitudinally along a length L that forms a portion of the aggregate length of the catheter. However, pairs of electrodes can additionally or alternatively be arranged along the catheter such that an interelectrode spacing S varies circumferentially about a circumference or periphery of the catheter.

Figure 6E:
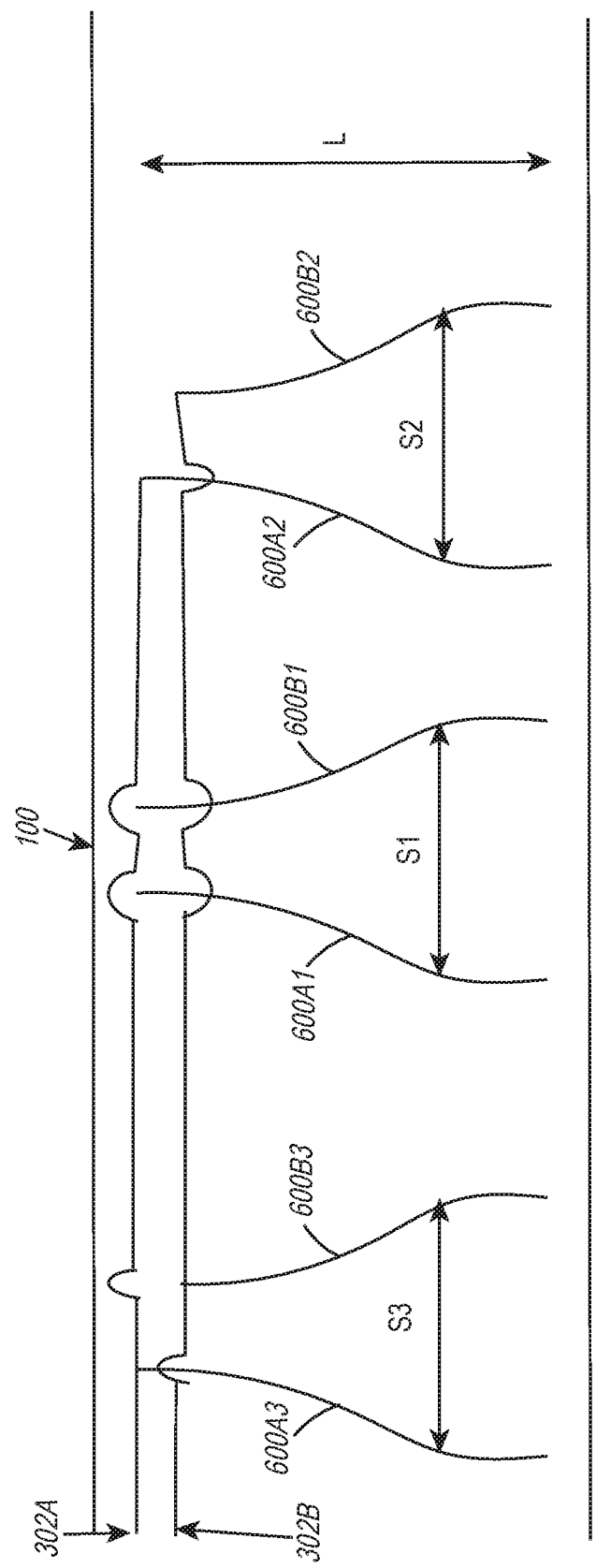
FIG. 6E (flattened planarized view) illustrates an example in which the electrode pairs are instead oriented along the catheter such that an interelectrode spacing S varies circumferentially about a circumference or periphery of the catheter.

FIG. 6E (flattened planarized view) illustrates an example in which the electrode pairs are instead oriented along the catheter 100 such that an interelectrode spacing S varies circumferentially about a circumference or periphery of the catheter 100. In this case, all electrically interconnected electrode pairs can concurrently generate heat in the adjacent active substrate at their respective longitudinal locations on the catheter 100, and the specific circumferential active substrate heat generation location about the catheter 100 can be controlled using the frequency of the applied electrical signal. One or more pairs of the electrodes, e.g., electrode pair $600A_2$-$B_2$, can be separately physically addressed by a pair of separate longitudinal electrical traces that can be electrically interconnected thereto.

FIG. 6F (side view) illustrates an example in which pairs of electrodes can additionally or alternatively be arranged along the catheter such that an interelectrode spacing S varies circumferentially about a circumference or periphery of the catheter, but in which separate pairs of electrodes can be provided on opposing sides of the catheter. In FIG. 6F, electrode pairs on the back-side of the catheter 100 are indicated with dashed lines and electrode pairs on the front-side of the catheter 100 are indicated with solid lines. Such an arrangement can be used to obtain heating that can be segmented into two parts circumferentially. Shared or separate electrically conductive signal lines 302A-B can be used to access pairs of electrodes that are similarly longitudinally situated along the length of the catheter 100, but that are on opposing sides of the catheter 100, such as illustrated in FIG. 6F. For example, a pair of electrically conductive signal lines 302A-B can be used to connect to each of electrode pairs $600A_1$-$B_1$ and $600A_2$-$B_2$ or alternatively, these electrode pairs $600A_1$-$B_1$ and $600A_2$-$B_2$ can be separately accessed by separate pairs of electrically conductive signal lines $302A_1$-$B_1$ and $302A_2$-$B_2$ extending back to the proximal end of the catheter 100.

Planar Resonator Approach

A cylindrically co-planar electrode approach to using frequency to select a location for heat deposition is shown and described herein with respect to FIGS. 6A, 6B, and 6C and elsewhere. A strip-line approach to using frequency to select a location for heat deposition is shown and described herein with respect to FIGS. 5D and 5E and elsewhere. Another approach that can additionally or alternatively use frequency to select a location for heat deposition is a planar resonator approach.

In the context of the present planar resonator techniques, the following terminology may be helpful. A "main line" can be used to refer to an electrically conductive signal line that can transmit an RF or electromagnetic input signal from its source into an object. A "planar resonator line" can be used to refer to an electrically conductive signal line, such as of specified length, that resonates in response to a predefined or specified signal frequency. A "tap line" can be used to refer to an electrically conductive signal line that electrically connects or inductively couples the main line and the planar resonator line. In an example, the tap line can optionally include a frequency selective filter element, such as a frequency selective crystal selected to pass a signal at the resonance frequency of the planar resonator, such as can help avoid excessive loading of the main line when multiple planar resonators are connected thereto, however, this is not required. A "ground line" can be used to refer to an electrically conductive signal line that acts as an electrical ground. A "planar resonator" can be used to refer to a combination that can include a tap line, a planar resonator line, and optionally a ground line.

The main line, the planar resonator line, the tap line, the ground line and other connecting lines, if any, can all be placed either in a coplanar (including cylindrically coplanar) or strip-line configuration, such as on or within an active semiconductor or other substrate (e.g., substrate 502) of the ultimate application object (e.g., heating device 500 of the catheter 100) or the load. The planar resonator can act as a shunt cavity. The length of the planar resonator line can be fabricated to resonate at a frequency that can be specified to correspond to a specified multiple of a quarter of the wavelength ($\lambda/4$) of an addressing frequency of an input electromagnetic signal (when the planar resonator is grounded) or to correspond to a specified multiple of a half of the wavelength ($\lambda/2$) of an addressing frequency of an input electromagnetic signal (when the planar resonator is non-grounded, e.g., is in an open-ended non-grounded circuit configuration). The tap line, its impedance, and the position of its electrical connection or coupling between the main line and the planar resonator can be configured so as to help increase or maximize the power flow into the planar resonator at its designated resonant frequency and to help reduce or minimize the power flow into the planar resonator at frequencies other than at its designated resonant frequency (e.g., for example at a different resonance frequency of one or more other planar resonators that are also electrically connected (or capacitively coupled) to the main line. By appropriately selecting tap-line impedance in this way, a particular planar resonator need not place a significant load on the main line when the electrical signal on the main line is of a frequency different from the resonant frequency of that planar resonator. This can help promote or ensure power flow past a non-addressed planar resonator to reach and flow into another planar resonator, also coupled to the main line, when such other planar resonator is at resonance.

Various planar resonator structures can be included along the catheter 100, with the one or more planar resonators being addressed by a particular frequency creating a transmission line cavity at that particular frequency, with one or more non-addressed planar resonators reflecting the excitation signal at that particular frequency. It can be referred to as "planar" because it is a relatively flat transmission line cavity, rather than a spatial transmission line cavity such as would be used in a microwave oven. The flat plane can be curved, for example, wrapped around a circumference of a catheter or other cylindrical or tubular structure, such as explained elsewhere herein.

In a planar resonator approach, an RF or like electromagnetic signal can be transmitted through a conductor, which can be referred to as "a main line" as a source of power for one or more frequency-addressable planar resonators that can be capacitively or inductively coupled to the main-line. The individual planar resonators can provide localized heat generation, such as within or on a catheter 100 or other object upon which the planar resonators are located. Individual planar resonators can be selectively patterned, such as including a selectively patterned electrical conductor within an electrode layer 503, or otherwise arranged to provide one or more individual planar (which can include cylindrically planar or other flat or curved 2D surface) resonators such as can be spatially located or distributed to cover a specified spatial region or geometry (for example, along at the length of a tubular catheter 100 or other desired object). The main line that is inductively or capacitively coupled to the planar resonator can be used to selectively trigger or transfer power at selectively addressable different locations along the main line for use by a load (such as an adjacent or nearby active substrate layer 502), such as for example but not limited to generating heat at the specified location of the load. The present techniques can be used to create or control such a spatial distribution of power output along the main line of the planar resonator using the frequency of the RF or other electromagnetic input signal for providing such controllable addressing of a specified location along the main line.

The present techniques can include providing a fixed-frequency planar resonator that can be configured to act as a frequency-dependent RF cavity. An input control signal can be frequency-scanned scanned along the main line and can produce what may appear or look like an amplitude dip, as seen from the main-line's perspective, at the resonance frequency of the planar resonator. Such an apparent amplitude dip is not primarily due to loss of power, but instead, is due largely to redirection of the electrical input signal on the main-line into the planar resonator cavity at the appropriate resonance frequency of the planar resonator. In this way, a frequency-specific path can be created, such as for depositing energy at a desired location along the length of the main line at which a planar resonator is coupled to the main line. Without being bound by theory, an electrical or magnetic standing wave can be created in the planar resonator when the input signal frequency matches the pre-specified frequency of the particular resonator. At such resonance frequency, a standing wave occurs in the electrode provided by the planar resonator line and an accompanying substrate phenomenon occurs in the adjacent or nearby active substrate, such that energy can be deposited into the substrate for heat generation, as opposed to merely draining the electrical energy out of the resonator by shunting electrical current to ground.

Multiple planar resonators having various different resonance frequencies can be arranged along and connected or coupled to the main line. Of these multiple planar resonators, only those resonators having a resonance frequency that matches an input frequency of the electromagnetic signal present on the main line will resonate, thereby causing the amplitude dip (from the main line perspective) for depositing energy at the desired one or more locations of only such one or more resonating planar resonators. Other planar resonators attached or coupled to the main line having different resonance frequencies will reflect the applied electromagnetic signal, without depositing energy at the locations of such non-resonating planar resonators. In sum, using multiple planar resonators attached or coupled to a main line, multiple frequency-selectable energy deposition locations can be provided and selectively addressed by selecting the appropriate tuning frequency of the electromagnetic signal placed on the main line.

Thus, the present techniques can enable the control of an energy flow path of an RF or electromagnetic signal along a main line. Such control can be provided by altering the frequency of the input RF or electromagnetic signal. In the case of a planar resonator that is inductively coupled to the main line via a tap line, the amount of energy delivered can be impacted or managed by at least two factors: (1) an impedance of the connection between the main line and the planar resonator; and (2) the location of the connection or coupling into the planar resonator, which can alter the distribution of energy within the planar resonator, such as explained herein.

Figure 7:
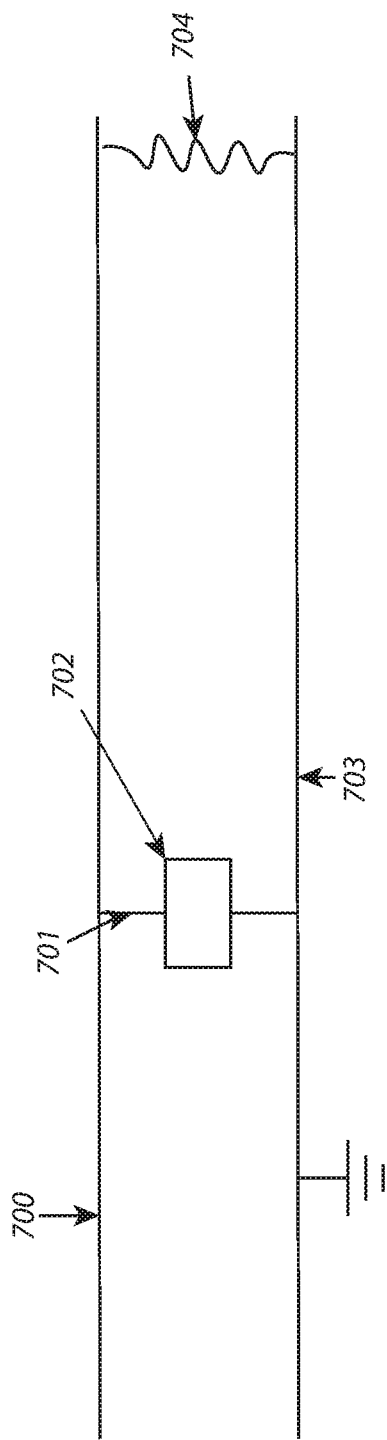
FIG. 7 shows a block diagram of an example of an overall setup of portions of a planar resonator configuration.

FIG. 7 shows a block diagram of an example of an overall setup of portions of a planar resonator configuration. In the example of FIG. 7, an electrically conductive main line 700 can be electrically connected or inductively coupled, via a tap line 701, to a fixed resonance frequency planar resonator line 702 and to a ground line 703. One or more fixed resonance frequency planar resonator lines 702 can similarly be connected or coupled in parallel via corresponding tap lines 701 in a similar manner. FIG. 7 shows conceptual representation of resistive or other load 704 between the ground line 703 and the main line 700, such as a shunt in parallel with the one or more planar resonator lines 702. The resistive load 704 need not be a separate physical component that is included; instead, the resistive load 704 is intended to represent conceptually via a shunt resistor how power can be coupled into the substrate at resonance by a particular planar resonator having a planar resonator line 702.

Figure 8:
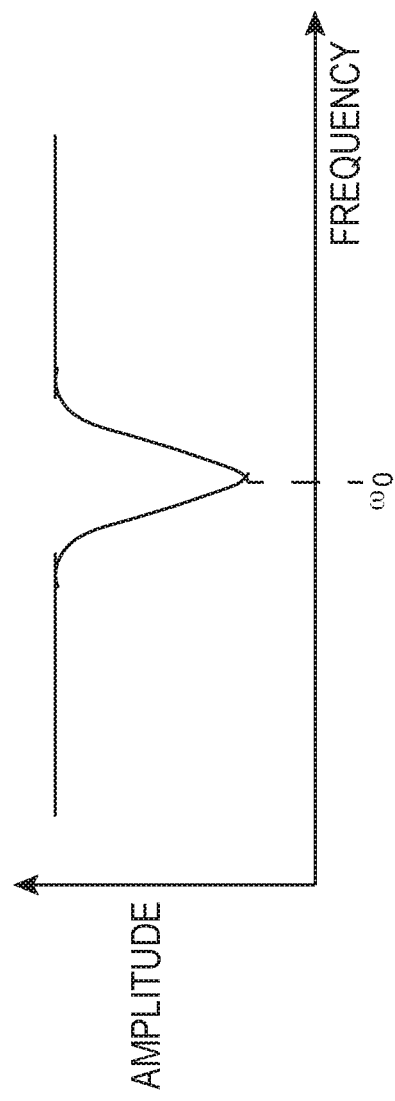
FIG. 8 shows a conceptualized (not real data) example of a graph of amplitude vs. angular frequency for a planar resonator.

FIG. 8 shows a conceptualized (not real data) example of a graph of amplitude vs. angular frequency, showing an illustrative conceptual example of a signal amplitude dip (from the perspective of the main line) at a specified or pre-designed response or resonance frequency, $\omega_0$, of the planar resonator having a planar resonator line 702.

Figure 9:
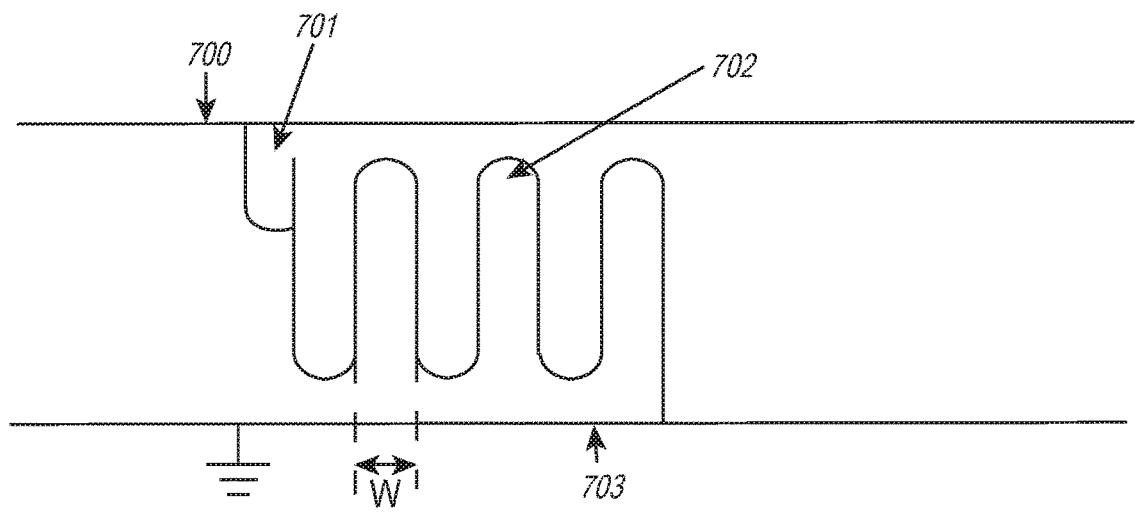
FIG. 9 shows an illustrative physical layout schematic example of a grounded planar resonator having a planar resonator line.

FIG. 9 shows an illustrative physical layout schematic example of a grounded planar resonator having a planar resonator line 702. In the example of FIG. 9, a main line 700 is connected to the planar resonator line 702 via the tap-line 701. In this example, the planar resonator line 702 includes specified number of electrically conductive segments that can be interconnected such as shown and arranged in a serpentine, undulating, or meandering manner. In this grounded configuration, the total planar resonator line 702 length (e.g., sum of segment lengths plus interconnections between segments) can correspond to a specified multiple of quarter wavelengths ($\lambda/4$) of a desired addressing frequency of an input electromagnetic signal that will be used to address the planar resonator having the planar resonator line 702, such as to create heat at the location of the specified planar resonator when it is addressed by the appropriate frequency input signal on the main line 700. The spacing between neighboring resonator line segments within the serpentine arrangement of the planar resonator line 702 can generally be set to reduce, minimize, or eliminate electromagnetic coupling between such segments. In general, this inter-segment spacing can be about 3 to 5 times the linewidth of the signal trace of the planar resonator line 702. If a band of resonance or response frequencies is desired, carefully managed inter-segment coupling can be used to expand the resonant frequency range of the planar resonator line 702. This can be accomplished, for example, by decreasing the inter-segment spacing to increase inter-segment coupling.

Figure 10:
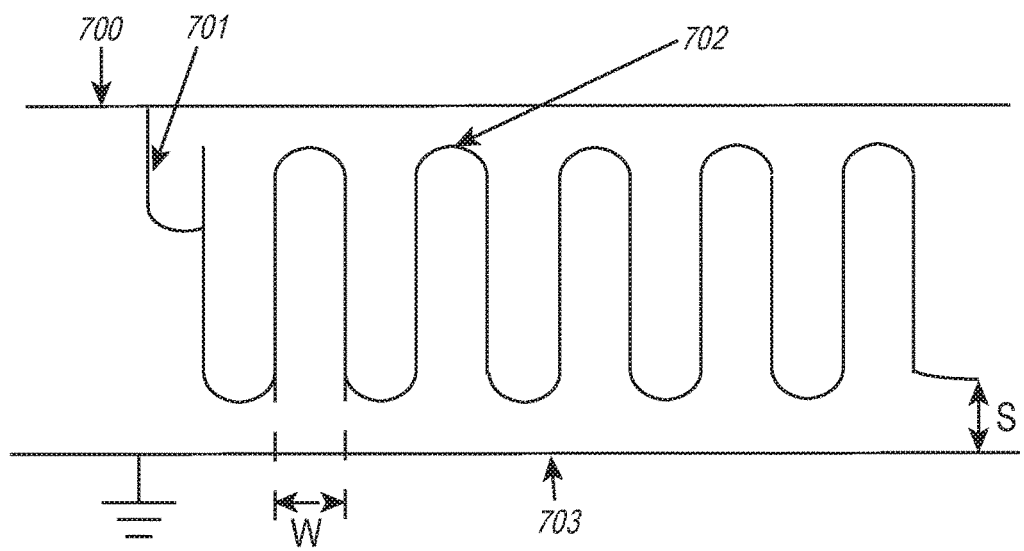
FIG. 10 shows an illustrative physical layout schematic example of a non-grounded planar resonator line, e.g., a free-floating or non-terminated planar resonator line.

FIG. 10 shows an illustrative physical layout schematic example of a non-grounded planar resonator line 702, e.g., a free-floating or non-terminated planar resonator line 702. In the example of FIG. 10, the main line 700 can be electrically connected to the planar resonator line 702 via the tap-line 701, but the planar resonator line 702 is not electrically connected to the ground line 703. Instead, the planar resonator line 702 can be directed away from the ground line 703, such as to maintain a safe spacing, s, therebetween, such as to help inhibit or prevent electromagnetic coupling between the planar resonator line 702 and the ground line 703.

In this example of FIG. 10, the planar resonator line 702 includes specified number of electrically conductive segments that can be interconnected such as shown and arranged in a serpentine, undulating, or meandering manner. In this non-grounded configuration, the total planar resonator line 702 length (e.g., sum of segment lengths plus interconnections between segments) can correspond to a specified multiple of half wavelengths ($\lambda/2$) of a desired addressing frequency of an input electromagnetic signal that will be used to address the planar resonator line 702, such as to deposit heat in the substrate at the location of the specified planar resonator line 702 when it is addressed by the appropriate frequency input signal on the main line 700. The spacing between neighboring resonator line segments within the serpentine arrangement of the planar resonator line 702 can generally be set to reduce, minimize, or eliminate electromagnetic coupling between such segments, or to expand resonance frequency range, such as explained above with respect to FIG. 9.

Figure 11B:
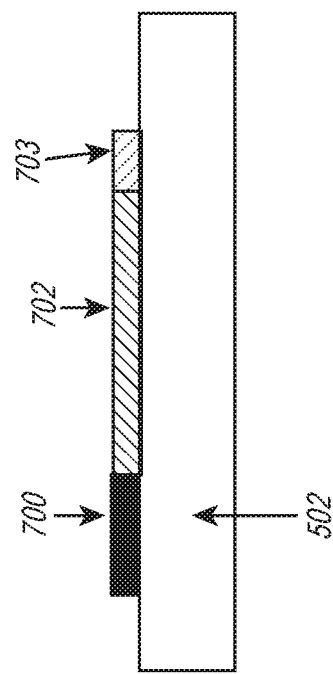
FIG. 11A (flattened planarized top view) and FIG. 11B (flattened planarized cross-sectional side view) shows an example of a grounded cylindrically coplanar arrangement of the planar resonator system.
Figure 11A:
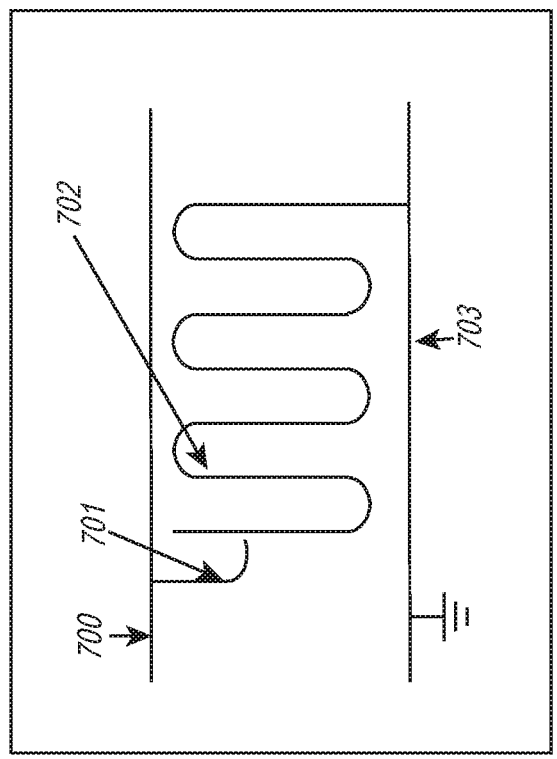

FIG. 11A (flattened planarized top view) and FIG. 11B (flattened planarized cross-sectional side view) shows an example of a grounded cylindrically coplanar arrangement of the planar resonator system. FIG. 11A is similar to FIG. 9. FIG. 11B provides a flattened planarized cross-sectional side view that shows an example of how the various components of the planar resonator system (e.g., including the planar resonator line 702, the main line 700, and the ground line 703) can be located on or near a surface of an active substrate 502, such as within a shared plane in a co-planar arrangement, such as within an electrode or power layer 503 that can be located adjacent or near to the active substrate 502 layer.

Figure 12B:
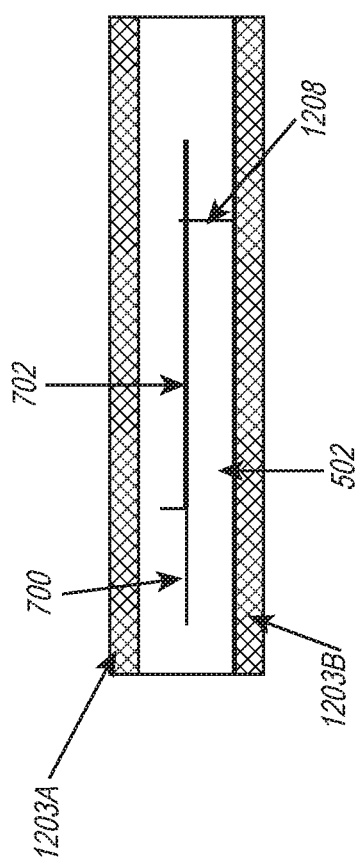
FIG. 12A (flattened planarized top view), FIG. 12B (flattened planarized cross-sectional side view along edge 1210 of FIG. 12A), and FIG. 12C (flattened planarized cross-sectional side view along edge 1220 of FIG. 12A) show examples of a cylindrically coplanar arrangement of the planar resonator system in a strip line arrangement.
Figure 12C:
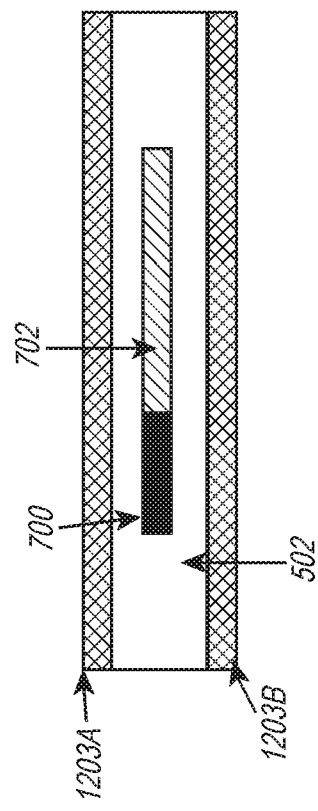
Figure 12A:
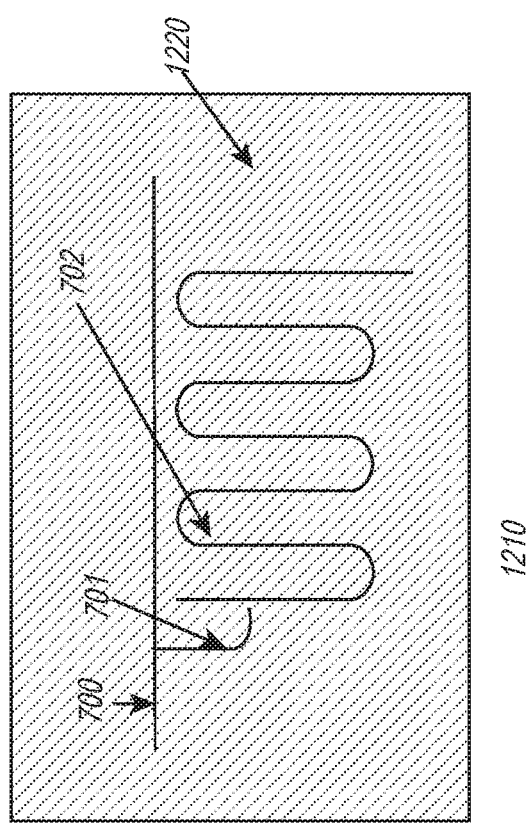

FIG. 12A (flattened planarized top view), FIG. 12B (flattened planarized cross-sectional side view along edge 1210 of FIG. 12A), and FIG. 12C (flattened planarized cross-sectional side view along edge 1220 of FIG. 12A) show examples of a cylindrically coplanar arrangement of the planar resonator system in a strip line arrangement. No ground line 703 is shown in FIG. 12A, but FIGS. 12B and 12C shows the ground planes 1203A-B respectively above and below the planar resonator line 702, which is located or embedded in an active substrate 502, which separates the planar resonator line 702 from the ground planes 1203A-B in the strip line arrangement. Optionally, in a grounded strip line arrangement, the planar resonator line 702 can be generally separated by the active substrate 502 from one or both of the ground planes 1203A-B, but the planar resonator line 702 can be selectively electrically interconnected to one or both of the ground planes 1203A-B, such as by one or more electrically conductive via 1208 structures through the active substrate 502 at one or more specified locations. It is not essential that the main line 700 and the resonator 702 be along the same horizontal plane such as shown in FIGS. 12A-C, but can be arranged along the same plane for ease of manufacturing.

Figure 13A:
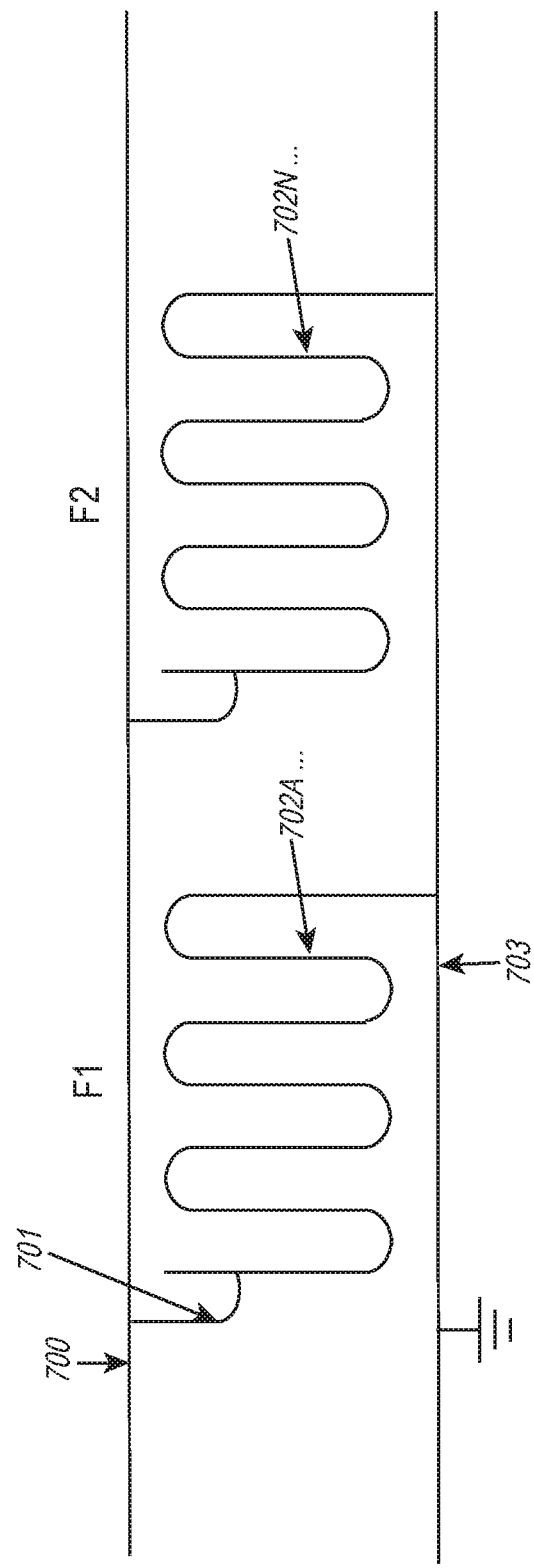
FIG. 13A (flattened planarized top schematic view) shows multiple (e.g., two or more) planar resonator lines at different locations along a length the main line.

FIG. 13A (flattened planarized top schematic view) shows multiple (e.g., two or more) planar resonator lines 702A ... 702N at different locations along a length the main line 700. Such planar resonator lines 702A ... 702N can be selectively addressed (e.g., individually or in one or more groups), such as using a frequency of an electrical signal that can be placed on the main line 700, such as via one of the lines 302A, 302B. The selective addressing can be performed using the planar resonator lines' 702A-N corresponding optionally different resonance frequencies $f_1$, $f_N$, such as for generating heat deposition at pre-specifiable locations in an active semiconductor or other substrate 502. One or more temperature sensors can be located near individual resonator lines 702A-N, such as to allow readout of temperature data (and sensor identity (ID)) information indicative of the particular location of the particular temperature sensor providing the temperature reading. Such distributed temperature sensors can be accessed using electrical interconnection lines 304A-B. Such temperature information can be used to control a sweep selectively activating particular planar resonators in a matrix of such planar resonators. If a heat gradient is desired, for example between adjacent planar resonators, such adjacent planar resonators can be triggered by passing an electrical signal having frequency components at the different resonance frequencies of the adjacent planar resonators desired to be addressed to dynamically trigger heat generation in the adjacent or nearby active substrate.

An illustrative example can be provided as follows, with the understanding that the wavelength values given below correspond to wavelengths in free space, since the example is intended to be generic to the specific active substrate that is chosen. In practice, the resulting wavelength values should be modified depending on the permittivity of the active substrate material that is used. For example, in a strip-line configuration, wavelength in the active substrate $\lambda_s = \lambda_o / \sqrt{\epsilon_r}$, where $\lambda_o$ is the wavelength in free space and $\epsilon_r$ is the relative permittivity of the active substrate material. In a coplanar configuration, wavelength in the active substrate $\lambda_s = \lambda_o / (2 * \sqrt{\epsilon_{eff}})$ where $\lambda_o$ is the wavelength in free space and $\epsilon_{eff} = (\epsilon_r+1)/2$, where $\epsilon\_eff = (\epsilon_r+1)/2$, where $\epsilon_r$ is the relative permittivity of the active substrate material.

With this caveat in mind, continuing with the illustrative example, to selectively address a particular resonator line 702A when the frequency of the electrical input signal on the main line 700 is 10 GHz, which has a corresponding (free space) wavelength of approximately 3 cm, the corresponding quarter wavelength ($\lambda/4$) for a grounded planar resonator line 702A is about 7.5 mm, and the corresponding half wavelength ($\lambda/2$) for a non-grounded planar resonator line 702A is 15 mm. In an illustrative example of a catheter example in which the catheter circumference is 4.17 mm, a quarter wavelength ($\lambda/4$) for a grounded planar resonator line 702A is less than two circumferential turns about the catheter, and the corresponding half wavelength ($\lambda/2$) for a non-grounded planar resonator line 702A is less than four circumferential turns about the catheter. For an electrical trace having a line width of 0.2 mm, for example, spacing between adjacent planar resonator lines should be at least approximately two to five times the line width for an illustrative example of a semiconductor substrate, e.g., 1.8 mm (as an illustrative example) to avoid intercoupling between adjacent resonators while allowing closer packing of resonators upon the catheter structure. This means that there can be about 5 such frequency-controllable resonator heat sources per centimeter of catheter length. For example, within a 10 centimeter catheter length, there can be about 50 frequency-controllable resonator heat sources.

Thus, for a grounded planar resonator line 702A, the aggregate length of the serpentine, meandering, or other electrically conductive trace of the planar resonator line 702A can be 7.5 mm to permit that particular planar resonator 702A to be selectively addressed using a 10 GHz frequency on the main line 700, to which the planar resonator line 702A can be electrically interconnected using a corresponding individual tap-line of a desired impedance. The meandering planar resonator line 702A terminates at the ground line 703. In the present case a meandering planar resonator line 702A is merely an example. The geometry or layout of the planar resonator line can depend on the space and needs of each individual application. In this way, in this grounded resonator example, a 10 GHz input signal will now resonate with this grounded resonator line 702A and will result in a power flow into the selected resonator line 702A. It is possible that under the grounded scenario, the E (electrical) wave component of the applied electromagnetic input signal is drained out of the planar resonator. This may especially be true in the case of a capacitively-coupled planar resonator structure. However, without being bound by theory, the M (magnetic) wave component of the applied electromagnetic input signal will be trapped and will create heat in the adjacent substrate.

It can be desirable to reduce or avoid any signal inter-segment signal coupling within a particular meandering trace planar resonator line 702A-N, such as to help establish a "crisp," e.g., highly selective, frequency response of the selected planar resonator to the input electrical signal frequency. By providing an inter-segment line spacing of 3 to 5 times the line width of the serpentine or meandering electrical conductor trace of a planar resonator line, such inter-segment coupling can be reduced or avoided. However, if for a particular application it is desired that a particular planar resonator line 702A-N be selectively addressable using a broader range of frequencies, instead of a highly-selective narrowband or single frequency per selected resonator power flow path, careful use of inter-segment spacing to provide a desired amount of inter-segment coupling can help broaden the resonance frequency band of the particular planar resonator line 702A-N. Parasitic coupling may create undesirable or unpredictable results and thus may be unsuitable for or may limit reliable power flow path selection. A higher addressing frequency corresponds to lower addressing wavelength. A lower addressing wavelength decreases the corresponding aggregate trace length of the resonator lines 702A-N and, therefore, can result in less space needed or better density of the resonator lines 702A-N along the main line 700.

In certain examples, a planar resonator cavity can be capacitively loaded instead of electrically connected to the main line via a tap line, which may form an inductive connection to the main line. Examples of capacitive loading are shown in FIGS. 13B, 13C, 13D, and 13E.

FIG. 13B shows a top view of an example illustrating how a resonant cavity can be capacitively coupled to a main line. For example, a planar resonator line can be separated from the main line by a gap, G, at a resonator location, rather than being electrically connected thereto by a tap-line. The resonance frequency of the capacitively coupled resonator structure can be established as described above for the electrically-connected resonator structure (e.g., 10 GHz resonance frequency corresponds to quarter wavelength ($\lambda/4$) for a grounded planar resonator 702A of about 7.5 mm). However, for a capacitively-coupled resonator structure, the distance of the gap G needed for capacitive coupling to the resonator structure is also frequency dependent, and can be determined as explained in the above-incorporated A. Gopinath and C. Gupta, "Capacitance Parameters of Discontinuities in Microstriplines," IEEE Trans. On Microwave Theory and Techniques, Vol. MTT-26, No. 10, October 1978, p. 831-836. Thus, by selecting the appropriate resonator (aggregate planar resonator line length, meandering spacing, etc.) and the appropriate capacitive coupling gap, G, the resonator can be activated at a specified frequency of an electrical input signal applied to a main-line that is electrically insulated from the resonator at the capacitive coupling gap, G. This can enable frequency-controlled deposition of heat at an adjacent semiconductor or other active heating substrate at desired locations of one or more appropriately tuned resonator cavities. Other resonators, which can similarly be capacitively coupled to the main line at one or more other (different) resonance frequencies can be configured to reflect, at the selected resonance frequency, energy of the electrical signal applied on the main-line. In this way, only the one or more desired capacitively coupled resonators being addressed are selectively activated.

FIG. 13C shows a top view of an example of a serpentine or meandering resonant cavity trace of a planar resonator line that can be capacitively coupled to a main line by an insulating gap, G, at a desired capacitive coupling location. At other locations, the resonator structure can be separated from the main line by a larger insulating separation spacing, I, e.g., I>G. In this way, the insulating gap G dominantly determines capacitive coupling of the planar resonator line structure to the main line, rather than the other locations of the planar resonator line structure, which have the larger separation, I, from the main line and, therefore, such other locations of the planar resonator line structure are not capacitively coupled to the main line.

Figure 13D:
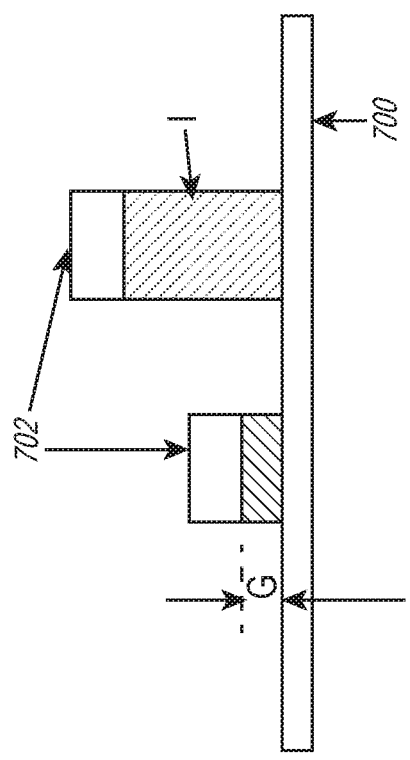
FIG. 13D shows a side view of an example in which a specific portion of a capacitively coupled planar resonance line structure can be separated from a main line by an insulating gap, G, such as to capacitively couple the planar resonator line structure to the main line.

FIG. 13D shows a side view of an example in which a specific portion of a capacitively coupled planar resonance line structure can be separated from a main line by an insulating gap, G, such as to capacitively couple the planar resonator line structure to the main line, while other portions of the capacitively coupled planar resonator line structure can be separated from the main line by a larger insulating separation spacing, I, such that such other portions of the planar resonator line structure do not capacitively couple to the main line.

Figure 13E:
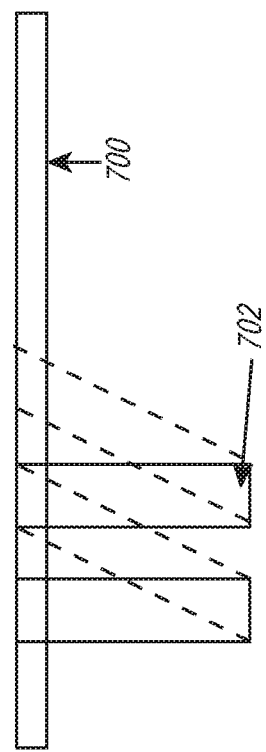
FIG. 13E shows an example of a capacitively coupled planar resonator line structure that can be wrapped around a main line, such as a desired location that can be separated from the main line by an insulating gap G.

FIG. 13E shows an example of a capacitively coupled planar resonator line structure that can be wrapped around a main line, such as a desired location that can be separated from the main line by an insulating gap G that dominantly determines the capacitive coupling of the planar resonator line structure to the main line, with other portions of the planar resonator line structure separated from the main line by a larger insulated distance, such as not to capacitively couple such other locations of the planar resonator line structure to the main line.

Examples of Sensor Configurations

As explained herein, it can be desirable to detect, sense, or measure temperature at one or more desired locations along the catheter 100. Sensed temperature information can be used for, among other things, controlling heating (e.g., location, intensity, gradient, duration, or the like). For example, it can be desirable to sense temperature at locations along the catheter 100 at which an exterior of the catheter 100 contacts adjacent tissue that is either at risk from being exposed to excessive heat, or at which tissue is desired to be heated to a desired therapeutic or operating temperature. In another example, it can be desirable to sense temperature at locations along the catheter adjacent or near to the locations selected for providing focused heat deposition, such as for biofilm neutralization or other benefit.

FIG. 14A shows an example in which temperature or other sensors 1400A, . . . , 1400N can be located and electrically connected in parallel with each other at various locations along a length of a catheter 100. Each sensor 1400 can include or can be associated with corresponding sensor identification circuitry 1402A, . . . , 1402N such as for allowing identification of the particular sensor (and, therefore, location of that sensor) along with its temperature or other sensor reading. The sensors 1400 and corresponding sensor identification circuitry 1402 can be addressed by the lines 304A, 304B. In an example, the return line 304B can be omitted. In an example, the sensor identification circuitry 1402 can include a radiofrequency identification (RFID) module, such as can permit wireless addressing and accessing of previously encoded sensor identification information. In an example, the sensor identification circuitry 1402 can include an integrated circuit (IC) chip with previously encoded sensor identification information, such as can be stored in a non-volatile or other memory element on the IC.

In an example, multiple temperature or other sensors 1400A, . . . , 1400N can be located and electrically connected in parallel with each other at various locations along a length of a catheter 100. The corresponding sensor identification circuitry 1402A, . . . , 1402N can include encoded information specifying an individualized response delay in response to a query "ping" signal that can be issued by a controller to the lines 304A, 304B to which the sensors 1400 are connected. By pre-encoding different individualized response delays for the different sensors 1400 into the corresponding sensor identification circuitry 1402, corresponding individual sensor data can be read serially via the lines 304A, 304B such as in response to a query ping signal issued by a controller across the lines 304A, 304B.

FIG. 14B shows an example in which the sensors 1400A, . . . , 1400N include a frequency-selective filter, such as can allow frequency-selective addressing of a particular temperature sensor 1400 to extract a temperature reading; the corresponding identification of the sensor can be pre-specified by tuning the temperature sensors 1400 at different locations along the catheter 100 to different addressing frequencies at the different locations.

FIG. 14C shows an example in which the temperature or other sensors 1400A, . . . , 1400N are dedicated to or co-integrated with corresponding local heat sources, such as by being electrically connected (e.g., as a load) to a corresponding planar resonator 702 that can be addressed by selecting an appropriate frequency of electrical input signal placed on the main line 700. In this way, when a particular planar resonator 702 is activated by an electrical signal of an appropriate frequency placed on the main line 700, the corresponding temperature sensor is also activated, allowing a temperature readout, e.g., via a temperature readout electrically conductive trace 304 that is electrically connected to the temperature sensor 1400.

Although the above example has emphasized temperature sensors, other sensors can additionally or alternatively similarly be included. For example, the sensors can include an arrangement of temperature sensors, pressure sensors, or other sensor modalities, with electrical or optical conductors extending individually thereto, such as longitudinally along the catheter to a location outside of the patient's body.

An Illustrative Specific Example of a Catheter Construction

The following is an illustrative non-limiting example of a specific catheter construction.

1.

Figure 15:
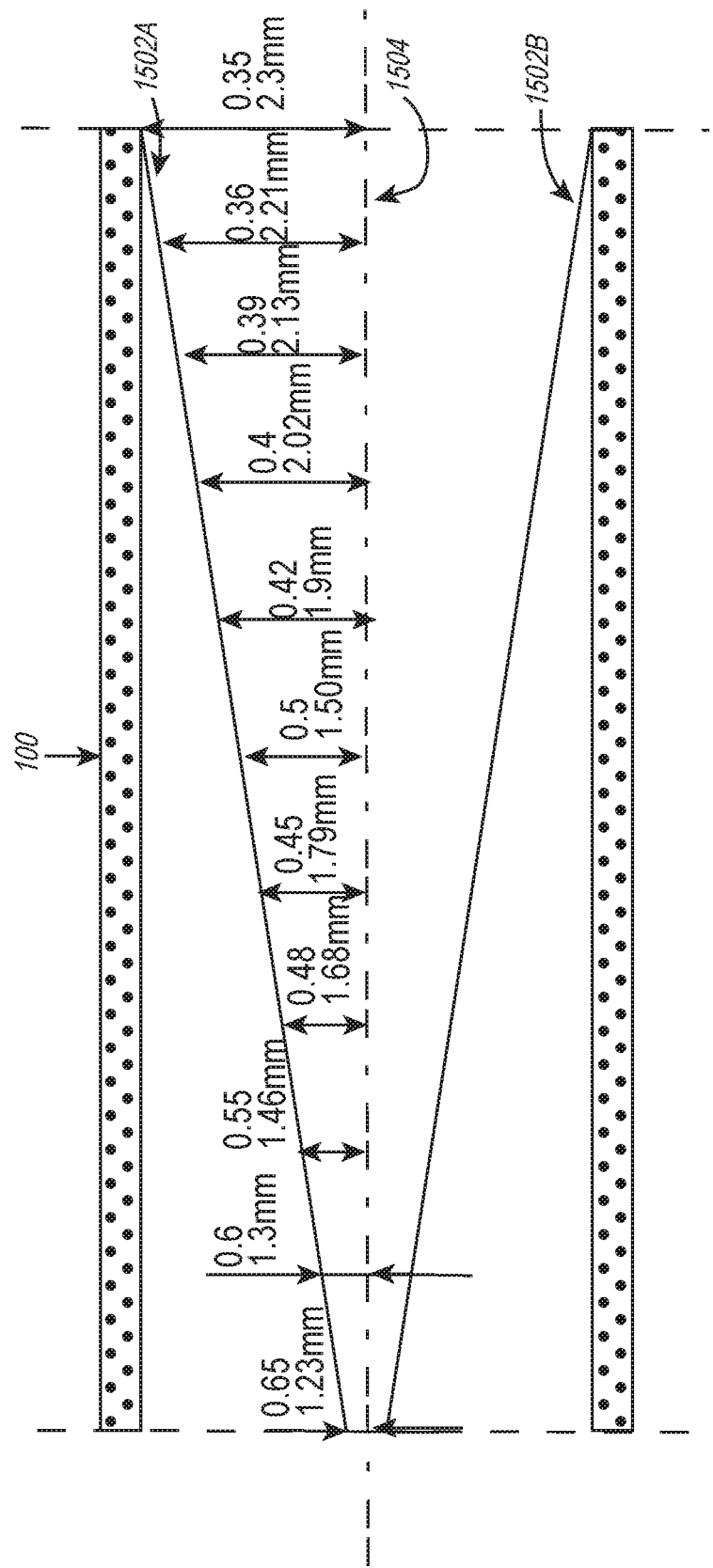
FIG. 15 shows a planarized cylindrical view example of two linearly diverging line electrode traces.

FIG. 15 shows a planarized cylindrical view example of two linearly diverging line electrode traces 1502A-B that can be located on a body of catheter 100. A median longitudinal axis 1504 can be defined on the cylinder as shown in FIG. 15, such that the median longitudinal axis is equidistant from each of the electrode traces 1502A-B on the cylindrical structure of the electrode traces 1502A-B and their associated cylindrical heat-generating substrate. As shown in the planarized cylindrical view of FIG. 15, a cylindrical-surface (circumferential) distance between the electrode traces 1502A-B increases in a direction from left to right in FIG. 15. If an input signal is applied at the left, where the circumferential interelectrode distance is smallest, an attenuation ($\alpha$) of the electrical signal decreases at lengthwise locations along opposite electrode traces as the circumferential interelectrode distance increases, such as explained in U.S. Pat. No. 9,536,758, which is incorporated herein by reference.

for a location at which electrodes are almost diametrically opposed across a circular cross-section of a 5 French catheter. In the French scale for catheters, the size in French units is roughly equal to the circumference of the catheter in millimeters, that is 1 French=$2 \cdot \pi \cdot r = \pi \cdot D$, where r=radius and D=diameter. The approximate maximum available circumferential interelectrode space ($S_{max}$) is limited to half the circumference. Thus, for a circumferential interelectrode spacing of S=2.36 mm, the corresponding catheter size is 5 French, which has a circumference of 5 mm, such that half the circumference is 2.5 mm. Thus, for a 5 French catheter, it is possible to separate the electrodes by a circumferential interelectrode spacing of $S_{max}$=2.5 mm, with the largest circumferential interelectrode spacing value of S=2.36 mm in Table 1 selected to be slightly under the maximum value of $S_{max}$=2.5 mm.

As seen in Table 1, for a given frequency (e.g., 10 GHz) there is more attenuation ($\alpha$=2.24)—which means more power deposition and heat generation—at the smallest circumferential interelectrode distance of 0.24 mm at the left end of the electrode traces shown in FIG. 15 than at the largest circumferential interelectrode distance of 2.36 mm at the right end of the electrode traces shown in FIG. 15, at which the attenuation is $\alpha$=0.54. Also seen in Table 1, as the frequency of the applied electrical signal is decreased from 10 GHz to 0.3 GHz, the attenuation decreases to 0.39 at a circumferential interelectrode spacing of 0.24 mm and to 0.09 at a circumferential interelectrode spacing of 2.36 mm.

TABLE 1

Attenuation ($\alpha$) vs. Circumferential Interelectrode spacing (mm) and Frequency (GHz), with substrate conductance of 10 Siemens/meter

| Spacing (mm) | Freq 10 GHz | Freq 9.03 GHz | Freq 8.06 GHz | Freq 7.09 GHz | Freq 6.12 GHz | Freq 5.15 GHz | Freq 4.18 GHz | Freq 3.21 GHz | Freq 2.24 GHz | Freq 1.27 GHz | Freq 0.3 GHz |
|---|---|---|---|---|---|---|---|---|---|---|---|
| 2.36 | 0.54 | 0.51 | 0.48 | 0.45 | 0.42 | 0.39 | 0.35 | 0.31 | 0.26 | 0.19 | 0.09 |
| 2.14 | 0.58 | 0.55 | 0.52 | 0.49 | 0.45 | 0.42 | 0.37 | 0.33 | 0.27 | 0.21 | 0.10 |
| 1.93 | 0.62 | 0.59 | 0.56 | 0.53 | 0.49 | 0.45 | 0.40 | 0.35 | 0.30 | 0.22 | 0.11 |
| 1.72 | 0.68 | 0.64 | 0.61 | 0.57 | 0.53 | 0.49 | 0.44 | 0.38 | 0.32 | 0.24 | 0.12 |
| 1.51 | 0.74 | 0.71 | 0.67 | 0.63 | 0.58 | 0.53 | 0.48 | 0.42 | 0.35 | 0.26 | 0.13 |
| 1.30 | 0.82 | 0.78 | 0.74 | 0.69 | 0.65 | 0.59 | 0.53 | 0.47 | 0.39 | 0.29 | 0.14 |
| 1.08 | 0.93 | 0.88 | 0.83 | 0.78 | 0.73 | 0.67 | 0.60 | 0.53 | 0.44 | 0.33 | 0.16 |
| 0.87 | 1.07 | 1.02 | 0.96 | 0.90 | 0.84 | 0.77 | 0.69 | 0.61 | 0.51 | 0.38 | 0.19 |
| 0.66 | 1.28 | 1.22 | 1.15 | 1.08 | 1.00 | 0.92 | 0.83 | 0.73 | 0.61 | 0.46 | 0.22 |
| 0.45 | 1.62 | 1.54 | 1.45 | 1.36 | 1.27 | 1.16 | 1.05 | 0.92 | 0.77 | 0.58 | 0.28 |
| 0.24 | 2.24 | 2.13 | 2.01 | 1.89 | 1.75 | 1.61 | 1.45 | 1.27 | 1.06 | 0.80 | 0.39 |

Table 1 shows calculated values of attenuation ($\alpha$) vs. circumferential interelectrode spacing (mm) and vs. frequency of the electrical signal that is applied at the left ends of the electrode traces 1502A-B as shown in FIG. 15, for an example in which a semiconductor substrate located adjacent to the electrode traces has an electrical conductance of 10 Siemens/meter. In Table 1, the greater the signal attenuation at a given location, the more energy is deposited in the form of heat at that location.

In Table 1, the circumferential interelectrode spacings (along the cylindrical surface upon which the electrode traces are disposed) range from 0.24 mm to 2.36 mm. The maximum circumferential interelectrode spacing of 2.36 mm was selected based on the approximate available space Thus, Table 1 demonstrates that frequency can be used to control the amount of energy deposited into an adjacent active substrate (which is proportional to the amount of heat generated in the adjacent active substrate) at various locations along a pair of electrodes with a variable circumferential interelectrode spacing. Table 1 also demonstrates that a heating gradient can be created between locations (e.g., ends) of electrode traces having a variable circumferential interelectrode spacing therebetween. Tables 2 and 3 provide calculated data that is similar to that shown in Table 1, but for different values of conductance of the semiconductor substrate located adjacent to the electrode traces, with Table 2 providing data corresponding to a substrate conductance of 5 Siemens/meter and Table 3 corresponding to a substrate conductance of 2 Siemens/meter.

TABLE 2

Attenuation (α) vs. Circumferential Interelectrode spacing (mm)
and Frequency (GHz), with substrate conductance of 5 Siemens/meter

| Spacing (mm) | Freq 10 GHz | Freq 9.03 GHz | Freq 8.06 GHz | Freq 7.09 GHz | Freq 6.12 GHz | Freq 5.15 GHz | Freq 4.18 GHz | Freq 3.21 GHz | Freq 2.24 GHz | Freq 1.27 GHz | Freq 0.3 GHz |
|---|---|---|---|---|---|---|---|---|---|---|---|
| 2.36 | 0.27 | 0.26 | 0.24 | 0.23 | 0.21 | 0.19 | 0.17 | 0.15 | 0.13 | 0.10 | 0.05 |
| 2.14 | 0.29 | 0.28 | 0.26 | 0.24 | 0.23 | 0.21 | 0.19 | 0.16 | 0.14 | 0.10 | 0.05 |
| 1.93 | 0.31 | 0.30 | 0.28 | 0.26 | 0.24 | 0.22 | 0.20 | 0.18 | 0.15 | 0.11 | 0.05 |
| 1.72 | 0.34 | 0.32 | 0.30 | 0.29 | 0.27 | 0.24 | 0.22 | 0.19 | 0.16 | 0.12 | 0.06 |
| 1.51 | 0.37 | 0.35 | 0.33 | 0.31 | 0.29 | 0.27 | 0.24 | 0.21 | 0.18 | 0.13 | 0.06 |
| 1.30 | 0.41 | 0.39 | 0.37 | 0.35 | 0.32 | 0.30 | 0.27 | 0.23 | 0.20 | 0.15 | 0.07 |
| 1.08 | 0.46 | 0.44 | 0.42 | 0.39 | 0.36 | 0.33 | 0.30 | 0.26 | 0.22 | 0.17 | 0.08 |
| 0.87 | 0.54 | 0.51 | 0.48 | 0.45 | 0.42 | 0.38 | 0.35 | 0.30 | 0.25 | 0.19 | 0.09 |
| 0.66 | 0.64 | 0.61 | 0.58 | 0.54 | 0.50 | 0.46 | 0.41 | 0.36 | 0.30 | 0.23 | 0.11 |
| 0.45 | 0.81 | 0.77 | 0.73 | 0.68 | 0.63 | 0.58 | 0.52 | 0.46 | 0.38 | 0.29 | 0.14 |
| 0.24 | 1.12 | 1.06 | 1.01 | 0.94 | 0.88 | 0.80 | 0.72 | 0.63 | 0.53 | 0.40 | 0.19 |

TABLE 3

Attenuation (α) vs. Circumferential Interelectrode spacing (mm)
and Frequency (GHz), with substrate conductance of 2 Siemens/meter

| Spacing (mm) | Freq 10 GHz | Freq 9.03 GHz | Freq 8.06 GHz | Freq 7.09 GHz | Freq 6.12 GHz | Freq 5.15 GHz | Freq 4.18 GHz | Freq 3.21 GHz | Freq 2.24 GHz | Freq 1.27 GHz | Freq 0.3 GHz |
|---|---|---|---|---|---|---|---|---|---|---|---|
| 2.36 | 0.11 | 0.10 | 0.10 | 0.09 | 0.08 | 0.08 | 0.07 | 0.06 | 0.05 | 0.04 | 0.02 |
| 2.14 | 0.12 | 0.11 | 0.10 | 0.10 | 0.09 | 0.08 | 0.07 | 0.07 | 0.05 | 0.04 | 0.02 |
| 1.93 | 0.12 | 0.12 | 0.11 | 0.11 | 0.10 | 0.09 | 0.08 | 0.07 | 0.06 | 0.04 | 0.02 |
| 1.72 | 0.14 | 0.13 | 0.12 | 0.11 | 0.11 | 0.10 | 0.09 | 0.08 | 0.06 | 0.05 | 0.02 |
| 1.51 | 0.15 | 0.14 | 0.13 | 0.13 | 0.12 | 0.11 | 0.10 | 0.08 | 0.07 | 0.05 | 0.03 |
| 1.30 | 0.16 | 0.16 | 0.15 | 0.14 | 0.13 | 0.12 | 0.11 | 0.09 | 0.08 | 0.06 | 0.03 |
| 1.08 | 0.19 | 0.18 | 0.17 | 0.16 | 0.15 | 0.13 | 0.12 | 0.11 | 0.09 | 0.07 | 0.03 |
| 0.87 | 0.21 | 0.20 | 0.19 | 0.18 | 0.17 | 0.15 | 0.14 | 0.12 | 0.10 | 0.08 | 0.04 |
| 0.66 | 0.26 | 0.24 | 0.23 | 0.22 | 0.20 | 0.18 | 0.17 | 0.15 | 0.12 | 0.09 | 0.04 |
| 0.45 | 0.32 | 0.31 | 0.29 | 0.27 | 0.25 | 0.23 | 0.21 | 0.18 | 0.15 | 0.12 | 0.06 |
| 0.24 | 0.45 | 0.43 | 0.40 | 0.38 | 0.35 | 0.32 | 0.29 | 0.25 | 0.21 | 0.16 | 0.08 |

From Tables 1-3, it can be seen that a higher substrate conductance increases the attenuation, power deposition, and substrate heat generation resulting from an applied input signal of the various frequencies at the various circumferential interelectrode spacing locations.

Figure 16:
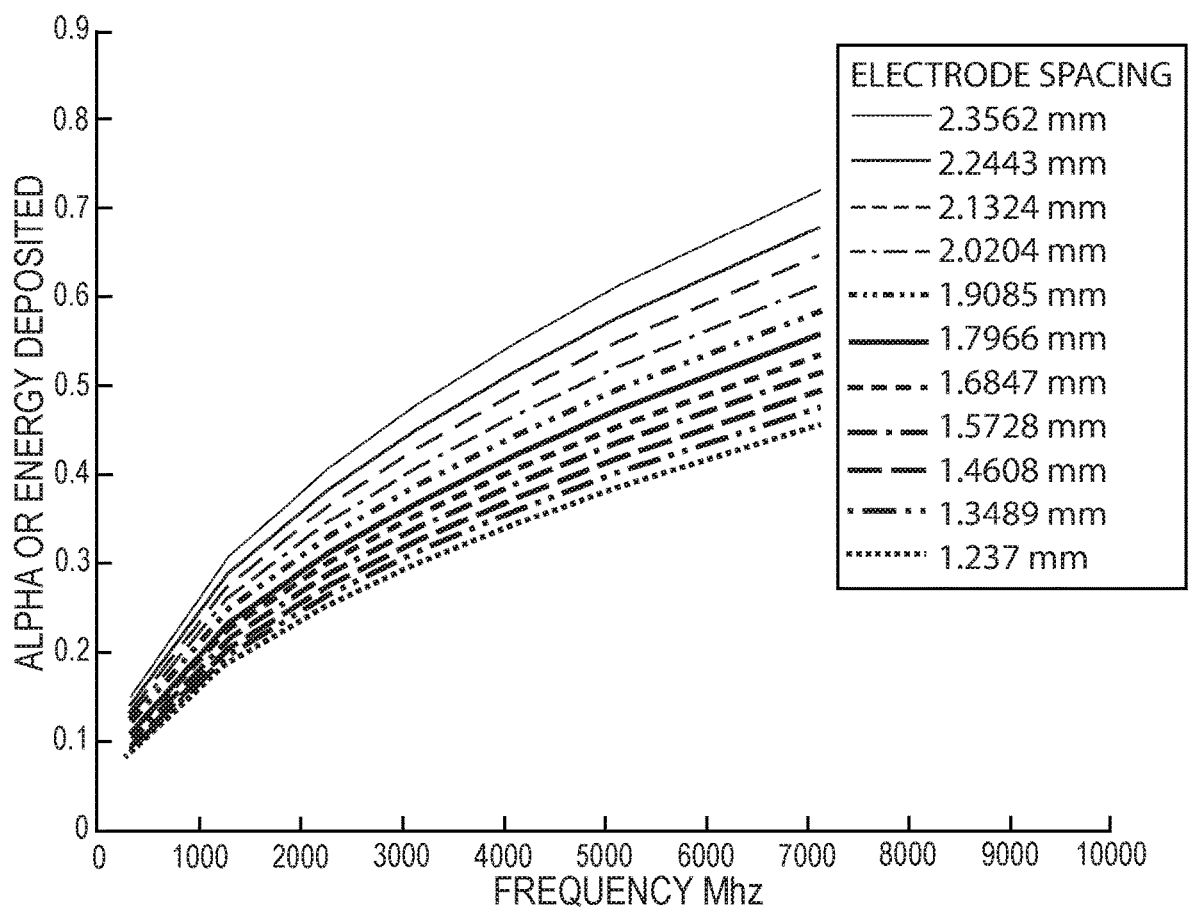
FIG. 16 is a graph of the calculated data of Table 1, showing Attenuation (a) vs. Frequency (MHz) for various circumferential interelectrode spacings.

FIG. 16 is a graph of the calculated data of Table 1, showing Attenuation (α) vs. Frequency (MHz) for various circumferential interelectrode spacings, with 2.36 mm circumferential interelectrode spacing corresponding to the lowest curve shown in FIG. 16 and 1.237 mm circumferential interelectrode spacing corresponding to the highest curve shown in FIG. 16. Graphs similar to that shown in FIG. 16 could be generated for Tables 2-3.

Similar to the calculated data for a variable circumferential interelectrode spacing as shown and described with respect to FIGS. 15-16 and Tables 1-3, the strip-line approach shown in FIG. 5D yields the calculated attenuation data shown in Table 4, for a configuration that includes a single strip line electrode trace ($e_1$), of width 0.25 mm and thickness of 0.005 mm, sandwiched between two ground planes ($G_1$, $G_2$) and separated from each such ground plane by about 1.25 mm (or other value, e.g., between 2-5 times the electrode linewidth of 0.25 mm) such as to help avoid coupling to the ground planes.

TABLE 4

Attenuation (α) vs. Substrate Conductance (σ, S/m) and Frequency
(GHz) for a strip-line configuration, such as shown in FIGS. 5D-5E

| σ (S/m) | Freq 10 GHz | Freq 9.03 GHz | Freq 8.06 GHz | Freq 7.09 GHz | Freq 6.12 GHz | Freq 5.15 GHz | Freq 4.18 GHz | Freq 3.21 GHz | Freq 2.24 GHz | Freq 1.27 GHz | Freq 0.3 GHz |
|---|---|---|---|---|---|---|---|---|---|---|---|
| 10.0 | 3834 | 3643 | 3442 | 3228 | 2999 | 2751 | 2479 | 2172 | 1815 | 1366 | 664 |
| 5.0 | 1917 | 1822 | 1721 | 1614 | 1500 | 1376 | 1239 | 1086 | 907 | 683 | 332 |
| 2.5 | 767 | 729 | 688 | 646 | 600 | 550 | 496 | 434 | 363 | 273 | 133 |

In Table 4, it is seen that higher frequencies yield more attenuation, power deposition, and substrate heat generation than lower frequencies, and that higher substrate conductivity yields more attenuation, power deposition, and substrate heat generation than lower substrate conductivity. Thus, for a given substrate conductivity, the frequency of the electrical input signal applied to the strip-line can be selected to achieve a desired amount of heat deposition for a given strip-line.

"Sweep" Technique of Frequency-Control of Active Heat Sources of Catheter

A "sweep" technique can provide programmable and adaptive control of the various active heat sources of the catheter such as to help sterilize one or more desired portions of the catheter. The sweep can be managed such that the addition of thermal energy into the subject creates short-lived perturbations to the subject's metabolic equilibrium, such as with each individual perturbation being within the subject's metabolic tolerance. The sweep can also be managed such as to help ensure that there is no residual or cumulative adverse effect to the subject resulting from in vivo heat sterilization of the catheter.

Some terminology used in describing the sweep techniques is explained below. "Sterilization temperature" can refer to the temperature needed for effective sterilization of one or more pathogens of interest. The sterilization temperature can vary, such as with the particular species of the specified at least one pathogen. "Sterilization duration" can refer to the time period for which the sterilization temperature is to be maintained to enable complete sterilization of the specified at at one pathogen. "Clearance rate" can refer to a rate of extraction of heat from the catheter, such as by surrounding fluid flow (e.g., such as when the catheter is located within a blood vessel, for example), by nearby tissue, or by one or more other anatomical structures. "Time to equilibrium" can refer to a time duration after application of a sterilization grade temperature before the system (thermal and metabolic) comes back to its equilibrium point or original state. "Activation delay" can refer to a time between two successive activations of a given heat source on the catheter. "Sweep repetition rate" can refer to the number of times that the catheter must be sterilized of one or more pathogens or biofilm over a specified time period, such as a day. "Location in subject" can refer to an anatomical location in the subject's body. "Scan pattern" can refer to a predefined or specified pattern activation of heat sources of the catheter. A scan pattern can be established such as to help ensure complete coverage of a desired catheter heating zone. The scan pattern can be specific or unique to each particular catheter layout, or specific or unique to such layout in combination with an application or location of the catheter to the subject. A scan pattern can include one or more functions other than heat sterilization, such as, for example, can include mechanical vibration or movement. Such mechanical vibration or movement can include a piezoelectric actuator or other device such as can help dislodge or lift off biofilm from the catheter, such as biofilm that has been heat sterilized to address or neutralize one or more pathogens. "End marker" can refer to a location along the length of the catheter that exits a fluid flow region (e.g., such as a blood vessel), such as a fluid flow region in which a portion of the catheter is located. A sweep can execute the scan pattern safely, such as explained further below.

Figure 17:
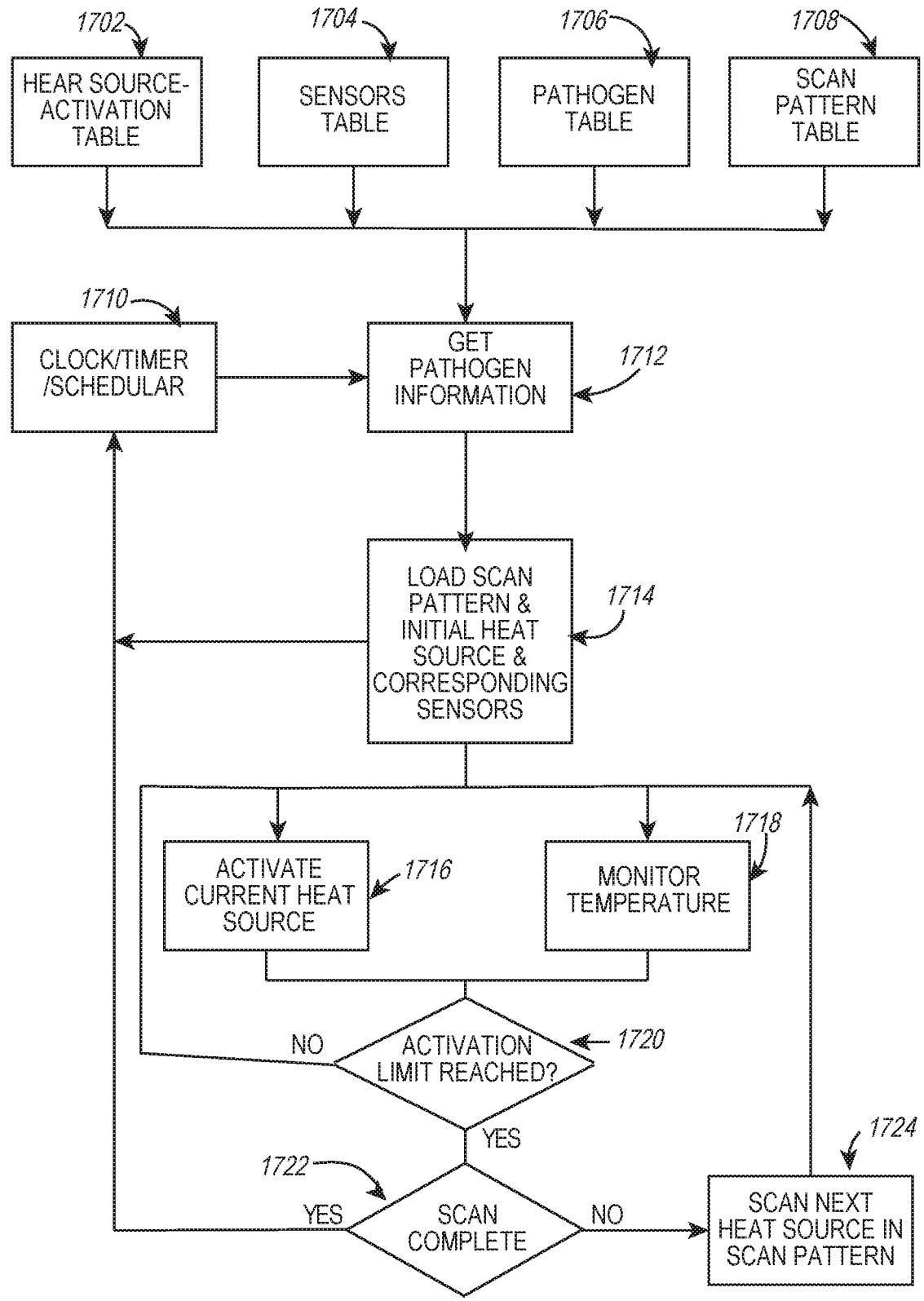
FIG. 17 is a diagram that shows an example of a technique for sweeping across various heat sources that can be distributed at various locations within one or more heating zones that can be located on a catheter.

FIG. 17 is a diagram that shows an example of a technique for sweeping across various heat sources that can be distributed at various locations within one or more heating zones that can be located on a catheter. Such heat sources can be frequency-addressable, such as to selectively apply heat to inhibit or neutralize one or more pathogens. Such applied heat can help inhibit or prevent a biofilm from forming on the catheter, which can lead to potential infection. By sweeping across various localized heat sources on the catheter, the corresponding in vivo locations of such localized heat sources can be increased in temperature to a temperature value for a sufficient duration to provide localized pathogen inhibition or neutralization, without creating excessive heat that may adversely affect nearby biological tissue.

The sweep technique can be initialized or configured using information stored in memory circuitry such as can be included in or accessed by the controller circuitry 202. Such stored initialization or configuration information can include a heat source activation table 1702, a sensor table 1704, a pathogen table 1706, and a scan pattern table 1708, such as shown in FIG. 17. Clock/timer/scheduler circuitry 1710 can also be included, such as to schedule execution of one or more scan patterns or to time heat source activation and duration during execution of a particular scan pattern, as explained below.

The heat source activation table 1702 can include addressing and control information for the particular catheter design. For frequency controlled activation of multiple heat sources being addressed using a shared pair of electrical interconnection lines (e.g., such as V+ and V− heating RF control lines 302A-B), the heat source activation table 1702 can include information such as: sweep repetition rate; addressing frequency (or frequency range) of various individual heat sources (e.g., electrodes, planar resonator cavities, strip-lines, etc.); specified locations of the various heat sources on the catheter; and at least one default temperature rate of change per unit time for the various heat sources.

The sensor table 1704 can include information such as: specified temperature (or other sensor) locations; sensor calibration value; sensor activation technique; sensor activation frequency; and sweep activation repetition rate.

The pathogen table 1706 can include information such as: pathogen name or identifier, such as of one or a specified combination of pathogens; and, corresponding sterilization temperature and sterilization duration.

The scan pattern table 1708 can include information such as: a sequence of triggering of heat sources according to a predefined or specified scan pattern. In an example, the scan pattern can be adaptive, such as based upon input from one or more temperature or other sensors. The scan pattern can be adjusted such as to reduce or minimize temperature instability that may interfere with the subject's metabolic capacity or tolerance.

At 1710, clock/timer/scheduler circuitry can provide an appropriately-timed indication that a particular scan pattern is scheduled for execution. For example multiple same or different scan patterns can be scheduled daily, such as to address the same or different combinations of one or more potential pathogens that are determined or expected to be present.

At 1712, pathogen information can be retrieved from the pathogen table, such as either in response to the clock/timer/scheduler circuitry indicating that a particular scan pattern is scheduled for execution, or independently, such as in a one-time or recurrent fashion, such as in response to biopsy sample analysis results or other user-input indicating which one or more pathogens of interest are to be inhibited, neutralized, or sterilized. The retrieved pathogen information can include one or more of the pathogen name or identifier, such as of one or a specified combination of pathogens, and a corresponding sterilization or other treatment temperature and duration.

At 1714, scan pattern information can be retrieved or loaded from the scan pattern table 1708, such as indicating which scan pattern across which heat sources is to be executed. The scan pattern can be selected in response to the retrieve pathogen information, such that the scan pattern can be specific to a particular pathogen or combination of pathogens expected or determined to be present. The scan pattern can indicate which heat sources are to be activated, in which order such heat sources are to be activated, and the target sterilization temperature and duration to be achieved at the locations on the catheter corresponding to such heat sources. For individual heat sources to be activated according to the scan pattern, information can be retrieved from the sensors table 1704, for example, indicating which one or more temperature sensors are located closest to the particular heat source to be activated within the scan pattern.

At 1716, during execution of a particular scan pattern, a selected heat source can be activated, such as using one or more of the frequency-controlled addressing techniques described herein. Meanwhile, at 1718, one or more corresponding temperature sensors (e.g., closest to the selected heat source being activated) can be activated concurrently or in temporal association with activation of the selected heat source. This can help perform an initial temperature reading, for example, upon which activation of the selected heat source can be conditioned. For example, if an initial temperature reading exceeds a sterilization temperature or other limit value, then activation of the corresponding heat source can be inhibited. The temperature monitoring can continue during the activation of the selected heat source, such as to compare an ongoing temperature reading to the sterilization temperature of other limit value, and to deactivate the selected heat source when the temperature exceeds the sterilization temperature or other limit value. In an example, only one selected heat source on the catheter is activated at a time during execution of the scan pattern. In another example, multiple heat sources on the catheter can be simultaneously or concurrently activated during execution of a scan pattern, with the different concurrently activated heat sources being associated with the same or different temperature sensors such as to individually or collectively control deactivation of such concurrently activated heat sources.

At 1720, it can be determined whether a heat source activation limit has been reached. This can include determining whether a sterilization temperature has been exceeded, whether the sterilization temperature has been maintained for a duration that exceeds a specified sterilization duration, or both. If the sterilization temperature has not been exceeded and the sterilization duration has not timed out, continued heating by the selected heat source at 1716 and continued temperature monitoring at 1718 by a corresponding temperature sensor can continue. If the sterilization temperature has been exceeded but the sterilization duration has not been exceeded, the selected heat source can be temporarily deactivated and temperature monitoring can be continued at 1718 to determine when the temperature has decreased sufficiently to reactivate that heat source during the same sterilization duration period. If the sterilization temperature has been maintained for an adequate time period in accordance with the specified sterilization duration period, then at 1722 it can be determined whether the scan is complete.

At 1722, determining whether the scan is complete can include determining whether there are other heat sources in the scan pattern that are yet to be activated. If no other heat sources in the scan pattern remain to be scanned, then the scan can be deemed complete at 1722, and the process can wait for a subsequent time at which the clock/timer/scheduler circuitry indicates that another (same or different) scan pattern is to be executed. If other heat sources in the scan pattern remain to be activated, then at 1722, the scan can be deemed incomplete, and at 1724, the next one or more heat sources in the scan pattern to be activated can be selected, and process flow can return to the concurrent heat source activation 1726 and temperature monitoring at 1718, to be carried out such as described previously.

Resistive Heating Element Examples

The preceding description has focused on coupling energy into an active substrate such as for heat generation, such as by applying an electrical input signal to one or more of: at least one pair of variable spacing electrodes, at least one planar resonator, at least one strip line, or the like. These various techniques are advantageous in that they allow frequency controlled addressing of such individual localized structures via an electrical input signal, which, in turn, can couple energy into an active substrate at a desired location for heat generation at that location, allowing the location to be selectable via selection of the frequency of the applied electrical input signal. This can provide localized heating without requiring running individual electrical conducting traces from such individualized localized structures, e.g., such as near the distal end of an implantable medical device such as a catheter 100 back to the proximal end of the implantable medical device for selective application of the electrical input signal to only those structures to be selectively addressed and activated, or without requiring on-board switching circuitry to be included on a distal portion of the medical device itself.

Figures 18A, 18B:
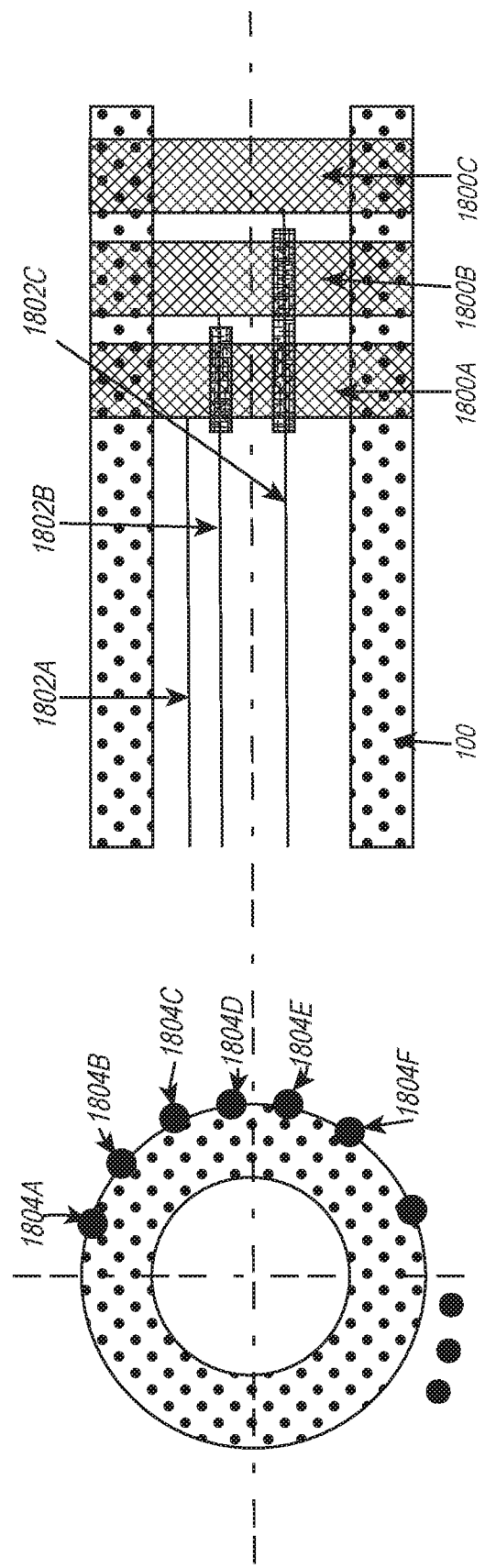
FIGS. 18A, 18B shows an example of a distal or other portion of a catheter, such as can include one or a plurality of resistive heating elements that can be spaced apart as desired at different longitudinal locations along a length of the portion of the catheter.

Nonetheless, it is possible to additionally or alternatively include a plurality of localized resistive heat elements at desired selectively addressable locations on the implantable medical device, such as on or toward a distal portion of the catheter 100, together with individualized electrical traces that can extend back toward a proximal end of medical device, which can be located external to the patient, and which can be selectively connected to an external signal source for providing energy to such localized resistive heating elements, such as shown and described in the example of FIGS. 18A and 18B.

FIG. 18A shows an example of a distal or other portion of a catheter 100, such as can include one or a plurality of resistive heating elements 1800 that can be spaced apart as desired at different longitudinal locations along a length of the portion of the catheter 100. The resistive heating elements 1800 can include contacts, strips, or bands, such as, in an example, can fully or partially extend circumferentially around the catheter 100, such as to provide heat circumferentially about the catheter 100 at the location of the band. In an example, all or a group of the resistive heating elements 1800 can be electrically connected via a shared grounding electrical trace that extends proximally along a length of the catheter to a proximal end of the catheter 100, for allowing external electrical interconnection thereto, while an individual or one or more groups of the resistive heating elements 1800 can be electrically connected by a dedicated electrical trace that extends proximally along a length of the catheter to the proximal end of the catheter, such as for allowing individualized electrical interconnection thereto. In this way, individual ones (or pre-connected groups) of the resistive heating elements 1800 can be selectively activated to provide localized heat generated at the corresponding locations of such resistive heating elements.

The resistive heating elements 1800 can include or consist of a high resistance material for generating heat, such as Nichrome or the like. The electrical interconnections extending from these heating elements toward a proximal end of the catheter 100 or other device can include a highly electrical conductive material (e.g., of much lower electrical resistance relative to that of the resistive heating elements 1800) such that the electrical connection does not heat substantially while conducting electrical energy to the selected resistive heating elements.

As shown in the proximal end view of FIG. 18B, at a proximal end of the catheter, the electrical interconnection traces 1802 can be circumferentially distributed and electrically interconnected to corresponding electrical contacts 1804, such as can be contacted by a corresponding external circumferential connector, which, in turn, can be connected to a switching matrix, a DC power source, or the like. In an illustrative example, a catheter may include 10, 20, or even 30 or more such circumferentially distributed contacts 1804 that can be electrically connected to the corresponding interconnection lines for corresponding individualized (or designated addressable groups) of resistive heating elements 1800, with at least one or more such contacts 1804 reserved for a ground line such as can be shared by various individual or groups of the resistive heating elements 1800.

Figure 18C:
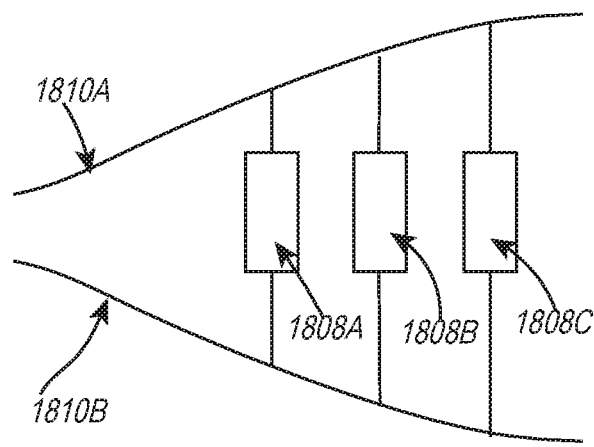
FIG. 18C shows an illustrative example that can combine an approach of using resistive elements in combination with some level of frequency control that can be provided using at least one pair of variable spacing conductive electrodes.

FIG. 18C shows an illustrative example that can combine an approach of using resistive elements 1808 in combination with some level of frequency control that can be provided using at least one pair of variable spacing conductive electrodes 1810. In FIG. 18C, co-planar or cylindrically co-planar variable spacing electrically conductive electrodes 1810A-B (e.g., made of copper, gold, or the like) can be arranged with a variable separation distance therebetween. At selected locations, such as can correspond to different interelectrode separation distances, one or more resistive heating elements 1808A, 1808B, 1808C, etc., (e.g., made of nichrome or other highly resistive trace heating element) can be electrically interconnected between the electrodes 1810A-B. The frequency of an electrical signal applied to the electrodes 1810 can be adjusted or selected to preferentially direct more energy to one or more of the resistive heat elements 1808 relative to the other resistive heating elements, thereby allowing a degree of frequency control over localized heat generation by the resistive elements 1808. This, in turn, can allow a heat gradient to be established between different resistive elements 1808.

Thus, in FIG. 18C thin nichrome wires or other resistive traces can be placed across the electrically conductive electrodes, which electrodes can be arranged with respect to each other such as to have a variable spacing therebetween at different portions of the electrodes. Changing the frequency of the input electrical signal changes the amount of current passing though the resistive nichrome wires or other resistive traces, thus creates heat and varies the location and amount of heat being applied. Additionally or alternatively, a coarse matrix of loops of a nichrome wire or other resistive trace can be placed on the catheter and DC current can selectively be passed therethrough, such as where localization using frequency control is not needed. In an example, the electrical current can include a DC current, which can be used if heat generation without localization is desired.

Figure 19:
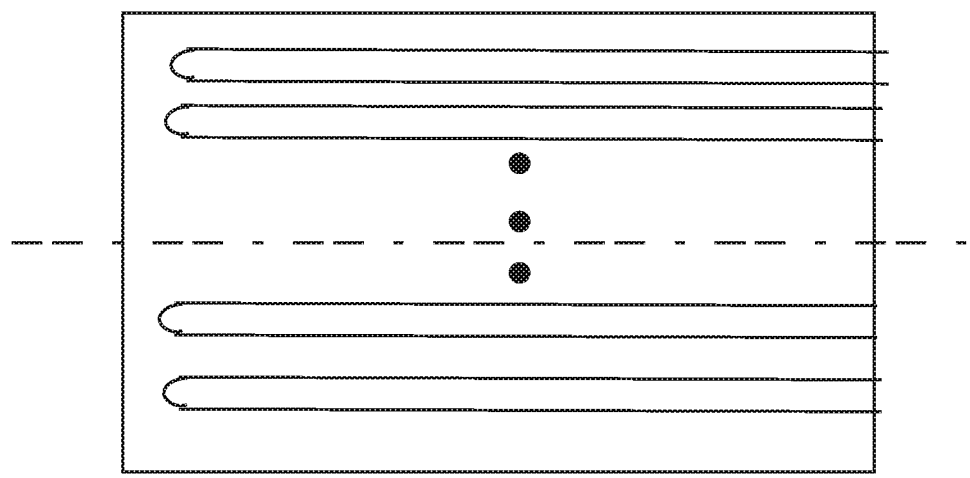
FIG. 19 shows an illustrative example in which the heating device on the catheter can include one or more electrically resistive serpentine or other bends or loops, such as through which an AC or DC electrical current can be passed to generate heat.

FIG. 19 shows an illustrative example in which the heating device on the catheter 100 can include one or more electrically resistive (e.g., nichrome) serpentine or other bends or loops, such as through which an AC or DC electrical current can be passed to generate heat. A matrix of such loops can be created to provide localized heat sources.

Figure 20A:
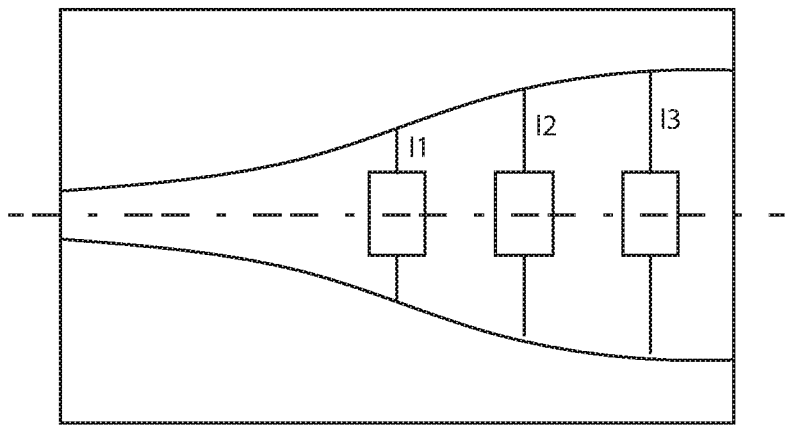
FIGS. 20A, 20B, and 20C show further examples of resistive trace heating.
Figure 20B:
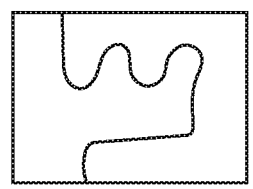
Figure 20C:
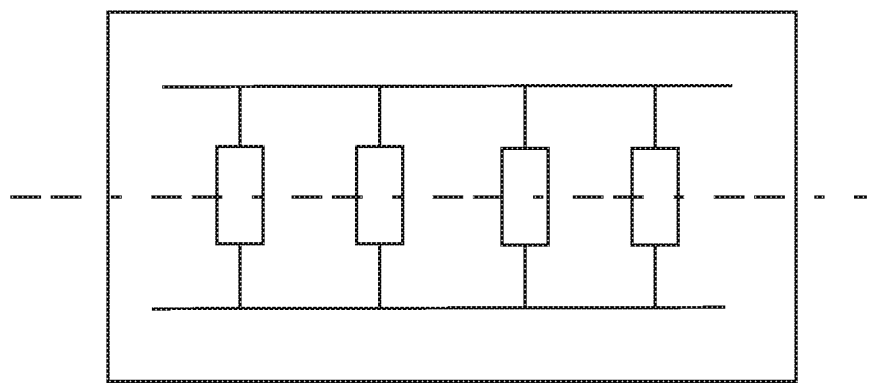

FIGS. 20A, 20B, and 20C show further examples of nichrome wire (or other resistive trace) based heating, such as in response to an AC or DC electrical input signal, in which the nichrome or other trace can be placed on a dielectric such as to avoid forming a short circuit with the conductive electrodes. The length, thickness, and width of the nichrome or other trace resistive heating elements can be specified to accommodate the desired heating performance for each nichrome or other trace heating element or group of such heating elements.

FIG. 20A shows an illustrative example of a pair of variable spacing conductive electrodes (e.g., copper or gold) between which one or more individual nichrome or other trace resistive heating elements can be positioned at different locations along the variable spacing between the electrically conductive electrodes. If a DC electromagnetic signal is applied to the structure shown in FIG. 20A, current division will occur as determined by the parallel combination of resistive heating elements interposed between the variable spacing electrodes. If an AC electromagnetic signal is applied to the structure shown in FIG. 20A, current division will also depend on the spacing between the variable spacing electrodes, such that by selecting a particular frequency of applied AC electromagnetic input signal, power and heat generation can be selectively focused using the resistive heating paths provided by one or more selected ones of of the resistive heating elements.

FIG. 20B shows an illustrative example in which a meandering nichrome or other trace resistive heating element can be used to provide heating at a desired location, such as in response to an AC or DC electrical input signal.

FIG. 20C shows an illustrative example in which one or more individual nichrome or other trace resistive heating elements can be positioned at different locations between electrically conductive electrodes, with a constant spacing between such electrodes, such as in an example in which frequency control to adjust heating location is not desired, thereby allowing a constant spacing between the electrodes in a pair of electrodes.

Mechanical Transducer Examples

Figure 21A:
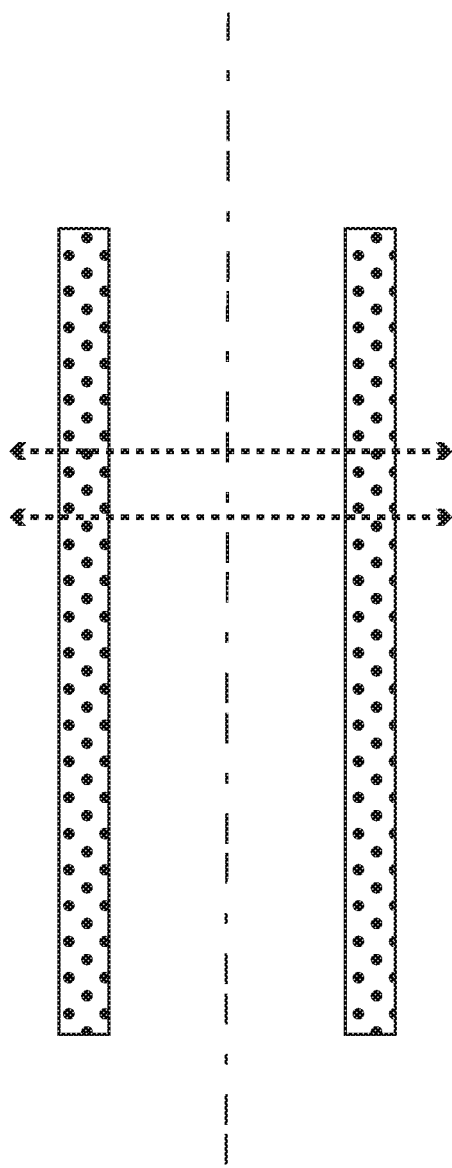
Figure 21C:
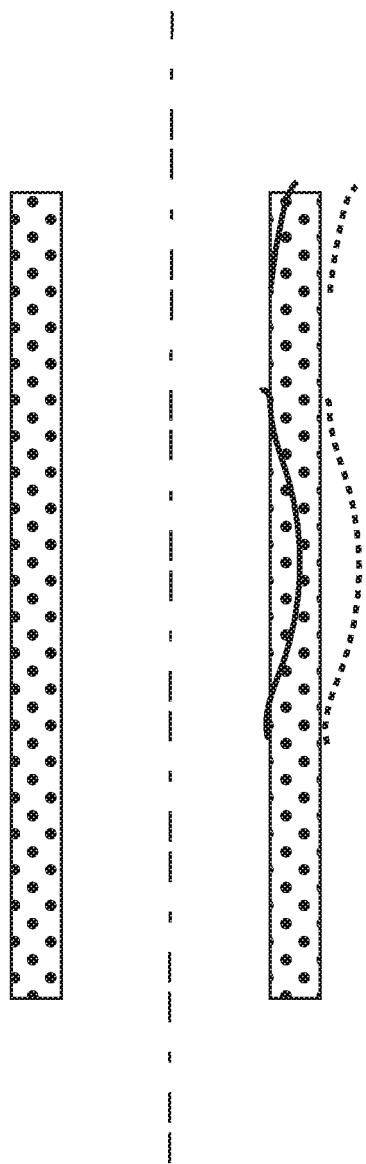

FIGS. 21A, 21B, and 21C (cross-sectional side views) show illustrative examples of piezoelectric elements or other mechanical output transducers such as can optionally be included at one or more select locations along the length of the catheter 100, such as can provide a mechanical force or movement, such as one or more of vibration (e.g., FIG. 21A), lifting (e.g., FIG. 21B), or bending (e.g., FIG. 21C) of a desired portion of the catheter 100. In an example, such mechanical force or movement can help reduce contact between a heated portion of the catheter 100 and healthy tissue in contact with the catheter 100. In another example, such mechanical force or movement can help dislodge a clog or disrupt a biofilm along an exterior surface of the catheter 100 or within an interior fluid conduit provided by the catheter 100. In another example, such mechanical force or movement can help slough off heat-neutralized biofilm.

In an example, bending can be effected by establishing a temperature gradient, such as can be provided using one or more of a pair of variable spacing electrodes, a planar resonator, a strip-line, a micro-stripline, a micro-stripline waveguide, a resistive heating element, such as described herein, or a piezoelectric or other heating element. By placing into adjacency dissimilar metals or other materials or layers that have different thermal expansion rates, mechanically constrained from being able to extend outward, buckling can be induced at the interface between such different materials or layers such as by providing heat to such materials having different thermal expansion rates, or providing a heat gradient across such materials having the same or different thermal expansion rates. Such buckling can be used to cause bending of the catheter 100, which, in turn can effect lifting off at the hottest location being provided, such as the location (e.g., selected using frequency-control of the electrical input signal) being heat-treated or heat-sterilized. Such localized lifting off can displace such portion of the catheter 100 away from nearby tissue in a situation in which it is desired to avoid excessive heating of such nearby tissue by direct or close contact with a local heat source on the catheter, or to display such portion of the catheter 100 toward a target location to which direct or close contact is desired to promote heating of such nearby tissue or other target.

For in-vivo biofilm inhibition, disruption, or sterilization, the one or both of the heating device or the mechanical transducer device such as described herein can be built into a catheter 100 or it can be added to an existing OEM catheter 100. Each patient's size, medical condition, and anatomical features vary and, therefore, so may the length, diameter, or other physical characteristic of the catheter 100 that can be at least partially inserted or at least partially implanted into the patient. Thus, the longitudinal placement location and length of the heating device 200 on the catheter 100 can vary based on the particular catheter type, the application of the catheter 100, or upon one or more characteristics of the patient or the patient's health status. As explained elsewhere herein, the present approach can permit the catheter 100 to be cut down to a desired size to fit a particular patient or application, while still functioning to provide localized heat, as desired, since the configuration does not require the presence of more distal electrical conduction traces to complete an electrical circuit. This allows the catheter 100 to be cut down to a desired length.

After at least a distal portion of the catheter 100 is implanted or introduced percutaneously or otherwise into the body of the patient, a proximal portion of the catheter 100 can then be connected to a control unit and a power supply. The control unit can recurrently or periodically wake up or otherwise conduct an in-vivo heat treatment or heat sterilization sweep of all or a specified region of the catheter. In an example, one or more physical, biological, or other parameters can concurrently be sensed or recorded in or around the catheter 100.

Catheter placement guidance is useful aspect of the present approach. Without imaging assistance, catheter placement can be complex and may impact patient tissue or cause other side-effects to the patient. By providing one or more piezoelectric or other sensors, e.g., at a distal tip of the catheter 100, sensor data feedback can be used during catheter introduction and placement, such as to help assist with proper placement, to verify proper or desired placement, or both.

An optional sealing layer 201 can be provided. In an example, this sealing layer 201 should be a good conductor of heat. It can also be semi-porous or flexible. Heat, piezoelectric vibration, or one or more other mechanisms can be used to produce surface movement of a desired portion of the catheter 100. Such surface movement can be used to physically shake off dead biofilm cells, which, in turn, can help promote thermal sterilization or treatment efficiency. In an example, a porous sealant layer such as graphene can be provided, such as can be used to create movement in the layer. Such movement can also have the effect of shaking off dead bio-film. A single layer or micro thin shaker can thus be provided. The shaker can vibrate at the frequency of the electrical input signal being applied thereto. Differential expansion and movement can also be provided, such as to create desired undulations in the catheter 100, such as to lift it off of or away from an adjacent vascular surface. This can help reduce or minimize the in-vivo heat treatment or sterilization from causing damage to vascular or other tissue lining with which the catheter 100 may come in contact.

FIG. 21B shows an example that can create or provide one or more temporally dynamic O-Ring like structures on either side of the area that is being heat-sterilized or otherwise treated. This can be accomplished by pushing out the catheter material, such as for bending it such as to produce a temporally dynamic O-ring. In the example of FIG. 21B, variable spacing electrode pairs 2101 and 2102 can be located on the catheter such that the variable spacing electrode pair 2101 has its closest interelectrode spacing located at a dynamic O-ring 2102A region of the catheter 100, while the variable spacing electrode pair 2102 has its closest interelectrode spacing located at a dynamic O-ring 2102B region of the catheter 100. By concurrently actuating the electrode pairs 2101 and 2102, the locations of closest interelectrode spacing, corresponding to the dynamic O-rings 2102A, 2102B, can be heated to a temperature that is hotter than the intermediate region therebetween, which corresponds to a larger interelectrode spacing for both of the electrode pairs 2101 and 2102. Therefore, such intermediate region between the dynamic O-rings 2102A, 2102B can be heated to a temperature value that is less than the temperature value at the dynamic O-rings 2102A, 2102B. Thus, the dynamic O-rings 2102A, 2102 will expand and push circumferentially outward, and because of the thermal gradients so established, will do so to a greater degree than the intermediate region therebetween, and to a greater degree than cooler regions more proximal from or more distal to the O-rings 2102A, 2102B. The thermal expansion can be enhanced by selecting a material of or on the catheter 100 at the locations of the O-rings 2102A, 2102B that is susceptible to thermal expansion. In an example, the locations of the O-rings 2102A, 2102B can be coated with a thermally insulative material. This can protect adjacent tissue from being excessively heated when the O-rings 2102A, 2102B are expanded. It can also help enhance the thermal expansion of the O-rings 2102A, 2102B, such as by thermally confining more heat within the material of the O-rings 2102A, 2102B, or by providing a material with a greater coefficient of thermal expansion at the desired locations of the O-rings 2102A, 2102B.

Another approach is to place a layer that contains a balloon-like ring that can be inflated such as can blows up slightly such as to form toroidal ridge or O-ring around the heated area, such as to help thermally confine the region being heated.

In an example, one or more pressure sensors can be included at one or more desired locations of the catheter 100, such as to help measure and determine fluid constriction within the interior fluid conduit of the catheter 100, such as can occur when one or more layers of dead biofilm have accumulated in regions in, on, or around the catheter 100. Mechanical, thermal, or chemical approaches can leverage such information for use in being applied in a localized fashion to inhibit, disrupt, treat, or sterilize away biofilm or the like.

Example of Sweep Operation

Figure 22A:
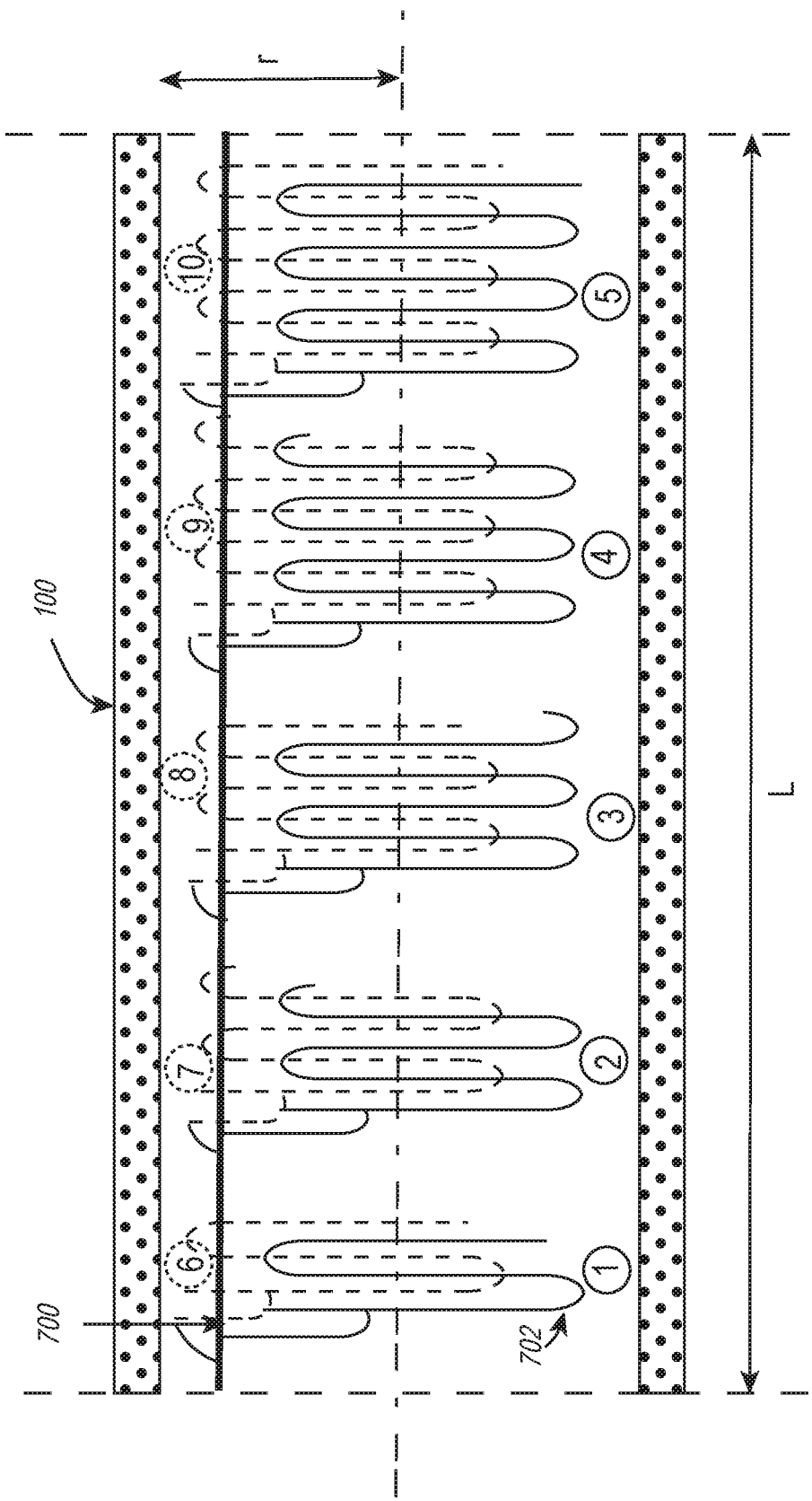
FIG. 22A (side view), FIG. 22B (top view of an unrolled cylindrically planar surface), and FIG. 22C (grid view) show a catheter including a heating zone of length, L, in which a number of planar transmission line resonators can be located.

FIGS. 22A (side view) and 22B (top view of an unrolled cylindrically planar surface) show a catheter 100 of cylindrical radius, r, including a heating zone of length, L, in which a number of planar transmission line resonators can be located, such as can be connected to a shared main line 700 such as for applying an electrical input signal for selectively temporally actuating ones of the planar resonators 702 such as to neutralize a pathogen by dynamically creating a heat source in an adjacent active substrate portion of the catheter 100. In this illustrative example, ten planar resonators (T1, . . . , T10) are shown, such as five planar resonators on a first side of the catheter 100, shown in solid lines, and another five planar resonators on an opposing second side of the catheter 100, shown in dashed lines.

FIG. 22C shows a simplified top view of the unrolled cylindrically planar surface of the catheter 100 showing a grid indicating the general arrangement of the ten planar resonators (T1, . . . , T10) together with their corresponding resonance frequencies that can be used to selectively address and actuate the planar resonators T1, . . . , T10, either individually, or in groups. Different planar resonators having different resonance frequencies can optionally be concurrently addressed by a shared electrical signal provided on a main line to all or a group of the planar resonators, such as by including a superpositioned or other electrical input signal having frequency components at the different resonance frequencies of the planar resonators to be concurrently addressed. Moreover, these different frequency components need not have the same power level, but can optionally be provided with different power levels at such respective frequencies.

Figure 22B:
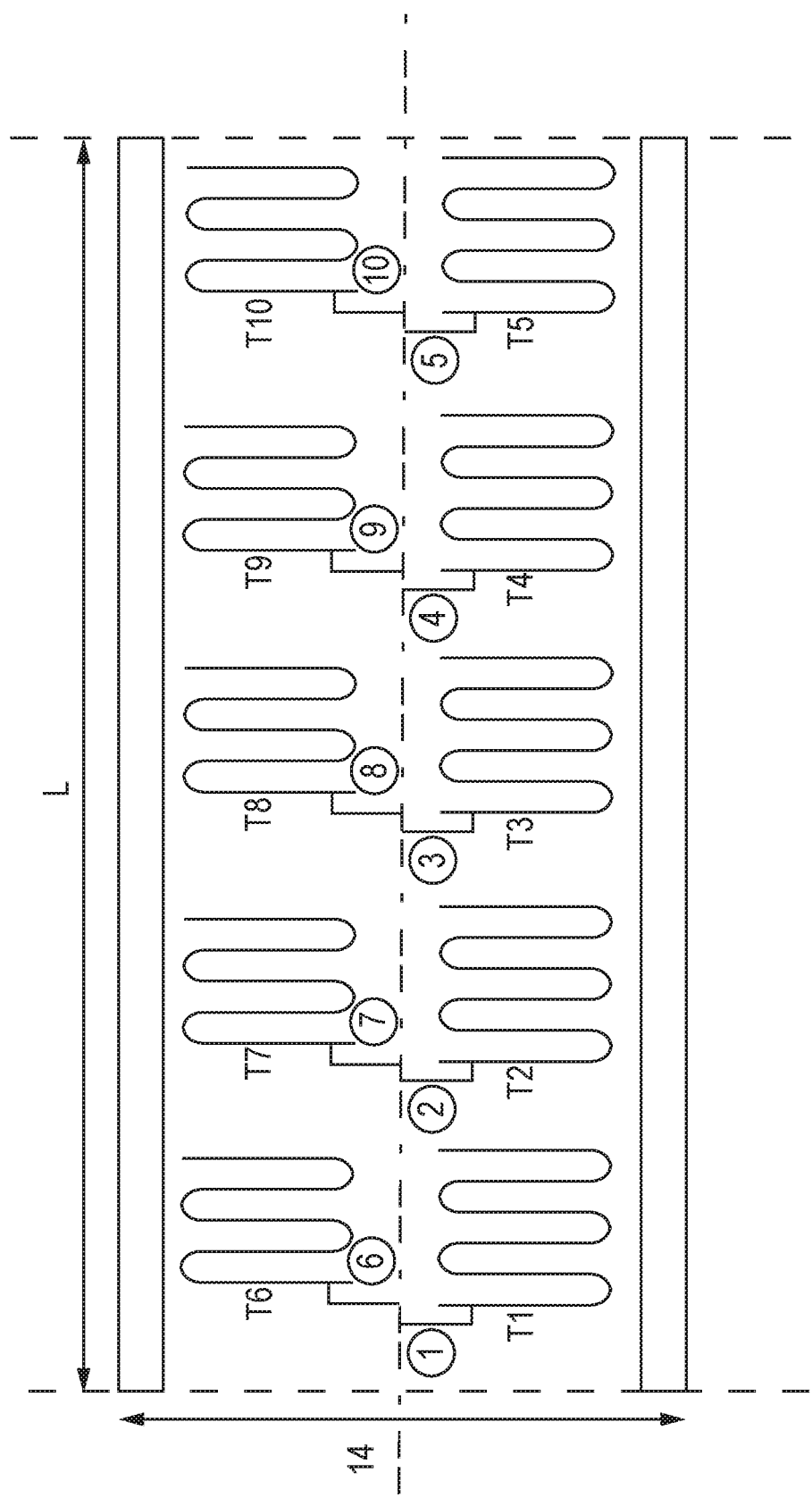

In an illustrative, non-limiting heat sterilization application using an arrangement such as shown in FIGS. 22A-22C to treat *Staphylococcus epidermidis*, for example, effective heat sterilization will occur at a sterilization target temperature of 45° C. to 50° C. The present example can be used to maintain a specified region or heat zone at such sterilization target temperature of 45° C. to 50° C. for a cumulative time duration of 30 minutes, such as can be achieved in 60 bursts of 30 seconds each.

In an illustrative, non-limiting example, a sweep can be configured to temporally sequentially selectively activate individual ones of planar resonators in 30 second bursts. In an example, this can be carried out in a manner to effect a temperature gradient differential of 10° C. between a selected "hottest" sterilizing planar resonator region and its neighboring planar resonator regions, which can optionally also be maintained during such time periods at a heated temperature that is not quite as hot as the selected "hottest" sterilizing planar resonator region.

Before initiating the temperature activation sweep, a temperature measurement of the various locations T1, . . . , T10 on the grid can be performed, with the resulting measurements stored in memory circuitry. A safety test can then be performed to compare the measured temperatures against biological tolerance values, to ensure that when the heat sterilization sweep is initiated, the various locations T1, . . . , T10 on the grid are at temperatures that are within a specified biological tolerance of nearby tissue. If so, temperature activation sweep of the planar resonators T1, . . . , T10 on the grid can proceed.

At step 1 of the sweep, an electrical input signal with frequency components at 1.0 GHz, 2.0 GHz, and 1.1 GHz can be applied to the main line that is electrically connected or capacitively coupled to the planar resonators T1, . . . , T10. This activates the planar resonators T1, T2, and T6. The power levels of the electrical input signal components at 2.0 GHz and 1.1 GHz can be kept less than the power level of the electrical input signal component at 1.0 GHz, such as to establish or maintain a temperature of 50° C. in the active substrate at the planar resonator T1, while concurrently establishing or maintaining a temperature of 40° C. in the active substrate at the planar resonators T2, T6, with the other planar resonators T3, T4, T5, T7, T8, T9, T10 not generating any heat and, therefore, remaining at body temperature of 37° C. This state is illustrated in Table 5.

TABLE 5

Status during Step 1 (first 30 second burst) of Sweep

| T6 = 40° C. | T7 = 37° C. | T8 = 37° C. | T9 = 37° C. | T10 = 37° C. |
|---|---|---|---|---|
| T1 = 50° C. | T2 = 40° C. | T3 = 37° C. | T4 = 37° C. | T5 = 37° C. |

At step 2 of the sweep, an electrical input signal with frequency components at 1.0 GHz, 1.1 GHz, 1.2 GHz, 2.0 GHz, 2.2 GHz, and 2.4 GHz can be applied to the main line that is electrically connected or capacitively coupled to the planar resonators T1, . . . , T10. This activates the planar resonators T1, T2, T3, T6, T7, and T8. The power levels of the electrical input signal components at 1.0 GHz, 1.2 GHz, 2.0 GHz, 2.2 GHz, and 2.4 GHz GHz can be kept less than the power level of the electrical input signal component at 1.1 GHz, such as to establish or maintain a temperature of 50° C. in the active substrate at the planar resonator T2, while concurrently establishing or maintaining a temperature of 40° C. in the active substrate at the planar resonators T1, T3, T6, T7, and T8, with the other planar resonators T4, T5, T9, T10 not generating any heat and, therefore, remaining at body temperature of 37° C. This state is illustrated in Table 6.

TABLE 6

Status during Step 2 (second 30 second burst) of Sweep

| T6 = 40° C. | T7 = 40° C. | T8 = 40° C. | T9 = 37° C. | T10 = 37° C. |
|---|---|---|---|---|
| T1 = 40° C. | T2 = 50° C. | T3 = 40° C. | T4 = 37° C. | T5 = 37° C. |

At step 3 of the sweep, an electrical input signal with frequency components at 1.1 GHz, 1.2 GHz, 1.3 GHz, 2.2 GHz, 2.4 GHz, and 2.6 GHz can be applied to the main line that is electrically connected or capacitively coupled to the planar resonators T1, . . . , T10. This activates the planar resonators T2, T3, T4, T7, T8, and T9. The power levels of the electrical input signal components at 1.1 GHz, 1.3 GHz, 2.2 GHz, 2.4 GHz, and 2.6 GHz can be kept less than the power level of the electrical input signal component at 1.2 GHz, such as to establish or maintain a temperature of 50° C. in the active substrate at the planar resonator T3, while concurrently establishing or maintaining a temperature of 40° C. in the active substrate at the planar resonators T2, T4, T7, T8, and T9, with the other planar resonators T1, T6, T9, T10 not generating any heat and, therefore, remaining at body temperature of 37° C. This state is illustrated in Table 7.

TABLE 7

Status during Step 3 (third 30 second burst) of Sweep

| T6 = 37° C. | T7 = 40° C. | T8 = 40° C. | T9 = 40° C. | T10 = 37° C. |
|---|---|---|---|---|
| T1 = 37° C. | T2 = 40° C. | T3 = 50° C. | T4 = 40° C. | T5 = 37° C. |

The sweep can proceed in a similar manner through further steps to move the hot spot around in the grid, such as while optionally maintaining adjacent locations on the grid at a lesser elevated temperature above body temperature.

The sweep can be repeated until each location on the grid has achieved a desired sterilization temperature (e.g., 50° C.) for a cumulative time duration of 30 minutes, to neutralize the *Staphylococcus epidermidis* present in the heated zone spanned by the grid or matrix of planar resonators or other localized heat sources.

Although the above example has explained an approach to concurrently delivering different temperatures to different planar resonators in the grid/matrix by adjusting the power level of the electrical input signal components at those frequencies, additionally or alternatively, the desired frequency components can be applied with a specified relative duration or duty cycle relative to one or more other frequency components. For example, for the adjacent planar resonators that are desired to operate at a lower temperature than the "hot spot" planar resonator in the grid, the electrical input signal can establish or maintain such frequency components for a shorter interval than the 30 second burst, or can use a pulse-width or other modulation technique to intermittently activate those planar resonators that are desired to provide heat at a lesser temperature relative to a planar resonator that is more frequently activated to achieve a higher temperature. Such modulation techniques can use closed-loop control based on a sensed or measured temperature from a temperature sensor corresponding to or located near a particular planar resonator being intermittently operated or modulated.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A medical device that is at least partially insertable or implantable into a living human or animal subject to generate heat in vivo within the subject, the medical device comprising:

an elongate body, sized and shaped to include a biocompatible distal portion that is configured to be insertable or implantable into the subject; and a matrix of local heat sources, formed on the insertable or implantable biocompatible distal portion of the elongate body, the local heat sources selectively addressable and energizable in location individually or in groups by varying a frequency of an AC electromagnetic input signal delivered to the local heat sources from a proximal end of the elongate body, without requiring concurrent actuation of all of the local heat sources, wherein the local heat sources are selectively addressable and energizable individually or in groups in response to a specified frequency of the AC electromagnetic input signal having a variable frequency for the selectively addressing and energizing of the local heat sources and for using the same addressing and energizing AC electromagnetic input signal to also generate heat by energizing the local heat source; and wherein ones of the local heat sources include:
an electrical conductor, connected or coupled to receive the same AC electromagnetic input signal; and
a semiconductor, a lossy dielectric, thin-film metal, or a crystalline active substrate, arranged with respect to the electrical conductor to use the same addressing and energizing AC electromagnetic input signal to generate heat in the active substrate in response to the same AC electromagnetic input signal being at the specified frequency.

2. The medical device of claim 1, wherein the electrical conductor includes a pair of electrodes having a spacing therebetween, the spacing specified to allow heat to be generated using a time-varying electromagnetic input signal providing a variable frequency to control a variable location along the electrodes at which heat is generated in the active substrate.

3. The medical device of claim 1, wherein ones of the local heat sources are arranged as a planar resonator at different locations along a shared main line.

4. The medical device of claim 3, wherein the planar resonator includes at least one of:
the electrical conductor configured as a planar resonator line including a specified multiple of half-wavelengths ($\lambda/2$) in the substrate of a desired frequency of an electromagnetic input signal to be used to address the planar resonator in a non-grounded configuration;
or the electrical conductor configured as a planar resonator line including a specified multiple of quarter-wavelengths ($\lambda/4$) in the substrate of a desired frequency of an electromagnetic input signal to be used to address the planar resonator in a grounded configuration.

5. The medical device of claim 1, wherein ones of the local heat sources are arranged in a strip-line configuration at different locations along a shared main line.

6. The medical device of claim 1, wherein ones of the local heat sources are arranged with a capacitive coupling between the electrical conductor and the active substrate.

7. The medical device of claim 1, wherein the elongate body includes a catheter that includes an interior conduit capable of permitting fluid flow.

8. The medical device of claim 1, comprising a temperature sensor located on the elongate body at or near the matrix of heat sources, the temperature sensor providing a sensed temperature used to control the selective addressing and energizing of the heat sources in the matrix.

9. The medical device of claim 1, comprising a piezoelectric or other mechanical output transducer located on the elongate body on the biocompatible distal portion that is configured to be insertable or implantable into the subject.

10. A method of using a biocompatible medical device that is at least partially implantable into a living human or animal subject, the method comprising:

obtaining or providing the medical device including an elongate body including a matrix of local heat sources selectively addressable and energizable in location by varying a frequency of an AC electromagnetic input signal; and applying the same AC electromagnetic input signal to selectively address and energize local heat sources in the matrix to vary a location of locally generated heat without requiring concurrent energizing of all of the local heat sources in the matrix, the selectively addressing and energizing ones of the local heat sources in the matrix in response to a specified frequency of the same AC electromagnetic input signal having a variable frequency for the selectively addressing and energizing of the ones of the local heat sources and using the same AC electromagnetic input signal to generate heat by energizing the local heat source wherein ones of the local heat sources include:
an electrical conductor, connected or coupled to receive the same AC electromagnetic input signal; and
a semiconductor, a lossy dielectric, thin-film metal, or a crystalline active substrate, arranged with respect to the electrical conductor to use the same addressing and energizing AC electromagnetic input signal to generate heat in the active substrate in response to the same AC electromagnetic input signal being at the specified frequency.

11. The method of claim 10, comprising sweeping across the local heat sources individually or in groups to selectively energize ones of the local heat sources to attain a desired operating temperature at a first location for a desired first duration without exceeding a biological thermal budget at the first location, then selectively energizing ones of the local heat sources to attain a desired operating temperature at a different second location for a desired second duration without exceeding a biological thermal budget at the second location.

12. The method of claim 10, wherein the selectively energizing includes selecting a frequency of the time-varying electromagnetic input signal to control selection of a heat generation location within at least one of the heat sources.

13. The method of claim 10, comprising dynamically generating heat in the active substrate in response to the AC electromagnetic input signal applied to the electrical conductor.

14. The method of claim 13, comprising using the AC electromagnetic input signal to manage an electrical conduction within the active substrate for the dynamically generating heat in the active substrate.

15. The method of claim 10, further comprising controlling a location of heat generation within at least one of the local heat sources in the matrix of local heat sources.

16. The method of claim 10, wherein the ones of the local heat sources including at least one of: a pair of electrodes with variable interelectrode spacing, a planar resonator structure, or a strip-line structure.

17. The method of claim 10, comprising using ones of the local heat sources for providing an amount of heat to inhibit, disrupt, or sterilize a biofilm within, on, or adjacent to the elongate body, wherein the providing the amount of heat is less than an amount of heat to damage a biological tissue or fluid adjacent to or near the elongate body.

18. The method of claim 10, comprising using a sensed temperature to control the selective energizing of ones of the local heat sources in the matrix without requiring concurrent energizing of all of the local heat sources.

19. The method of claim 10, further comprising applying a DC or slowly varying AC positive voltage at a location on the elongate body that is configured to be inserted into subject, the positive voltage configured to attract a negatively charged pathogen toward the elongate body for concurrent or subsequent heat neutralization by the applying an AC electromagnetic input signal to selectively energize local heat sources in the matrix.

20. A method of using a biocompatible medical device that is at least partially implantable into a living human or animal subject, the method comprising:

obtaining or providing the medical device including an elongate body including a matrix of local heat sources;

applying an electromagnetic input signal to selectively energize local heat sources in the matrix to vary a location of locally generated heat without requiring concurrent energizing of all of the local heat sources in the matrix; and applying a DC or slowly varying AC first polarity voltage at a location on the elongate body that is configured to be inserted into subject, the first polarity voltage configured to attract a oppositely charged pathogen toward the elongate body for concurrent or subsequent heat neutralization by the applying an electromagnetic input signal to selectively energize local heat sources in the matrix.

21. The method of claim 20, wherein the obtaining or providing the medical device comprises the matrix of local heat sources including at least one of: a pair of electrodes with variable interelectrode spacing; a planar resonator structure; or a strip-line structure.

22. A method of using a biocompatible medical device that is at least partially implantable into a living human or animal subject, the method comprising:

obtaining or providing the medical device including an elongate body including a matrix of local heat sources, wherein the obtaining or providing the medical device comprises the matrix of local heat sources including at least one of: a pair of electrodes with variable interelectrode spacing; a planar resonator structure; or a strip-line structure; and applying an AC electromagnetic input signal to both selectively address and energize local heat sources in the matrix to vary a location of locally generated heat without requiring concurrent energizing of all of the local heat sources in the matrix wherein ones of the local heat sources include:

an electrical conductor, connected or coupled to receive the same AC electromagnetic input signal; and a semiconductor, a lossy dielectric, thin-film metal, or a crystalline active substrate, arranged with respect to the electrical conductor to use the same addressing and energizing AC electromagnetic input signal to generate heat in the active substrate in response to the same AC electromagnetic input signal being at the specified frequency.

23. The method of claim 22, comprising using a sensed temperature for controlling the selective energizing of ones of the local heat sources in the matrix.

24. The method of claim 22, comprising activating together a sensor and corresponding one of the heat sources in response to the electromagnetic input signal being at the specified frequency.

25. The method of claim 22, wherein the applying an electromagnetic input signal to selectively energize local heat sources in the matrix to vary a location of locally generated heat comprises establishing a temperature gradient between at least two of the local heat sources.

* * * * *

UNITED STATES PATENT AND TRADEMARK OFFICE
CERTIFICATE OF CORRECTION

| | | |
|---|---|---|
| PATENT NO. | : 10,515,831 B2 | Page 1 of 1 |
| APPLICATION NO. | : 16/027139 | |
| DATED | : December 24, 2019 | |
| INVENTOR(S) | : Anand Deo | |

It is certified that error appears in the above-identified patent and that said Letters Patent is hereby corrected as shown below:

In the Claims

In Column 44, Lines 45-46, in Claim 13, delete "conductor." and insert --conductor on or near the active substrate.-- therefor Signed and Sealed this
Nineteenth Day of January, 2021

Andrei Iancu
*Director of the United States Patent and Trademark Office*